US009404138B2

(12) United States Patent
Matsuda et al.

(10) Patent No.: US 9,404,138 B2
(45) Date of Patent: Aug. 2, 2016

(54) METHOD FOR SECRETORY PRODUCTION OF PROTEIN

(71) Applicant: AJINOMOTO CO., INC., Tokyo (JP)

(72) Inventors: Yoshihiko Matsuda, Kanagawa (JP); Haruki Beppu, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/264,600

(22) Filed: Apr. 29, 2014

(65) Prior Publication Data

US 2014/0234901 A1   Aug. 21, 2014

Related U.S. Application Data

(63) Continuation of application No. PCT/JP2012/078285, filed on Nov. 1, 2012.

(30) Foreign Application Priority Data

Nov. 2, 2011   (JP) ................................ 2011-240745

(51) Int. Cl.
| | |
|---|---|
| C12P 21/00 | (2006.01) |
| C07K 14/34 | (2006.01) |
| C12N 9/48 | (2006.01) |
| C07K 14/475 | (2006.01) |
| C07K 16/24 | (2006.01) |
| C07K 16/28 | (2006.01) |
| C12N 15/67 | (2006.01) |

(52) U.S. Cl.
CPC ................ *C12P 21/00* (2013.01); *C07K 14/34* (2013.01); *C07K 14/475* (2013.01); *C07K 16/241* (2013.01); *C07K 16/2863* (2013.01); *C12N 9/48* (2013.01); *C12N 15/67* (2013.01); *Y02P 20/52* (2015.11)

(58) Field of Classification Search
None
See application file for complete search history.

(56) References Cited

U.S. PATENT DOCUMENTS

| 4,965,197 | A | 10/1990 | Liebl et al. |
| 6,027,920 | A | 2/2000 | Joliff et al. |
| 7,252,972 | B2 | 8/2007 | Kikuchi et al. |
| 7,323,321 | B2 | 1/2008 | Rayapati et al. |
| 7,635,579 | B2 | 12/2009 | Rayapati et al. |
| 7,723,097 | B2 | 5/2010 | D'Elia et al. |
| 7,972,829 | B2 | 7/2011 | Kikuchi et al. |
| 8,034,767 | B2 | 10/2011 | Kutukova et al. |
| 8,062,869 | B2 | 11/2011 | Nakanishi et al. |
| 8,093,346 | B2 | 1/2012 | Suzuki et al. |
| 8,105,802 | B2 | 1/2012 | Umezawa et al. |
| 8,597,907 | B2 | 12/2013 | Date et al. |
| 2003/0082746 | A1 | 5/2003 | Kikuchi et al. |
| 2004/0126847 | A1 | 7/2004 | Kikuchi et al. |
| 2005/0244935 | A1 | 11/2005 | Pompejus et al. |
| 2006/0019367 | A1 | 1/2006 | Umezawa et al. |
| 2006/0154345 | A1 | 7/2006 | Rayapati et al. |
| 2007/0118916 | A1* | 5/2007 | Puzio et al. .................... 800/278 |
| 2007/0184525 | A1 | 8/2007 | Date et al. |
| 2007/0281888 | A1* | 12/2007 | Nishikawa et al. ............. 514/12 |
| 2008/0090272 | A1 | 4/2008 | Rayapati et al. |
| 2008/0241888 | A1 | 10/2008 | Zakataeva et al. |
| 2010/0159560 | A1 | 6/2010 | Umezawa et al. |
| 2010/0297729 | A1 | 11/2010 | Kikuchi et al. |

FOREIGN PATENT DOCUMENTS

| EP | 1059358 A1 | 12/2000 |
| EP | 1548116 A1 | 6/2005 |
| EP | 1602722 A1 | 12/2005 |
| EP | 1748077 A1 | 1/2007 |
| JP | 11-169182 A | 6/1999 |
| JP | 2003-506030 | 2/2003 |
| RU | 2355759 C1 | 8/2007 |
| WO | WO2013/065772 | 5/2013 |
| WO | WO2013/065869 A1 | 5/2013 |

OTHER PUBLICATIONS

Bayan et al., Journal of Biotechnology, 2003, vol. 104 pp. 55-67.*
Sundaram et al., Eur J Clin Microbial Infect Dis, 2008, vol. 27 pp. 617-622.*
Hansmeier, N., et al., "Classification of hyper-variable Corynebacterium glutamicum surface-layer proteins by sequence analyses and atomic force microscopy," J. Biotechnol. 2004;112:117-193.
Peyret, J. L., et al., "Characterization of the cspB gene encoding PS2, an ordered surface-layer protein in Corynebacterium glutamicum," Mol. Microbiol. 1993;9(1):97-109.
International Search Report for PCT Patent App. No. PCT/JP2012/078906 (Jan. 31, 2013).
Written Opinion for PCT Patent App. No. PCT/JP2012/078906 (Jan. 31, 2013).
Hansmeier, N., et al., "Classification of hyper-variable Corynebacterium glutamicum surface-layer proteins by sequence analyses and atomic force microscopy," J. Biotechnol. 2004;112:177-193. [previously cited and copy provided with IDS filed on Dec. 29, 2014. Re-cited herein to correct typographical error in page numbers].
Billman-Jacobe, H., et al., "Expression and Secretion of Heterologous Proteases by Corynebacterium glutamicum," Appl. Environmen. Microbiol. 1995;61(4):1610-1613.

(Continued)

*Primary Examiner* — Anne Gussow
*Assistant Examiner* — Mindy G Brown
(74) *Attorney, Agent, or Firm* — Shelly Guest Cermak; Cermak Nakajima & McGowan LLP

(57) ABSTRACT

A novel technique for improving ability for secretory production of a multimeric protein of a coryneform bacterium is provided, and thereby a method for secretory production of a multimeric protein is provided. A multimeric protein is produced by secretory production utilizing a coryneform bacterium having an ability to produce a multimeric protein by secretory production and modified so that expression of a gene coding for a metallopeptidase is increased as an expression host.

9 Claims, 7 Drawing Sheets

(56) References Cited

OTHER PUBLICATIONS

Christensen, T., et al., "High Level Expression of Recombinant Genes in Aspergillus Oryzae," Bio/Technology 1988;6:1419-1422.

Cregg, J. M., et al., "Recent Advances in the Expression of Foreign Genes in Pichia pastoris," Bio/Technology 1993;11:905-910.

Dunn-Coleman, N. S., et al., "Commercial Levels of Chymosin Production by Aspergillus," Bio/Technology 1991;9:976-981.

Valbuena, N., et al., "Characterization of HMW-PBPs from the rod-shaped actinomycete Corynebacterium glutamicum: peptidoglycan synthesis in cells lacking actin-like cytoskeletal structures," Mol. Microbiol. 2007;66(3):643-657.

Letek, M., et al., "Cell growth and cell division in the rod-shaped actinomycete Corynebacterium glutamicum," Antonie van Leeuwenhoek 2008;94:99-109.

Liebel, W., et al., "Expression, Secretion, and Processing of Staphylococcal Nuclease by Corynebacterium glutamicum," J. Bacteriol. 1992;174(6):1854-1861.

Salim, K., et al., "Heterologous Expression of the Mycobacterium tuberculosis Gene Encoding Antigen 85A in Corynebacterium glutamicum," Appl. Environmen. Microbiol. 1997;63(11):4392-4400.

Simonen, M., et al., "Protein secretion in *Bacillus* Species," Microbiol. Revs. 1993;57(1):109-137.

Kikuchi, Y., "Bio Iyakuhin Seisan ni Muketa Atarashii Tanpakushitsu Seisan System no Kaihatsu to Tanpakushitsu Hatsugen Jutaku Service," PharmTech Japan, vol. 27, No. 3 (2011), pp. 87(491)-91(495)—(see the IPRP for concise explanation of this reference).

International Preliminary Report on Patentability for PCT Patent App. No. PCT/JP2012/078285 (May 6, 2014).

International Search Report for PCT Patent App. No. PCT/JP2012/078285 (Feb. 12, 2013).

Pompejus, M., et al., SEQ ID No. 56, Publication Site for Issued and Published Sequences (PSIPS) [online], Nov. 2005; United States Patent and Trademark Office, Alexandria, VA, USA, [retrieved on Jan. 29, 2013] Retrieved from the Internet: <URL:http://seqdata.uspto.gov/.psipsv?pageRequest=viewSequence&DocID=2005244935&seqID=56>, SEQ ID No. 56.

Kikuchi, Y., et al., "TatABC overexpression improves Tat-dependent protein secretion in Corynebacterium glutamicum," New Biotechnol. 2009;25S:S224-S225.

Matsuda, Y., et al., "Double mutation of cell wall proteins CspB and PBP1a increases secretion of the antibody Fab fragment from Corynebacterium glutamicum," Microbial Cell Factories 2014;13:1-10.

Radmacher, E., et al., "Ethambutol, a cell wall inhibitor of Mycobacterium tuberculosis, elicits L-glutamate efflux of Corynebacterium glutamicum," Microbiol. 2005;151:1359-1368.

Supplementary European Search Report for European Patent App. No. 12845191.1 (Feb. 18, 2015).

Office Action from Russian Patent App. No. 2014122201 (Nov. 13, 2015) with English language translation.

* cited by examiner

Fig. 1

```
ATCC13032    1:MQKHTPGGKHRKQTTSPVTKGGVAFVAVATGAVSTAGAGGAVAAQASHQPVEVNFELTAN  60
ATCC13869    1:MQKHTPGGKHRKQTTSPVTKGGVAFVAVATGAVSTAGAGGAVAAQASHQPVEVNFELTAN  60
               ************************************************************

ATCC13032   61:DTTDLVAGSSAPQILSIAEFKPVVNLGDQIVKTIQYNADPIQADLDARGFSVVRPAEGSY 120
ATCC13869   61:DTTDLVAGSSAPQILSIAEFKPVVNLGDQIAKTIQYNADPIQADLDARGFSVVRPAEGSY 120
               ****************************** *****************************

ATCC13032  121:TSGFGARWGTNHNGVDIANAIGTPILAAMDGTVIDAGPASGFGNWVRLQHEDGTITVYGH 180
ATCC13869  121:TSGFGARWGTNHNGVDIANAIGTPILAAMDGTVIDAGPASGFGNWVRLQHEDGTITVYGH 180
               ************************************************************

ATCC13032  181:METVEVTVGQTVKAGERIAGNGSRGFSTGSHLHFEVPAGGGAVDPAPWLAERGITL     237
ATCC13869  181:METVEVTVGQVVRAGDRIAGNGNRGFSTGSHLHFEVPAGGGAVDPAPWLAERGITL     237
               ********** * ** ***** ****************************************
```

METHOD FOR SECRETORY PRODUCTION OF PROTEIN

This application is a Continuation of, and claims priority under 35 U.S.C. §120 to, International Application No. PCT/JP2012/078285, filed Nov. 1, 2012, and claims priority therethrough under 35 U.S.C. §119 to Japanese Patent Application No. 2011-240745, filed Nov. 2, 2011, the entireties of which are incorporated by reference herein. Also, the Sequence Listing filed electronically herewith is hereby incorporated by reference (File name: 2014-04-29T_US-512_Seq_List; File size: 63 KB; Date recorded: Apr. 29, 2014).

BACKGROUND OF THE INVENTION

1. Field of the Invention

The present invention relates to a coryneform bacterium that is able to efficiently produce a heterologous protein by secretory production and a method for secretory production of a heterologous protein. Specifically, the heterologous protein produced by secretory production according to the present invention is a multimeric protein.

2. Brief Description of the Related Art

To date, secretory production of heterologous proteins by microorganisms has been reported in *Bacillus* bacterium (Microbiol. Rev., 57, 109-137 (1993)), methanol-assimilating yeast, *Pichia pastoris* (Biotechnol., 11, 905-910 (1993)), filamentous fungi of the genus *Aspergillus* (Biotechnol., 6, 1419-1422 (1988) and Biotechnol., 9, 976-981 (1991)), and so forth.

Secretory production of heterologous proteins by coryneform bacteria has also been reported, specifically secretion of a nuclease and a lipase by *Corynebacterium glutamicum* (henceforth also abbreviated as *C. glutamicum*) (U.S. Pat. No. 4,965,197, J. Bacteriol., 174, 1854-1861 (1992)), secretion of a protease such as subtilisin (Appl. Environ. Microbiol., 61, 1610-1613 (1995)), secretion of a protein using signal peptides of cell surface layer proteins PS1 and PS2 (also referred to as CspB) of coryneform bacteria (Japanese Patent Laid-open (Kohyo) No. 6-502548), secretion of a fibronectin-binding protein using the signal peptide of PS2 (CspB) (Appl. Environ. Microbiol., 63, 4392-4400 (1997)), secretion of protransglutaminase using signal peptides of cell surface layer proteins PS2 (CspB) and SlpA (also referred to as CspA) of coryneform bacteria (Japanese Patent No. 4320769), secretion of a protein using a variant type secretion system (Japanese Patent Laid-open (Kokai) No. 11-169182), secretion of a protransglutaminase by a variant strain (Japanese Patent No. 4362651), secretion of a protein using a Tat-dependent signal peptide (Japanese Patent No. 4730302), and so forth.

Various proteins have been suggested as proteins that could be produced by secretory production; however, in coryneform bacteria, there are no reports of secretory production of any multimeric protein such as, for example, antibody-related molecules.

Metallopeptidases are a class of protease that requires various metal ions, such as zinc and calcium, for activation, and have an activity of decomposing various kinds of proteins. Among the metallopeptidases, metallopeptidases belonging to the M23/M37 family (also referred to as M23/M37 metallopeptidases) require zinc ion. It has already been elucidated that the Cgl0858 gene of *C. glutamicum* is a gene coding for a protein that includes a region homologous to a motif of M23/M37 metallopeptidases on the basis of the sequence information. However, the function of the protein encoded by the Cgl0858 gene in *C. glutamicum* is still elusive. Moreover, the ability to improve the production amount of an objective heterologous protein due to high expression of a gene coding for a region homologous to this motif of the M23/M37 metallopeptidases has not been reported for any biological species.

Penicillin-binding protein (PBP) is a generic term which describes proteins that bind with β-lactam type antibiotics, and as a result, inhibit binding with β-lactam type antibiotics. PBPs are generally membrane-binding proteins, and they are considered essential for cell wall synthesis of eubacteria. PBPs are classified as high molecular weight PBPs (HMW-PBPs) or low molecular weight PBPs (LMW-PBPs), according to the molecular weights thereof. HMW-PBPs are further classified as class A high molecular weight PBPs (class A HMW-PBPs), which have both a transpeptidase activity domain for crosslinking peptidoglycan moieties, and a transglycosylase activity domain for forming a polysaccharide chain from disaccharides, and class B high molecular weight PBPs (class B HMW-PBPs) which have only a transpeptidase activity domain.

The findings about PBPs of *C. glutamicum* are detailed in Mol. Microbiol., 66, 643-57 (2007), Antonie Van Leeuwenhoek, 94, 99-109 (2008), and so forth. In *C. glutamicum*, at least nine PBP homologues have been found so far. Five of them are HMW-PBPs including two class A HMW-PBPs (PBP1a, PBP1b) and three class B HMW-PBPs (FtsI, PBP2a, PBP2b). It is known that the class A HMW-PBPs of *C. glutamicum* are responsible for cell extension, and the class B HMW-PBPs are responsible for formation of peptidoglycan of septal walls at the time of cell division.

However, the relationship between penicillin-binding protein and the secretory production of a heterologous protein has not been previously reported.

SUMMARY OF THE INVENTION

Aspects to be Achieved by the Invention

An aspect of the present invention is to develop a novel technique for improving the ability of a coryneform bacterium to produce a multimeric protein by secretory production, and thereby to provide a coryneform bacterium that produces a multimeric protein by secretory production and a method for secretory production of a multimeric protein using such a bacterium.

A method for producing a heterologous protein utilizing a coryneform bacterium as an expression host is described, wherein the ability of the coryneform bacterium to produce a multimeric protein by secretory production is improved by modifying the coryneform bacterium so that the expression of a gene coding for a metallopeptidase is increased.

It is an aspect of the present invention to provide a coryneform bacterium having an ability to produce a multimeric protein by secretory production, which is modified so that expression of a gene coding for a metallopeptidase is increased.

It is a further aspect of the present invention to provide the bacterium as described above, wherein the expression of the gene is increased by increasing copy number of the gene or by modifying an expression control sequence of the gene.

It is a further aspect of the present invention to provide the bacterium as described above, wherein the metallopeptidase is an M23/M37 metallopeptidase or a protein comprising a region homologous to a motif of an M23/M37 metallopeptidase.

It is a further aspect of the present invention to provide the bacterium as described above, wherein the metallopeptidase is a protein selected from the group consisting of:

(A) a protein comprising the amino acid sequence shown in SEQ ID NO: 4, (B) a protein comprising the amino acid sequence shown in SEQ ID NO: 4, but which includes substitution, deletion, insertion, or addition of 1 to 10 amino acid residues, and wherein said protein has a property that if expression thereof is increased in the coryneform bacterium, the secretory production amount of the multimeric protein is increased compared with that observed for a non-modified strain.

It is a further aspect of the present invention to provide the bacterium as described above, which is further modified so that the activity of a penicillin-binding protein is reduced.

It is a further aspect of the present invention to provide the bacterium as described above, wherein the activity of a cell surface layer protein is reduced.

It is a further aspect of the present invention to provide the bacterium as described above, which belongs to the genus *Corynebacterium* or *Brevibacterium*.

It is a further aspect of the present invention to provide the bacterium as described above, which is *Corynebacterium glutamicum*.

It is a further aspect of the present invention to provide the bacterium as described above, wherein the coryneform bacterium has a genetic construct for secretory expression of the multimeric protein, and wherein the genetic construct comprises a promoter sequence that functions in the coryneform bacterium, a nucleic acid sequence coding for a signal peptide that functions in the coryneform bacterium, which is ligated downstream from the promoter sequence, and a nucleic acid sequence coding for the multimeric protein, which is ligated downstream from the nucleic acid sequence coding for the signal peptide.

It is a further aspect of the present invention to provide the bacterium as described above, wherein the multimeric protein is an antibody-related molecule.

It is a further aspect of the present invention to provide the bacterium as described above, wherein the antibody-related molecule is a protein selected from the group consisting of Fab, F(ab')$_2$, Fc fusion protein, and combinations thereof.

It is a further aspect of the present invention to provide the bacterium as described above, wherein the multimeric protein is the vascular endothelial cell growth factor A (VEGF-A).

It is a further aspect of the present invention to provide a method for producing a multimeric protein comprising: culturing the coryneform bacterium as mentioned above; and collecting the protein produced by secretory production.

BRIEF DESCRIPTION OF THE DRAWINGS

FIG. 1 shows an alignment of the amino acid sequences of the protein encoded by Cgl0858 of *C. glutamicum* ATCC 13032 (SEQ ID NO: 98) and the protein encoded by the Cgl0858 homologue of *C. glutamicum* ATCC 13869 (SEQ ID NO: 4).

DESCRIPTION OF THE PREFERRED EMBODIMENTS

Figure 2:
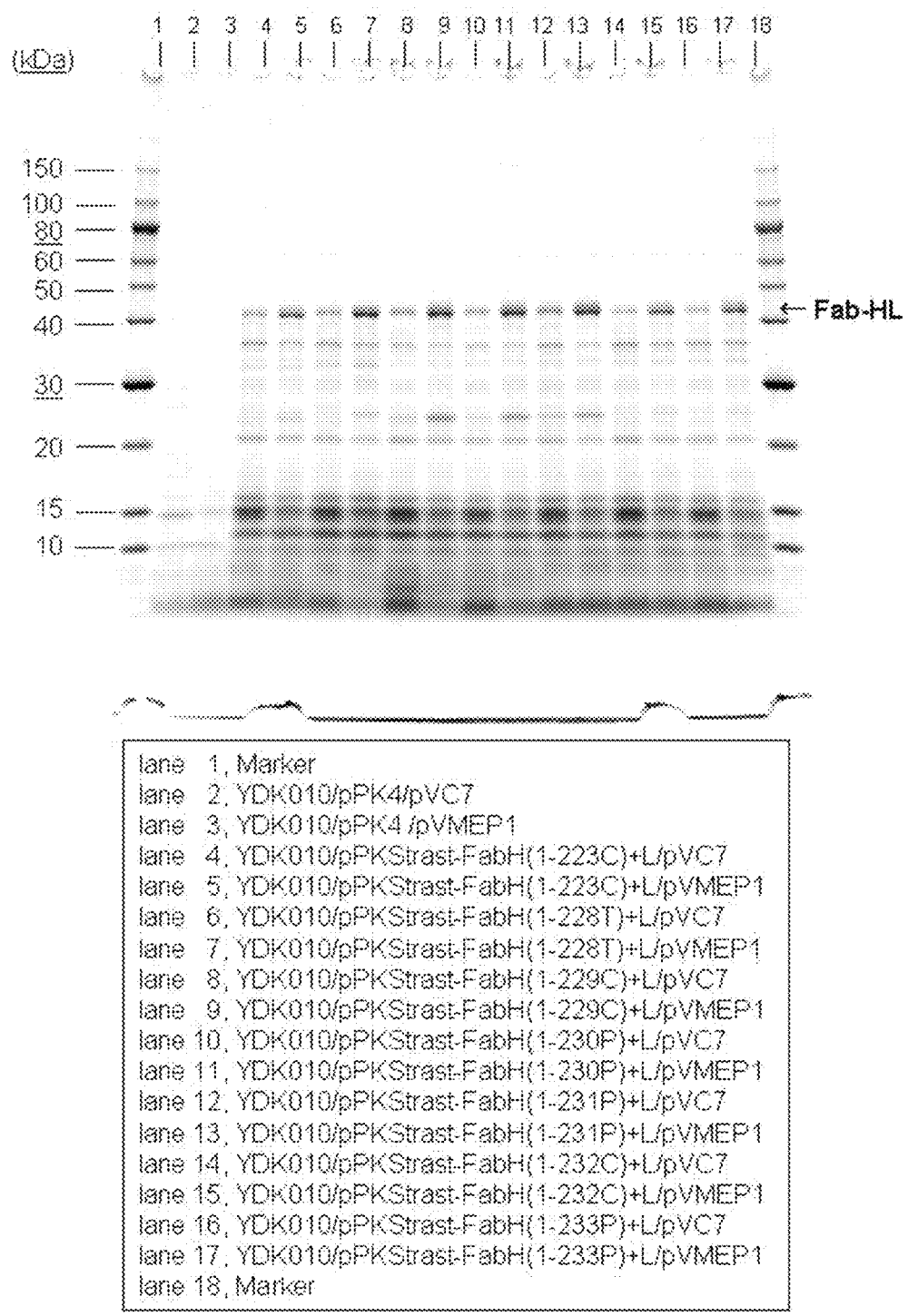
FIG. 2 is a photograph showing the results of non-reduced SDS-PAGE of the H chain region and the L chain region of the Fab fragment of trastuzumab coexpressed in the *C. glutamicum* YDK010 strain and a metallopeptidase expression-enhanced strain thereof.

<1> Coryneform Bacterium of the Present Invention

The present invention provides a coryneform bacterium having an ability to produce a multimeric protein by secretory production, which is modified so that the expression of a gene coding for a metallopeptidase is increased (henceforth also referred to as the "bacterium of the present invention" or the "coryneform bacterium of the present invention").

The expression that a protein is "secreted" can mean that the protein is transported out of the bacterial cell, that is, extracellularly transported. The expression that a protein is "secreted" of course can include when all the protein molecules eventually are present in a medium in completely free forms, when all the protein molecules are present in the cell surface layer, and/or when some of the protein molecules are present in the medium and some are present in the cell surface layer.

That is, the "ability to produce a multimeric protein by secretory production" can refer to an ability of the bacterium of the present invention to secrete the multimeric protein into a medium or the cell surface layer, and allow it to accumulate there to such an extent that the multimeric protein can be collected from the medium or the cell surface layer, when the bacterium is cultured in the medium. The accumulation amount may be, for example, in terms of the accumulation amount in the medium, 10 µg/L or more, 1 mg/L or more, 100 mg/L or more, 1 g/L or more. Also, the accumulation amount may be, for example, in terms of the accumulation amount in the cell surface layer, such an amount that if the multimeric protein in the cell surface layer is collected and suspended in a liquid of the same volume as the medium, the concentration of the multimeric protein in the suspension is 10 µg/L or more, 1 mg/L or more, 100 mg/L or more. In addition, the term "protein" to be produced by secretory production can refer to molecules called a peptide or polypeptide.

The multimeric protein to be produced by secretory production is not particularly limited so long as it is a heterologous multimeric protein. The "heterologous protein" can refer to an exogenous protein relative to the coryneform bacterium that expresses and secretes that protein. The heterologous protein may be, for example, a protein derived from a microorganism, a protein derived from a plant, a protein derived from an animal, a protein derived from a virus, or even a protein with an artificially designed amino acid sequence. The multimeric protein can contain two or more subunits. In the multimer, the subunits may be linked by covalent bonds such as disulfide bonds, linked by non-covalent bonds such as hydrogen bonds and hydrophobic interaction, or linked by a combination thereof. The multimer can include one or more intermolecular disulfide bonds. The multimer can be a homo-multimer consisting of a single kind of subunit, or may be a hetero-multimer consisting of two or more kinds of subunits. For the hetero-multimer, it is sufficient that at least one subunit is a heterologous protein. That is, all the subunits may be heterologous, or only a part of subunits may be heterologous. Although the multimeric protein may be a secretory protein in nature, or may be a non-secretory protein in nature, it is preferably a secretory protein in nature. Specific examples of the "multimeric protein" are described herein.

The multimeric protein to be produced by secretory production can be a single kind of protein, or two or more kinds of proteins. When the multimeric protein is a hetero-multimer, all the subunits of the hetero-multimer are produced by secretory production.

The coryneform bacteria are aerobic gram-positive bacilli, and include *Corynebacterium* bacteria, *Brevibacterium* bacteria, *Microbacterium* bacteria, and so forth. The coryneform bacteria include bacteria which have previously been classified into the genus *Brevibacterium* but are presently united into the genus *Corynebacterium* (Int. J. Syst. Bacteriol., 41, 255 (1991)). The coryneform bacteria also include bacteria which have previously been classified into *Corynebacterium ammoniagenes* but are presently reclassified into *Corynebacterium stationis* by nucleotide sequence analysis of 16S rRNA and so forth (Int. J. Syst. Evol. Microbiol., 60, 874-879 (2010)). Advantages of using coryneform bacteria include that they inherently secrete an extremely small amount of proteins to the outside of cells compared with fungi, yeasts, *Bacillus* bacteria, etc., which are conventionally used for secretory production of proteins, and therefore the purification process of a heterologous protein produced by secretory production is expected to be simplified or eliminated. Another advantage is that they can grow well in a simple medium containing a saccharide, ammonia, mineral salts, etc., and therefore they are excellent in view of cost of medium, culture method, and culture productivity, and so forth.

Specific examples of coryneform bacteria include the following species:
*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum*
*Brevibacterium flavum*
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Corynebacterium ammoniagenes* (*Corynebacterium stationis*)
*Brevibacterium album*
*Brevibacterium cerinum*
*Microbacterium ammoniaphilum*

Specific examples of coryneform bacteria include the following strains:
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, ATCC 13032, ATCC 13060, ATCC 13869, FERM BP-734
*Corynebacterium lilium* ATCC 15990
*Corynebacterium melassecola* ATCC 17965
*Corynebacterium thermoaminogenes* AJ12340 (FERM BP-1539)
*Corynebacterium herculis* ATCC 13868
*Brevibacterium divaricatum* ATCC 14020
*Brevibacterium flavum* ATCC 13826, ATCC 14067, AJ12418 (FERM BP-2205)
*Brevibacterium immariophilum* ATCC 14068
*Brevibacterium lactofermentum* ATCC 13869
*Brevibacterium roseum* ATCC 13825
*Brevibacterium saccharolyticum* ATCC 14066
*Brevibacterium thiogenitalis* ATCC 19240
*Corynebacterium ammoniagenes* (*Corynebacterium stationis*) ATCC 6871, ATCC 6872
*Brevibacterium album* ATCC 15111
*Brevibacterium cerinum* ATCC 15112
*Microbacterium ammoniaphilum* ATCC 15354

These strains are available from, for example, the American Type Culture Collection (Address: P.O. Box 1549, Manassas, Va. 20108, United States of America). That is, registration numbers are assigned to the respective strains, and the strains can be ordered by using these registration numbers (refer to atcc.org). The registration numbers of the strains are listed in the catalogue of the American Type Culture Collection.

In particular, the *Corynebacterium glutamicum* (*C. glutamicum*) AJ12036 strain (FERM BP-734), which was isolated as a streptomycin (Sm) resistant mutant strain from the wild-type strain, *C. glutamicum* ATCC 13869, is predicted to have a mutation in the functional gene responsible for secretion of proteins, and shows an extremely high secretory production ability for heterologous proteins as high as about 2 to 3 times in terms of accumulation the amount of proteins under optimum culture conditions, compared with the parent strain (wild-type strain), and therefore it is preferred as a host bacterium. The AJ12036 strain was originally deposited at the National Institute of Bioscience and Human-Technology, Agency of Industrial Science and Technology (currently, the incorporated administrative agency, National Institute of Technology and Evaluation, International Patent Organism Depositary, Tsukuba Central 6, 1-1, Higashi 1-Chome, Tsukuba-shi, Ibaraki-ken, 305-8566, Japan) on Mar. 26, 1984 as an international deposit, and assigned an accession number of FERM BP-734.

Moreover, a strain having an enhanced ability to produce a protein by secretory production may be selected from such coryneform bacteria as mentioned above as a parent strain by using a mutagenesis method or a genetic recombination method, and used as a host. For example, after a parent strain is treated with ultraviolet irradiation or a chemical mutation agent such as N-methyl-N'-nitrosoguanidine, a strain having an enhanced ability to produce a protein by secretory production can be selected.

Furthermore, if a strain obtained by modifying such a strain as mentioned above so that it does not produce a cell surface layer protein is used as the host, purification of the heterologous protein secreted in the medium or on the cell surface layer becomes easy, and therefore it is particularly preferred. Such modification can be carried out by introducing a mutation into the coding region of the cell surface layer protein or an expression control region thereof, on the chromosome by mutagenesis or genetic recombination. Examples of coryneform bacterium modified so that it does not produce a cell surface layer protein can include the *C. glutamicum* YDK010 strain (WO2004/029254), which is a cell surface layer protein PS2 (CspB) deficient strain of the *C. glutamicum* AJ12036 strain (FERM BP-734).

The coryneform bacterium having an ability to produce a multimeric protein by secretory production can be obtained by introducing a genetic construct for secretory expression of the multimeric protein into such a coryneform bacterium as mentioned above so that the bacterium harbors the genetic construct. That is, the bacterium of the present invention has a genetic construct for secretory expression of a multimeric protein. The "genetic construct for secretory expression of a multimeric protein" and a method for introducing it is described herein.

The bacterium of the present invention is modified so that the expression of a gene coding for a metallopeptidase is increased. The bacterium of the present invention can be obtained by modifying a coryneform bacterium having an ability to produce a multimeric protein by secretory production so that the expression of a gene coding for a metallopeptidase is increased. Alternatively, the bacterium of the present invention can also be obtained by modifying a coryneform bacterium so that the expression of a gene coding for a metallopeptidase is increased, and then imparting an ability to produce a multimeric protein by secretory production to it. In the present invention, the modification and impartation of the ability for constructing the bacterium of the present invention can be carried out in an arbitrary order. The bacterium of the present invention may be a bacterium obtained from a bacterium that can produce a multimeric protein by secretory production even before it is modified so that the expression of a gene coding for a metallopeptidase is increased. Alternatively, the bacterium of the present invention may also be a bacterium obtained from a bacterium that cannot produce a multimeric protein by secretory production even when it has a genetic construct for secretory expression of a multimeric protein before it is modified so that the expression of a gene coding for a metallopeptidase is increased, which comes to be able to produce the multimeric protein by secretory production as a result of such modification that the expression of a gene coding for a metallopeptidase is increased.

Hereafter, metallopeptidases and genes coding for them will be explained.

Metallopeptidases are a class of protease that requires various metal ions such as zinc and calcium for activation thereof, and have an activity of decomposing various kinds of proteins. This activity can also be referred to as metallopeptidase activity. Although the metallopeptidase with enhanced expression is not particularly limited, it can be an M23/M37 metallopeptidase. The M23/M37 metallopeptidase is a metalloendopeptidase that requires zinc ion. Specific examples of the M23/M37 metallopeptidase can include, for example, the protein encoded by the ale-1 gene of the *Staphylococcus capitis* EPK1 strain.

Furthermore, the metallopeptidase with enhanced expression can be a protein that includes a region homologous to a motif of a metallopeptidase as described above. For example, the metallopeptidase with enhanced expression can be a protein that includes a region homologous to a motif of an M23/M37 metallopeptidase. Specific examples of the protein containing a region homologous to a motif of an M23/M37 metallopeptidase can include, for example, the protein encoded by the Cgl0858 gene of *C. glutamicum* ATCC 13032 and the protein encoded by the Cgl0858 homologue gene of *C. glutamicum* ATCC 13869. Specific examples of the protein containing a region homologous to a motif of an M23/M37 metallopeptidase can also include, for example, the protein encoded by the nlpD gene of the *Escherichia coli* (*E. coli*) K12 MG1655 strain.

The metallopeptidase with enhanced expression has a property that if the expression thereof is increased in a coryneform bacterium, the secretory production amount of the multimeric protein is increased compared with that observed for a non-modified strain. In addition, the metallopeptidase with enhanced expression may have or may not have the metallopeptidase activity.

The phrase "property that if the expression thereof is increased in a coryneform bacterium, the secretory production amount of a multimeric protein is increased compared with that observed for a non-modified strain" can refer to a property of imparting an ability to produce a multimeric protein by secretory production in an amount larger than that observed for a non-modified strain, such as wild-type strain or parent strain to a coryneform bacterium when the expression thereof is increased in the coryneform bacterium. The expression "to produce a multimeric protein by secretory production in an amount larger than that observed for a non-modified strain" may mean, but is not particularly limited to, so long as the secretory production amount of the multimeric protein increases compared with that observed for a non-modified strain, for example, that the multimeric protein is produced by secretory production in an amount larger than that observed for a non-modified strain by 10% or more, 20% or more, 30% or more, 100% or more, in terms of the accumulation amount in the medium and/or the cell surface layer. In addition, the expression "to produce a multimeric protein by secretory production in an amount larger than that observed for a non-modified strain" may also mean that whereas the multimeric protein cannot be detected when a non-concentrated culture supernatant of a non-modified strain is applied to SDS-PAGE and stained with CBB, the multimeric protein can be detected when a non-concentrated culture supernatant of a modified strain is applied to SDS-PAGE and stained with CBB.

Whether a protein has a property that if the expression thereof is increased in a coryneform bacterium, the secretory production amount of a multimeric protein is increased compared with that observed for a non-modified strain can be confirmed by preparing a strain from a strain belonging to the coryneform bacteria by modification so that the expression of the gene thereof is increased, quantifying the secretory production amount of the multimeric protein observed when the modified strain is cultured in a medium, and comparing the quantified amount with the secretory production amount of the multimeric protein observed when the strain before being modified (non-modified strain) is cultured in the medium. As the non-modified strain referred to above, for example, a coryneform bacterium having the genetic construct for secretory expression of a multimeric protein can be used. Specifically, as the non-modified strain, for example, a strain obtained by introducing the genetic construct for secretory expression of a multimeric protein into the *C. glutamicum* AJ12036 (FERM BP-734) or *C. glutamicum* YDK010 strain can be used.

Further, the phrase "property that if the expression thereof is increased in a coryneform bacterium, the secretory production amount of the multimeric protein is increased compared with that observed for a non-modified strain" of the metallopeptidase may be, specifically, the metallopeptidase activity.

Whether a protein has the metallopeptidase activity can be confirmed by measuring that activity. The metallopeptidase activity can be measured by a method well known to those skilled in the art. Specifically, the metallopeptidase activity can be measured with, for example, a metalloprotease assay kit (Oxford Biomedical Research), or the like.

The ale-1 gene of the *Staphylococcus capitis* (*S. capitis*) EPK1 strain is registered in the NCBI database as GenBank accession BAA13069 (VERSION BAA13069.1 GI: 1890068).

The Cgl0858 gene of *C. glutamicum* ATCC 13032 corresponds to a sequence complementary to the sequence of the positions 916,967 to 917,680 in the genomic sequence registered in the NCBI database as GenBank accession BA000036 (VERSION BA000036.3 GI: 42602314). The amino acid sequence of the protein encoded by the Cgl0858 gene of *C. glutamicum* ATCC 13032 is shown in SEQ ID NO: 98. Further, the nucleotide sequence of the Cgl0858 homologue gene of *C. glutamicum* ATCC 13869 and the amino acid sequence of the protein encoded by this gene are shown in SEQ ID NOS: 3 and 4, respectively.

The nlpD gene of the *Escherichia coli* (*E. coli*) K12 MG1655 strain corresponds to a sequence complementary to the sequence of the positions 2,865,636 to 2,866,775 in the genomic sequence registered in the NCBI database as GenBank accession NC_000913 (VERSION NC_000913.2 GI: 49175990). The nlpD gene of the *E. coli* K12 MG1655 strain is synonymous with ECK2737 or JW2712.

Since the nucleotide sequence of the gene coding for a metallopeptidase may differ depending on the genus, species, or strain to which the bacterium belongs, the gene coding for a metallopeptidase may be a variant of the aforementioned nucleotide sequence, so long as it codes for a protein having a property that if the expression thereof is increased in a coryneform bacterium, the secretory production amount of the multimeric protein is increased compared with that observed for a non-modified strain. The variants of the Cgl0858 gene, the nlpD gene, and the ale-1 gene can include homologues of the genes. Homologues of the Cgl0858 gene, the nlpD gene, and the ale-1 gene can be easily obtained from public databases by BLAST search or FASTA search using the aforementioned wild-type Cgl0858 gene of *C. glutamicum*, the wild-type nlpD gene of *E. coli*, or the wild-type ale-1 gene of *S. capitis* as a query sequence, and can also be obtained by PCR using a chromosome of a bacterium belonging to the family Enterobacteriaceae or a coryneform bacterium as a template and oligonucleotides prepared on the basis of a known gene sequence such as those mentioned above as primers.

The gene coding for a metallopeptidase may be a gene coding for a protein having the aforementioned amino acid sequence including substitution, deletion, insertion, or addition of one or several amino acid residues at one or several positions, so long as it codes for a protein having a property that if the expression thereof is increased in a coryneform bacterium, the secretory production amount of the multimeric protein is increased compared with that observed for a non-modified strain. In such a case, usually 70% or more, 80% or more, 90% or more of the property that if the expression thereof is increased in a coryneform bacterium, the secretory production amount of the multimeric protein is increased compared with that observed for a non-modified strain is maintained against that of the protein not introduced with substitution, deletion, insertion, or addition of one or several amino acid residues. Although the number of "one or several" may differ depending on the position in the three-dimensional structure of the protein or types of amino acid residues, specifically, it is 1 to 20, 1 to 10, or 1 to 5.

The aforementioned substitution, deletion, insertion, or addition of one or several amino acid residues can be a conservative mutation that maintains the normal function of the protein. Typical examples of conservative mutations are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, such substitution, deletion, insertion, addition, inversion or the like of amino acid residues as mentioned above includes a naturally occurring mutation due to an individual difference, or a difference of species of a bacterium from which the gene is derived (mutant or variant).

Furthermore, the gene having such a conservative mutation as mentioned above may be a gene coding for a protein showing a homology of 80% or more, 90% or more, 95% or more, 97% or more, 99% or more, to the total encoded amino acid sequence, and having a property that if the expression of the protein is increased in a coryneform bacterium, the secretory production amount of the multimeric protein is increased compared with that observed for a non-modified strain. In addition, in this specification, "homology" may mean "identity".

Moreover, the gene coding for a metallopeptidase may be a DNA that is able to hybridize with a probe that can be prepared from a known gene sequence, such as a sequence complementary to a part or the whole of the aforementioned nucleotide sequence, under stringent conditions, and codes for a protein having a property that if the expression of the protein is increased in a coryneform bacterium, the secretory production amount of the multimeric protein is increased compared with that observed for a non-modified strain. The "stringent conditions" can refer to conditions under which a so-called specific hybrid is formed, and a non-specific hybrid is not formed. Examples of the stringent conditions can include those under which highly homologous DNAs hybridize to each other, for example, DNAs not less than 80% homologous, not less than 90% homologous, not less than 95% homologous, not less than 97% homologous, not less than 99% homologous, hybridize to each other, and DNAs less homologous than the above do not hybridize to each other, or conditions of washing of typical Southern hybridization, i.e., conditions of washing once, preferably 2 or 3 times, at a salt concentration and temperature corresponding to 1×SSC, 0.1% SDS at 60° C., 0.1×SSC, 0.1% SDS at 60° C., 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing the nucleotide sequence as a template. For example, when a DNA fragment having a length of about 300 bp is used as the probe, the washing conditions of the hybridization may be, for example, 50° C., 2×SSC and 0.1% SDS.

Furthermore, although a naturally occurring gene coding for a metallopeptidase can be used as it is, a gene coding for a metallopeptidase in which an arbitrary codon is replaced with an equivalent codon may also be used. For example, the gene coding for a metallopeptidase may be modified so that it has optimal codons according to codon frequencies in a host to be used.

The above descriptions concerning variants of the genes and proteins can also be applied mutatis mutandis to arbitrary proteins such as cell surface layer proteins, penicillin-binding proteins, and multimeric proteins to be produced by secretory production according to the present invention, and genes coding for them.

The method for increasing the expression of a gene will be explained below.

The phrase "the expression of a gene is increased" can mean that the expression amount of the target gene is increased compared with that observed in a non-modified strain such as wild-type strain or parent strain. Although the degree of the increase of the expression of the gene is not particularly limited so long as the expression is increased compared with that observed in a non-modified strain, it can be increased 1.5 times or more, 2 times or more, 3 times or more, compared with that observed in a non-modified strain. Further, the phrase "the expression of a gene is increased" can include not only a case where the expression amount of a target gene is increased in a strain in which the target gene is originally expressed, but also a case where a target gene is expressed in a strain that does not originally express the gene. That is, the phrase "expression of a gene is increased" can include, for example, the case where the target gene is introduced into a strain that does not have the gene, and expressed in it.

The expression of a gene can be increased by, for example, increasing the copy number of the gene.

The copy number of a target gene can be increased by introducing the gene into the chromosome of a host microorganism. A gene can be introduced into a chromosome by a method of randomly introducing it into a chromosome using a transposon or Mini-Mu (Japanese Patent Laid-open (Kokai) No. 2-109985, U.S. Pat. No. 5,882,888, European Patent Publication No. 805867 B1), or by homologous recombination using a sequence present on a chromosomal DNA in a multiple copy number as a target. As a sequence present on a chromosomal DNA in a multiple copy number, a repetitive DNA, and inverted repeats located at the both ends of a transposon can be used. Alternatively, a gene can also be introduced into a chromosome by using the Red driven integration method (WO2005/010175). Moreover, a gene can also be introduced into a chromosome by transduction using a phage, or by using a conjugative transfer vector. Furthermore, a gene can also be introduced using a gene unnecessary for production of a heterologous protein on a chromosome as a target, as described in WO03/040373. One or plural copies of a gene can be introduced into a target sequence by such methods as described above.

Introduction of a target gene into a chromosome can be confirmed by Southern hybridization using a probe having a sequence complementary to the whole or a part of the gene, PCR using primers prepared on the basis of the sequence of the gene, or the like.

Furthermore, the copy number of a target gene can also be increased by introducing a vector containing the gene into a host bacterium. For example, copy number of a target gene can be increased by ligating a DNA fragment containing the target gene with a vector that functions in a host bacterium to construct an expression vector of the gene, and transforming the host bacterium with the expression vector. As the vector, a vector autonomously replicable in the cell of the host bacterium can be used. The vector can be a multi-copy vector. Further, the vector preferably includes a marker such as an antibiotic resistance gene for selection of transformants. The vector may be, for example, a vector derived from a bacterial plasmid, a vector derived from a yeast plasmid, a vector derived from a bacteriophage, cosmid, phagemid, or the like. Specific examples of vector autonomously replicable in coryneform bacteria include pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAM330 described in Japanese Patent Laid-open (Kokai) No. 58-67679; pHM1519 described in Japanese Patent Laid-open (Kokai) No. 58-77895; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; pCG4 and pCG11 described in Japanese Patent Laid-open (Kokai) No. 57-183799; pVK7 described in Japanese Patent Laid-open (Kokai) No. 10-215883; pVC7 described in Japanese Patent Laid-open (Kokai) No. 9-070291; and so forth.

Furthermore, the expression of a gene can also be increased by improving the transcription efficiency of the gene. The transcription efficiency of a gene can be improved by, for example, substituting a stronger promoter for the promoter of the gene on the chromosome. The "stronger promoter" can mean a promoter providing improved transcription of a gene compared with the native wild-type promoter. As a stronger promoter, for example, known high expression promoters, such as T7 promoter, trp promoter, lac promoter, tac promoter, and PL promoter, can be used. Further, as the stronger promoter, a highly-active type of an existing promoter can be obtained by using various reporter genes. For example, by making the −35 and −10 regions in a promoter region closer to the consensus sequence, the activity of the promoter can be enhanced (International Patent Publication WO00/18935). Methods for evaluating the strength of promoters and examples of strong promoter are described in the paper of Goldstein et al. (Prokaryotic Promoters in Biotechnology, Biotechnol. Annu. Rev., 1, 105-128 (1995)), and so forth.

Furthermore, expression of a gene can also be increased by improving the translation efficiency of the gene. The translation efficiency of a gene can be improved by, for example, replacing the Shine-Dargarno (SD) sequence (also referred to as ribosome binding site (RBS)) of the gene on a chromosome with a stronger SD sequence. The "stronger SD sequence" can mean a SD sequence that provides improved translation of mRNA compared with the originally existing wild-type SD sequence. Examples of the stronger SD sequence include, for example, RBS of the gene 10 derived from phage T7 (Olins P. O. et al, Gene, 1988, 73, 227-235). Further, it is known that substitution, insertion, or deletion of several nucleotides in a spacer region between RBS and the start codon, especially in a sequence immediately upstream of the start codon (5'-UTR), significantly affects the stability and translation efficiency of mRNA, and the translation efficiency of a gene can also be improved by modifying them.

Sites affecting gene expression, such as promoter, SD sequence, and spacer region between RBS and the start codon, are also collectively called an "expression control region". An expression control region can be determined by using a promoter-search vector or gene analysis software such as GENETYX. Such an expression control region can be modified by, for example, a method using a temperature sensitive vector or the Red driven integration method (WO2005/010175).

Furthermore, the expression of a target gene can also be increased by amplifying a regulator that increases the expression of the gene, or deleting or attenuating a regulator that reduces the expression of the gene.

Such methods for increasing the expression of a gene as mentioned above may be used independently or in an arbitrary combination.

The method for the transformation is not particularly limited, and conventionally known methods can be used. There can be used, for example, a method of treating recipient cells with calcium chloride so as to increase permeability thereof for DNA, which has been reported for *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for *Bacillus subtilis* (Duncan, C. H., Wilson, G. A. and Young, F. E., Gene, 1977, 1:153-167). Alternatively, there can also be used a method of making DNA-recipient cells into protoplasts or spheroplasts, which can easily take up recombinant DNA, followed by introducing a recombinant DNA into the cells, which is known to be applicable to *Bacillus subtilis*, actinomycetes and yeasts (Chang, S, and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Further, a coryneform bacterium can also be transformed by the electric pulse method (Japanese Patent Laid-open (Kokai) No. 2-207791).

An increase in the expression of a target gene can be confirmed by, for example, confirming the increase in the activity of the target protein expressed from the gene. An increase in the activity of the target protein can be confirmed by measuring the activity of the protein. The activity of the protein can be increased 1.5 times or more, 2 times or more, or 3 times or more, compared with that observed in a non-modified strain. The metallopeptidase activity can be measured by a method well known to those skilled in the art. Specifically, the metallopeptidase activity can be measured with, for example, a metalloproteinase assay kit (Oxford Biomedical Research), or the like.

An increase in the expression of a target gene can be confirmed by confirming increase in the transcription amount of the gene, or by confirming increase in the amount of the target protein expressed from the gene.

An increase in the transcription amount of a target gene can be confirmed by comparing the amount of mRNA transcribed from the gene with that of a non-modified strain such as wild-type strain or parent strain. Examples of the method for evaluating the amount of mRNA include Northern hybridization, RT-PCR, and so forth (Sambrook, J., et al., Molecular Cloning A Laboratory Manual/Third Edition, Cold spring Harbor Laboratory Press, Cold Spring Harbor (USA), 2001).

The amount of mRNA can increase, for example, 1.5 times or more, 2 times or more, or 3 times or more, compared with that of a non-modified strain.

An increase in the amount of a target protein can be confirmed by Western blotting using an antibody (Molecular Cloning, Cold Spring Harbor Laboratory Press, Cold Spring Harbor (USA), 2001). The amount of the protein can be increased, for example, 1.5 times or more, 2 times or more, or 3 times or more, compared with that of a non-modified strain.

The bacterium of the present invention may further have a property of improving secretory production ability for a heterologous protein. For example, the bacterium of the present invention may be modified so that the activity of a penicillin-binding protein is reduced. Further, the bacterium of the present invention may be, for example, a bacterium in which the activity of a cell surface layer protein is reduced.

Hereafter, penicillin-binding proteins and genes coding for them will be explained.

In general, the penicillin-binding proteins (PBPs) can refer to proteins that bind with β-lactam type antibiotics, and as a result, inhibit their enzymatic function. The penicillin-binding proteins include high molecular weight PBPs (HMW-PBPs) and low molecular weight PBPs (LMW-PBPs). The high molecular weight PBPs include class A high molecular weight PBPs (class A HMW-PBPs) and class B high molecular weight PBPs (class B HMW-PBPs). The class A HMW-PBPs have both a transpeptidase activity domain for crosslinking peptidoglycan moieties and a transglycosylase activity domain for forming a polysaccharide chain from disaccharides. The class B HMW-PBPs have a transpeptidase activity domain. For example, as for *C. glutamicum*, PBP1a and PBP1b can be mentioned as the class A HMW-PBPs. As for *C. glutamicum*, FtsI, PBP2a, and PBP2b can be mentioned as the class B HMW-PBPs.

When the activity of a penicillin-binding protein is reduced in a coryneform bacterium, the secretory production amount of a heterologous protein is increased compared with that observed for a non-modified strain. Examples of a penicillin-binding protein, for example, include PBP1a, class B HMW-PBPs, and LMW-PBPs, specifically include PBP1a and class B HMW-PBPs, or more specifically include PBP1a.

The "property that if the activity thereof is reduced in a coryneform bacterium, the secretory production amount of a heterologous protein is increased compared with that observed for a non-modified strain" can refer to a property imparting an ability to produce a heterologous protein by secretory production in an amount larger than that observed for a non-modified strain such as wild-type strain or parent strain to a coryneform bacterium when the activity thereof is reduced in the coryneform bacterium. The expression "to produce a heterologous protein by secretory production in an amount larger than that observed for a non-modified strain" may mean, but is not particularly limited to, so long as the secretory production amount of the heterologous protein increases compared with that observed for a non-modified strain, for example, that the heterologous protein is produced by secretory production in an amount larger than that observed for a non-modified strain by 10% or more, 20% or more, 30% or more, 100% or more, in terms of the accumulation amount in the medium and/or the cell surface layer. In addition, the expression "to produce a heterologous protein by secretory production in an amount larger than that observed for a non-modified strain" may also mean that whereas the heterologous protein cannot be detected when a non-concentrated culture supernatant of a non-modified strain is applied to SDS-PAGE and stained with CBB, the heterologous protein can be detected when a non-concentrated culture supernatant of a modified strain is applied to SDS-PAGE and stained with CBB.

Whether a protein has a property that if the activity thereof is reduced in a coryneform bacterium, the secretory production amount of a heterologous protein is increased compared with that observed for a non-modified strain can be confirmed by modifying a coryneform bacterium so that the activity of the protein is reduced, quantifying the secretory production amount of the heterologous protein observed when the modified strain is cultured in a medium, and comparing the quantified amount with the secretory production amount of the heterologous protein observed when an un-modified strain is cultured in the medium.

The Cgl0278 gene coding for the PBP1a protein of the *C. glutamicum* ATCC 13032 corresponds to a sequence complementary to the sequence of the positions 294001 to 296388 in the genome sequence registered in the NCBI database as GenBank accession BA000036 (VERSION BA000036.3 GI: 42602314). Also, the PBP1a protein of the *C. glutamicum* ATCC 13032 is registered as GenBank accession NP_599531 (version NP_599531.1 GI: 19551529, locus_tag="NCgl0274"). The nucleotide sequence of the Cgl0278 gene of *C. glutamicum* ATCC 13032 and the amino acid sequence of the PBP1a protein encoded by this gene are shown as SEQ ID NOS: 99 and 100, respectively.

Since the nucleotide sequence of a gene coding for a penicillin-binding protein may differ depending on species or strain to which the coryneform bacterium belongs, the gene coding for a penicillin-binding protein may be a variant of the aforementioned nucleotide sequence, so long as it codes for a protein having a property that if the activity thereof is reduced in a coryneform bacterium, the secretory production amount of a heterologous protein is increased compared with that observed for a non-modified strain. For example, the gene coding for a penicillin-binding protein may be a gene coding for a protein having the aforementioned amino acid sequence including substitution, deletion, insertion, or addition of one or several amino acid residues at one or several positions, so long as the gene codes for a protein having a property that if the activity thereof is reduced in a coryneform bacterium, the secretory production amount of a heterologous protein is increased compared with that observed for a non-modified strain. The above descriptions concerning variants of the metallopeptidases and genes coding for them can be applied mutatis mutandis to variants of the penicillin-binding proteins and genes coding for them.

Hereafter, cell surface layer proteins and genes coding for them will be explained.

The cell surface layer proteins are present in the cell surface layers (S-layer) of bacteria and archaea. Examples of the cell surface layer proteins of coryneform bacteria include PS1 and PS2 (also referred to as CspB) of *C. glutamicum* and SlpA (also referred to as CspA) of *C. stationis*. Among them, it is preferred that the activity of PS2 protein is reduced.

The nucleotide sequence of the cspB gene of *C. glutamicum* ATCC 13869 and the amino acid sequence of the PS2 protein encoded by the gene are shown in SEQ ID NOS: 114 and 115, respectively.

Further, for example, amino acid sequences of CspB homologues were reported for 28 strains of *C. glutamicum* (J. Biotechnol., 112, 177-193 (2004)). These 28 strains of *C. glutamicum* and the GenBank accession numbers of the cspB gene homologues in NCBI database are exemplified below (the GenBank accession numbers are shown in the parentheses).

*C. glutamicum* ATCC 13058 (AY524990)
*C. glutamicum* ATCC 13744 (AY524991)
*C. glutamicum* ATCC 13745 (AY524992)
*C. glutamicum* ATCC 14017 (AY524993)
*C. glutamicum* ATCC 14020 (AY525009)
*C. glutamicum* ATCC 14067 (AY524994)
*C. glutamicum* ATCC 14068 (AY525010)
*C. glutamicum* ATCC 14747 (AY525011)
*C. glutamicum* ATCC 14751 (AY524995)
*C. glutamicum* ATCC 14752 (AY524996)
*C. glutamicum* ATCC 14915 (AY524997)
*C. glutamicum* ATCC 15243 (AY524998)
*C. glutamicum* ATCC 15354 (AY524999)
*C. glutamicum* ATCC 17965 (AY525000)
*C. glutamicum* ATCC 17966 (AY525001)
*C. glutamicum* ATCC 19223 (AY525002)
*C. glutamicum* ATCC 19240 (AY525012)
*C. glutamicum* ATCC 21341 (AY525003)
*C. glutamicum* ATCC 21645 (AY525004)
*C. glutamicum* ATCC 31808 (AY525013)
*C. glutamicum* ATCC 31830 (AY525007)
*C. glutamicum* ATCC 31832 (AY525008)
*C. glutamicum* LP-6 (AY525014)
*C. glutamicum* DSM20137 (AY525015)
*C. glutamicum* DSM20598 (AY525016)
*C. glutamicum* DSM46307 (AY525017)
*C. glutamicum* 22220 (AY525005)
*C. glutamicum* 22243 (AY525006)

Since the nucleotide sequence of a gene coding for a cell surface layer protein may differ depending on species or strain to which the coryneform bacterium belongs, the gene coding for a cell surface layer protein may be a variant of the aforementioned nucleotide sequence, so long as it codes for a protein having a property that if the activity thereof is reduced in a coryneform bacterium, the secretory production amount of a heterologous protein is increased compared with that observed for a non-modified strain. For example, the gene coding for a cell surface layer protein may be a gene coding for a protein having the aforementioned amino acid sequence including substitution, deletion, insertion, or addition of one or several amino acid residues at one or several positions, so long as the gene codes for a protein having a property that if the activity thereof is reduced in a coryneform bacterium, the secretory production amount of a heterologous protein is increased compared with that observed for a non-modified strain. The above descriptions concerning variants of the metallopeptidases and genes coding for them can be applied to variants of the cell surface layer proteins and genes coding for them.

The expression "activity of a cell surface layer protein is reduced" includes when a coryneform bacterium has been modified so that the activity of a cell surface layer protein is reduced and a case where the activity of a cell surface layer protein is inherently reduced in a coryneform bacterium. The "activity of a cell surface layer protein is inherently reduced in a coryneform bacterium" includes a case where a coryneform bacterium is inherently deficient in a cell surface layer protein. That is, examples of a coryneform bacterium in which the activity of a cell surface layer protein is reduced include a coryneform bacterium that is inherently deficient in a cell surface layer protein. Examples of the "case where a coryneform bacterium is inherently deficient in a cell surface layer protein" include a case where a coryneform bacterium is inherently deficient in the gene encoding a cell surface layer protein. The expression "a coryneform bacterium is inherently deficient in a cell surface layer protein" may mean that a coryneform bacterium is inherently deficient in one or more proteins selected from cell surface layer protein(s) found in other strain(s) of the species to which the coryneform bacterium belongs. For example, "*C. glutamicum* is inherently deficient in a cell surface layer protein" may mean that a *C. glutamicum* strain is inherently deficient in one or more proteins selected from cell surface layer protein(s) found in other *C. glutamicum* strain(s), i.e. for example, deficient in PS1 and/or PS2 (CspB). Examples of the coryneform bacterium that is inherently deficient in a cell surface layer protein include *C. glutamicum* ATCC 13032, which is inherently deficient in the cspB gene.

Hereafter, means for reducing the activity of a protein will be explained.

The expression "activity of a protein is reduced" can mean that the activity of the target protein is decreased compared with that of a non-modified strain such as a wild-type strain or parent strain, which includes a case where the activity completely disappears. Specifically, the expression "activity of a protein is reduced" can mean that the number of molecules of the protein per cell is reduced, and/or the function of each molecule of the protein is reduced compared with those of a non-modified strain. That is, the term "activity" regarding the expression "activity of a protein is reduced" can mean the transcription amount (the amount of mRNA) of a gene encoding the protein or the amount of the protein, as well as the catalytic activity of the protein. In addition, the case where "number of molecules of the protein per cell is reduced" can include a case where the protein does not exist at all. Further, the case where "function of each molecule of the protein is reduced" can include a case where function of each molecule of the protein completely disappears.

The modification for reducing the activity of a protein can be attained by, for example, reducing expression of a gene coding for the protein. "Reduction of gene expression" is also referred to as "attenuation of gene expression". The reduction of gene expression may be induced by, for example, reduction of transcription efficiency, reduction of translation efficiency, or a combination of these. Reduction of expression of a gene can be attained by modifying an expression control sequence of the gene such as a promoter and the Shine-Dalgarno (SD) sequence. When an expression control sequence is modified, preferably one nucleotide or more, more preferably two nucleotides or more, particularly preferably three nucleotides or more, of the expression control sequence are modified. Moreover, a part or all of the expression control sequence may be deleted. Reduction of gene expression can also be attained by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth.

The modification for reducing the activity of a protein can also be attained by, for example, disrupting the gene coding for the protein. Disruption of a gene can be attained by, for example, deleting a part or all of the coding region of the gene on a chromosome. Furthermore, the total gene including sequences upstream and downstream from the gene on a chromosome may be deleted. The region to be deleted may be any region such as an N-terminal region, an internal region, or a C-terminal region, so long as reduction of the activity of the protein is to be attained. Deletion of a longer region can usually more surely inactivate the gene. Further, it is preferred that the reading frames of the sequences upstream and downstream from the region to be deleted are not the same.

Disruption of a gene can also be attained by, for example, introduction of a mutation for an amino acid substitution (missense mutation), a stop codon (nonsense mutation), a frame shift mutation which adds or deletes one or two nucleotides into the coding region of the gene on a chromosome, or the like (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into the coding region of the gene on a chromosome. Site of the insertion may be at any region of the gene, and insertion of a longer region can usually more surely inactivate the gene. It is preferred that the reading frames of the sequences upstream and downstream from the insertion site are not the same. The other sequence is not particularly limited so long as a sequence that reduces or eliminates the activity of the encoded protein is chosen, and examples include, for example, a marker gene such as an antibiotic resistance gene, a gene useful for production of a heterologous protein, and so forth.

Such modification of a gene on a chromosome as described above can be attained by, for example, preparing a deficient type gene in which a partial sequence of the gene is deleted so that it cannot produce a protein that can normally function, and transforming a bacterium with a recombinant DNA containing the deficient type gene to cause homologous recombination between the deficient type gene and the gene on a chromosome and thereby substitute the deficient type gene for the gene on the chromosome. In such a case, if a marker gene selected according to the characteristics of the host such as auxotrophy is included in the recombinant DNA, the operation becomes easy. The protein encoded by the deficient type gene has a conformation different from that of a wild-type protein, even if it is produced, and thus the function thereof is reduced or eliminated. Such gene disruption based on gene substitution utilizing homologous recombination has been already established, and such methods include "Red driven integration" (Datsenko, K. A, and Wanner, B. L., Proc. Natl. Acad. Sci. USA, 97:6640-6645 (2000)), a method of using a linear DNA such as a method utilizing the Red driven integration in combination with an excision system derived from λ phage (Cho, E. H., Gumport, R. I., Gardner, J. F., J. Bacteriol., 184:5200-5203 (2002)), a method of using a plasmid containing a temperature sensitive replication origin, a method of using a plasmid capable of conjugative transfer, a method of using a suicide vector not having replication origin which functions in a host (U.S. Pat. No. 6,303,383, Japanese Patent Laid-open (Kokai) No. 05-007491), and so forth.

The modification for reducing the activity of a protein can also be attained by, for example, a mutagenesis treatment. Examples of the mutagenesis treatment include usual mutagenesis treatments such as irradiation of X-ray or ultraviolet radiation and mutagenesis treatment with a mutation agent such as N-methyl-N'-nitro-N-nitrosoguanidine (MNNG), ethyl methanesulfonate (EMS), and methyl methanesulfonate (MMS).

Reduction of the activity of a target protein can be confirmed by measuring the activity of the protein. Specifically, the activity of a protein is decreased to, for example, 50% or less, 20% or less, 10% or less, 5% or less, or even 0%, of that observed in a non-modified strain. In the case of a penicillin-binding protein, whether activity of the protein has been reduced can be confirmed by, for example, measuring the transpeptidase activity and/or the transglycosylase activity depending on the class to which the protein belongs. The transpeptidase activity and/or the transglycosylase activity can be measured by, for example, a method well known to those skilled in the art. Specifically, for example, the transpeptidase and transglycosylase activities of PBP1a can be measured by measuring the reaction of oligomerizing lipid II to glycan strands and forming peptide cross-links (Born P, et al., J Biol. Chem. 2006 Sep. 15; 281(37): 26985-93.). Specifically, activity of a protein is decreased to, for example, 50% or less, 20% or less, 10% or less, 5% or less, or even 0%, of that observed in a non-modified strain.

Reduction of expression of a target gene can be confirmed by confirming reduction of the transcription amount of the gene or reduction of the amount of the target protein expressed from the gene.

Reduction of the transcription amount of a target gene can be confirmed by comparing the amount of mRNA transcribed from the gene with that observed in a non-modified strain. Examples of the method for measuring the amount of mRNA include Northern hybridization, RT-PCR, and so forth (Molecular Cloning, Cold spring Harbor Laboratory Press, Cold Spring Harbor (USA), 2001). The amount of mRNA can be decreased to, for example, 50% or less, 20% or less, 10% or less, 5% or less, or 0%, of that observed in a non-modified strain.

Reduction of the amount of a target protein can be confirmed by Western blotting using antibodies (Molecular Cloning, Cold Spring Harbor Laboratory Press, Cold Spring Harbor (USA) 2001). The amount of the protein can be decreased to, for example, 50% or less, 20% or less, 10% or less, 5% or less, or 0%, of that observed in a non-modified strain.

Disruption of a target gene can be confirmed by determining the nucleotide sequence of a part or all of the gene, restriction enzyme map, full length of the gene, or the like depending on the means used for the disruption.

The methods mentioned above for reducing the activity of a protein can also be applied mutatis mutandis to arbitrary proteins and genes coding for them as well as for reducing the activity of a penicillin-binding protein and reducing the activity of a cell surface layer protein.

Hereafter, the "genetic construct for secretory expression of a multimeric protein" and introduction method therefor will be explained. This genetic construct is also referred to as "genetic construct used for the present invention".

It is known that a secretory protein is generally translated as a preprotein (also referred to as prepeptide) or a preproprotein (also referred to as prepropeptide), and then becomes a mature protein through processing. Specifically, a secretory protein is generally translated as a preprotein or prepeproprotein, then a signal peptide as the pre-moiety is cleaved with a protease (generally called signal peptidase), and the secretory protein is thereby converted into a mature protein or proprotein. As for the proprotein, the pro-moiety thereof is further cleaved by a protease, and the proprotein thereby becomes a mature protein. Therefore, a signal peptide is preferably used for the secretory production of a multimeric protein in the method of the present invention. In the present invention, a preprotein and a preproprotein of a secretory protein may be collectively referred to as "secretory protein precursor". The "signal peptide" (also referred to as "signal sequence") can refer to an amino acid sequence present at the N-terminus of a secretory protein precursor, and usually not present in a natural mature protein.

Although the genetic construct is not particularly limited so long as secretory production of a multimeric protein can be attained, it can include a promoter sequence that functions in a coryneform bacterium, a nucleic acid sequence coding for a signal peptide that functions in the coryneform bacterium, which is ligated downstream from the promoter sequence, and a nucleic acid sequence coding for a multimeric protein, which is ligated downstream from the nucleic acid sequence coding for the signal peptide. The nucleic acid sequence coding for a signal peptide may be ligated downstream from the promoter sequence so that the signal peptide is expressed under the control of the promoter. The nucleic acid sequence coding for the multimeric protein may be ligated downstream from the nucleic acid sequence coding for the signal peptide so that the multimeric protein is expressed as a fusion protein with the signal peptide. The genetic construct can also comprise a control sequence (operator, terminator, etc.) effective for expression of the multimeric protein gene in a coryneform bacterium at such an appropriate position that it can function.

The promoter is not particularly limited so long as a promoter that functions in a coryneform bacterium is chosen, and it may be a promoter derived from a coryneform bacterium, or a heterologous promoter. The "promoter that functions in a coryneform bacterium" can refer to a promoter that possesses promoter activity in a coryneform bacterium. Specific examples of the heterologous promoter include, for example, promoters derived from *E. coli* such as tac promoter, lac promoter, trp promoter, and araBAD promoter. Among these, potent promoters such as tac promoter are preferred, and inducible promoters such as araBAD promoter are also preferred.

Examples of the promoter derived from a coryneform bacterium can include, for example, promoters of the genes coding for the cell surface layer proteins PS1, PS2 (also referred to as CspB), and SlpA (also referred to as CspA), and promoters of various amino acid biosynthesis system genes. Specific examples of the promoters of various amino acid biosynthesis system genes can include, for example, promoters of the glutamate dehydrogenase gene of the glutamic acid biosynthesis system, the glutamine synthetase gene of the glutamine synthesis system, the aspartokinase gene of the lysine biosynthesis system, the homoserine dehydrogenase gene of the threonine biosynthesis system, the acetohydroxy acid synthetase gene of the isoleucine and valine biosynthesis system, 2-isopropylmalate synthetase gene of the leucine biosynthesis system, the glutamate kinase gene of the proline and arginine biosynthesis system, the phosphoribosyl-ATP pyrophosphorylase gene of the histidine biosynthesis system, the deoxyarabinoheptulonate phosphate (DAHP) synthetase gene of the aromatic amino acid biosynthesis systems such as those for tryptophan, tyrosine, and phenylalanine, the phosphoribosyl pyrophosphate (PRPP) amidotransferase gene of the nucleic acid biosynthesis systems such as those for inosinic acid and guanylic acid, the inosinic acid dehydrogenase gene, and the guanylic acid synthetase gene.

As the promoter, a high activity type of an existing promoter may be obtained by using various reporter genes, and used. For example, by making the −35 and −10 regions in a promoter region closer to a consensus sequence, the activity of the promoter can be enhanced (International Patent Publication WO00/18935). Examples of the method for evaluating strength of a promoter and strong promoters are described in the paper of Goldstein et al. (Prokaryotic promoters in biotechnology, Biotechnol. Annu. Rev., 1, 105-128 (1995)) and so forth. Further, it is known that substitution, insertion, or deletion of several nucleotides in a spacer region between the ribosome-binding site (RBS) and the start codon, especially in a sequence immediately upstream of the start codon (5'-UTR), significantly affects stability and translation efficiency of mRNA, and these sequences can also be modified.

The signal peptide is not particularly limited so long as a signal peptide that functions in a coryneform bacterium is chosen, and it may be a signal peptide derived from a coryneform bacterium, or it may be a heterologous signal peptide. The "signal peptide that functions in a coryneform bacterium" can refer to a peptide that when it is ligated to the N-terminus of an objective protein, allows the coryneform bacterium to secrete the protein. The signal peptide can be a signal peptide of a secretory protein of the coryneform bacterium as the host, or a signal peptide of a cell surface layer protein of the coryneform bacterium. Examples of the cell surface layer protein of coryneform bacteria include PS1 and PS2 (CspB) derived from *C. glutamicum* (Japanese Patent Laid-open (Kohyo) No. 6-502548), and SlpA (CspA) derived from *C. ammoniagenes* (*C. stationis*) (Japanese Patent Laid-open (Kokai) No. 10-108675). The amino acid sequence of the signal peptide of PS1 is shown in SEQ ID NO: 101, the amino acid sequence of the signal peptide of PS2 (CspB) is shown in SEQ ID NO: 102, and the amino acid sequence of the signal peptide of SlpA (CspA) is shown in SEQ ID NO: 103. Moreover, U.S. Pat. No. 4,965,197 describes that there are signal peptides for DNases derived from coryneform bacteria, and such signal peptides can also be used for the present invention.

Although signal peptides have a certain characteristic of sequence common over biological species, a signal peptide that exhibits a secretory function in a certain biological species does not necessarily exhibit a secretory function in another biological species. Therefore, when a heterologous signal peptide is used, a signal peptide that functions in a coryneform bacterium may be appropriately chosen. Whether a certain signal peptide functions in a coryneform bacterium can be confirmed by, for example, expressing the objective protein as a fusion protein with that signal peptide, and confirming whether the protein is secreted or not.

The signal peptide may include a part of the N-terminal amino acid sequence of the secretory protein from which the signal peptide is derived. The signal sequence is generally cleaved by a signal peptidase, when the translation product is secreted out of the cell. As a gene coding for a signal peptide, although a naturally occurring gene may be used as it is, it may be modified so that it has the optimal codons according to codon frequencies in the chosen host.

Examples of the multimeric protein to be produced by secretory production can include, for example, physiologically active proteins, receptor proteins, antigen proteins which can be used as vaccines, and enzymes, which are multimeric proteins. Examples of the physiologically active proteins can include, for example, growth factors, hormones, cytokines, and antibody-related molecules.

The antibody-related molecule can refer to a protein that includes a single domain or a combination of two or more domains, such as domains that constitute a complete antibody. Examples of the domains that constitute a complete antibody include VH, CH1, CH2, and CH3, which are domains of a heavy chain, and VL and CL, which are domains of a light chain. The antibody-related molecule may be a monomer protein or a multimeric protein so long as it includes the above-mentioned molecular species. In the case where the antibody-related molecule is a multimeric protein, the antibody-related molecule may be a homo-multimer consisting of a single kind of subunit, or may be a hetero-multimer consisting of two or more kinds of subunits. Specific examples of the antibody-related molecules can include, for example, complete antibodies, Fab, F(ab'), F(ab')$_2$, Fc, dimer consisting of the heavy chain (H chain) and the light chain (L chain), Fc-fusion proteins, the heavy chain (H chain), the light chain (L chain), single chain Fv (scFv), sc(Fv)$_2$, disulfide-linked Fv (sdFv), and diabody.

Examples of the antibody-related molecules that are multimeric proteins can include, for example, complete antibodies, Fab, F(ab'), F(ab')$_2$, Fc, dimer consisting of the heavy chain (H chain) and the light chain (L chain), Fc-fusion proteins, sc(Fv)$_2$, and diabody. Among these, Fab, F(ab')$_2$, and Fc-fusion proteins are preferred.

Fab (fragment, antigen binding) is a part of a complete antibody except for the Fc region of the H chain, and it is an antibody fragment consisting only of the antigen-binding region. Fab is a dimer consisting of one molecule of the Fab moiety of the H chain and one molecule of the L chain, and they are linked via a disulfide bond at the C-terminus. The complete antibody is a H2L2 tetramer, and is a huge molecule having a molecular weight of about 150 kDa. In contrast, Fab has a smaller molecular weight of about 50 kDa, and therefore it is considered that Fab shows superior permeability for objective tissues. Since Fab does not have the Fc region, it does not have the complement activity or crystallization ability. However, since Fab has an antigen-binding ability, it is mainly used for the purpose of neutralizing antigens. Fab attracts attention in recent years among the antibody drugs.

F(ab') is a part of a complete antibody except for the Fc' region of the H chain. F(ab') is a dimer consisting of one molecule of the F(ab') moiety of the H chain and one molecule of the L chain, and they are linked via a disulfide bond at the C-terminus. The remaining moiety of the H chain in F(ab') is longer than the remaining moiety of the H chain in Fab, and hence, the disulfide bond moiety linking the H chains remains. Therefore, two molecules of F(ab') can form F(ab')$_2$ with a disulfide bond. F(ab') and F(ab')$_2$ can also be used as antibody drugs like the Fab fragment.

Fc (fragment, crystallizable) is an antibody fragment consisting only of the Fc region, which is responsible for the complement activity or crystallization ability. A protein consisting of the Fc region of the H chain fused with another functional protein is called Fc fusion protein.

Specific examples of the growth factors that are multimeric proteins can include, for example, vascular endothelial growth factor (VEGF).

Specific examples of the hormones that are multimeric proteins can include, for example, insulin.

Specific examples of the cytokines that are multimeric proteins can include, for example, interleukin 5, interferon γ, and tumor necrosis factors (TNFs).

The growth factors, hormones, and cytokines may not be strictly distinguished from one another. For example, a physiologically active protein may be a protein such as a growth factor, hormone, or cytokine, or may be a protein that is classified in more than one of these.

The receptor proteins are not particularly limited, so long as they are multimeric proteins. A receptor protein may be, for example, a receptor protein for any of physiologically active proteins and other physiologically active substances. Examples of the other physiologically active substances can include, for example, neurotransmitters such as dopamine. Further, a receptor protein may be an orphan receptor of which the corresponding ligand is not known.

The antigen proteins which can be used as vaccines are not particularly limited, so long as they are multimeric proteins that can induce an immune response. An antigen protein can be appropriately selected depending on the intended object of the immune response.

Specific examples of the enzymes that are multimeric proteins can include, for example, reverse transcriptase.

Genes coding for these proteins can be modified according to the chosen host and to obtain a desired activity. For example, the genes coding for these proteins may be modified so that the proteins include addition, deletion, substitution, or the like of one or several amino acid residues. The above descriptions concerning variants of the metallopeptidases and the genes coding for them can also be applied mutatis mutandis to the multimeric protein to be produced by secretory production by the method of the present invention and the gene coding for it. Further, in the genes coding for these proteins, arbitrary codons may be replaced with equivalent codons. For example, in the genes coding for these proteins, codons may be optimized as required according to codon frequencies observed in the host.

The N-terminal region of the multimeric protein eventually obtained by the method of the present invention may be the same as that of the natural protein, or may not be the same as that of the natural protein. For example, the N-terminal region of the eventually obtained multimeric protein may be that of the natural protein including addition or deletion of one or several amino acid residues. Although the number of the "one or several" amino acid residues may differ depending on the full length or structure of the objective multimeric protein, specifically, it can be 1 to 20, 1 to 10, or 1 to 5.

Furthermore, the multimeric protein to be produced by secretory production may be a protein comprising a pro-structure moiety (proprotein). When the multimeric protein to be produced by secretory production is a proprotein, the multimeric protein to be eventually obtained may be the proprotein or may not be the proprotein. That is, the proprotein may be processed into the mature protein by cleavage of the pro-structure moiety. The cleavage can be attained with, for example, a protease. When a protease is used, generally, the proprotein is preferably cleaved at a position substantially the same as that of the natural protein, or more preferably at exactly the same position as that of the natural protein so that the same mature protein as the natural mature protein is obtained, in view of the activity of the eventually obtained protein. Therefore, generally, a specific protease that cleaves the proprotein at such a position that the same protein as the naturally occurring mature protein is generated is most preferred. However, the N-terminal region of the multimeric protein to be eventually obtained may not be the same as that of the natural protein as described above. For example, depending on type, purpose of use etc. of the multimeric protein to be produced, a protein having an N-terminus longer or shorter by one to several amino acid residues compared with the natural protein may have more appropriate activity. Proteases that can be used in the present invention can include, for example, commercially available proteases such as Dispase (produced by Boehringer Mannheim) as well as those obtainable from culture broth of a microorganism such as culture broth of actinomycetes. Such proteases may be used in an un-purified state, or may be used after purification to an appropriate purity as required.

The method for introducing the genetic construct into the coryneform bacterium is not particularly limited. In the bacterium of the present invention, the genetic construct may be present on a vector that autonomously replicates out of the chromosome such as a plasmid, or may be incorporated into the chromosome. In addition, as described above, for constructing the bacterium of the present invention, modifications such as the introduction of the genetic construct, impartation or enhancement of the ability to produce a protein by secretory production, increase of the expression of a gene coding for a metallopeptidase, reduction of the activity of a penicillin-binding protein, and reduction of the activity of a cell surface layer protein can be performed in an arbitrary order.

The genetic construct can be introduced into a host by using, for example, a vector including the genetic construct. The vector is not particularly limited so long as a vector autonomously replicable in a coryneform bacterium is chosen, and may be, for example, a vector derived from a bacterial plasmid, a vector derived from a yeast plasmid, a vector derived from a bacteriophage, cosmid, phagemid, or the like. As the vector, for example, a plasmid derived from a coryneform bacterium is preferred. Specific examples of vector autonomously replicable in coryneform bacteria include pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; pCG4 and pCG11 described in Japanese Patent Laid-open (Kokai) No. 57-183799; pVK7 described in Japanese Patent Laid-open (Kokai) No. 10-215883; pVC7 described in Japanese Patent Laid-open (Kokai) No. 9-070291; and so forth.

Further, an artificial transposon and so forth can also be used. When a transposon is used, a multimeric protein gene is introduced into a chromosome by homologous recombination or translocation ability of the transposon itself. Other examples of the introduction method utilizing homologous recombination include, for example, the methods utilizing a linear DNA, a plasmid having a temperature sensitive replication origin, a plasmid capable of conjugative transfer, a suicide vector not having a replication origin that functions in a host, and so forth. In addition, when a multimeric protein gene is introduced into a chromosome, so long as the genetic construct is present on the chromosome, either one or both of the promoter sequence and the nucleic acid sequence coding for a signal peptide present in the genetic construct may be native to the host chromosome. Specifically, for example, by using a promoter sequence native to the host chromosome and a nucleic acid sequence coding for a signal peptide native to the host chromosome and ligated downstream from the promoter sequence as they are, and replacing only the gene ligated downstream from the nucleic acid sequence coding for the signal peptide with a gene of an objective multimeric protein, the genetic construct used for the present invention can be present on the chromosome, and the bacterium of the present invention can be thereby constructed.

Furthermore, when two or more kinds of subunits are expressed, it is sufficient that the genetic constructs for secretory expression of the subunits are harbored by the bacterium of the present invention so that secretory expression of the objective multimeric protein can be attained. Specifically, for example, all the genetic constructs for secretory expression of the subunits may be carried by a single expression vector, or carried by the chromosome. Alternatively, the genetic constructs for secretory expression of the subunits may be separately carried by two or more expression vectors, or may be separately carried by one or more expression vectors and the chromosome. The "case where two or more kinds of subunits are expressed" refers to, for example, a case where two or more kinds of multimeric proteins are produced by secretory production, or a case where a hetero-multimeric protein is produced by secretory production.

The method for introducing the genetic construct used for the present invention into the coryneform bacterium is not particularly limited, and a generally used method, for example, the protoplast method (Gene, 39, 281-286 (1985)), the electroporation method (Bio/Technology, 7, 1067-1070 (1989)), and so forth can be used.

<2> Method for Producing Multimeric Protein of the Present Invention

The present invention provides a method for producing a multimeric protein by culturing the bacterium of the present invention, and collecting the multimeric protein produced by secretory production (henceforth referred to as the "method of the present invention" or "method for producing a multimeric protein of the present invention"). That is, by culturing the bacterium of the present invention obtained as described above to express a multimeric protein, a large amount of the multimeric protein secreted out of the cells is obtained.

The bacterium of the present invention can be cultured according to a usually used method and conditions. For example, the bacterium of the present invention can be cultured in a usual medium containing a carbon source, a nitrogen source, and inorganic ions. In order to obtain still higher proliferation, organic micronutrients such as vitamins and amino acids can also be added as required.

As the carbon source, carbohydrates such as glucose and sucrose, organic acids such as acetic acid, alcohols, and others can be used. As the nitrogen source, ammonia gas, aqueous ammonia, ammonium salts, and others can be used. As the inorganic ions, calcium ions, magnesium ions, phosphate ions, potassium ions, iron ions, and so forth are appropriately used as required. The culture is performed within appropriate ranges of pH 5.0 to 8.5 and 15 to 37° C. under aerobic conditions for 1 to 7 days. Further, the culture conditions for L-amino acid production by coryneform bacteria and other conditions described for the methods for producing a protein using a signal peptide of the Sec type or the Tat type can be used (refer to WO01/23591 and WO2005/103278). Further, when an inducible promoter is used for expression of the multimeric protein, culture may also be performed with adding a promoter-inducing agent to the medium. By culturing the bacterium of the present invention under such conditions, a large amount of the objective protein is produced in cells and efficiently secreted out of the cells. In addition, according to the method of the present invention, the produced multimeric protein is secreted out of the cells, and therefore a protein that is generally lethal if it is accumulated in a large amount in cells of microorganisms can also be continuously produced without lethal effect.

The protein secreted in the medium according to the method of the present invention can be separated and purified from the medium after the culture by a method well known to those skilled in the art. For example, after the cells are removed by centrifugation or the like, the protein can be separated and purified by a known appropriate method such as salting out, ethanol precipitation, ultrafiltration, gel filtration chromatography, ion exchange column chromatography, affinity chromatography, medium or high pressure liquid chromatography, reverse phase chromatography, and hydrophobic chromatography, or a combination of these. Further, in a certain case, culture or culture supernatant may be used as it is. The protein secreted in the cell surface layer according to the method of the present invention can also be separated and purified in the same manner as that for the case where the protein is secreted in the medium, after solubilizing it by a method well known to those skilled in the art such as elevation of salt concentration and use of a surfactant. Further, in a certain case, the protein secreted in the cell surface layer may be used as, for example, an immobilized enzyme, without solubilizing it.

Secretory production of the objective multimeric protein can be confirmed by performing SDS-PAGE for the culture supernatant and/or a fraction containing the cell surface layer as a sample, and confirming the molecular weights of the separated protein bands. Secretory production of the objective multimeric protein can also be confirmed by performing Western blotting using antibodies for the culture supernatant and/or a fraction containing the cell surface layer as a sample (Molecular Cloning, Cold spring Harbor Laboratory Press, Cold Spring Harbor (USA), 2001). Secretory production of the objective multimeric protein can also be confirmed by determining the N-terminal amino acid sequences of the constituents of the obtained objective multimeric protein using a protein sequencer. Further, secretory production of the objective multimeric protein can also be confirmed by determining mass of the constituents of the obtained objective multimeric protein using a mass spectrometer. Furthermore, when the objective multimeric protein is an enzyme or a protein having a certain measurable physiological activity, secretory production of the objective multimeric protein can be confirmed by measuring enzymatic activity or the physiological activity of the objective multimeric protein in the culture supernatant and/or a fraction containing the cell surface layer as a sample.

EXAMPLES

The present invention will be further specifically explained with reference to the following non-limiting examples.

Reference Example 1

Construction of *Corynebacterium glutamicum* Deficient in Penicillin-Binding Protein PBP1a (1) Construction of Vector pBSΔCgl0278 for Deleting Cgl0278 Gene Coding for PBP1a The genome sequence of *C. glutamicum* ATCC 13032 and the nucleotide sequence of the Cgl0278 gene coding for the penicillin-binding protein PBP1a thereof have already been determined (Genbank Accession No. BA000036, NCBI gene entry NCgl0274). With reference to this sequence, the primers shown in SEQ ID NOS: 26, 27, 28, and 29 were synthesized. By PCR using the chromosomal DNA of the *C. glutamicum* ATCC 13869 strain prepared in a conventional manner (method of Saito and Miura [Biochim. Biophys. Acta, 72, 619 (1963)]) as the template, and the primers of SEQ ID NOS: 26 and 27, and the primers of SEQ ID NOS: 28 and 29, about 1 kbp of 5' side upstream region and about 1 kbp of 3' side downstream region of Cgl0278 coding for PBP1a were amplified, respectively. Then, by PCR using both the amplified DNA fragments as the template and DNAs shown as SEQ ID NOS: 26 and 29 as the primers, a DNA fragment of about 2 kbp consisting of both the fragments fused together was obtained. In the primers of SEQ ID NOS: 26 and 29, recognition sequences for the restriction enzymes BamHI and XbaI were designed, respectively. For PCR, Pyrobest DNA Polymerase (produced by Takara Bio) was used, and the reaction conditions were according to the protocol recommended by the manufacturer. This DNA fragment was treated with the restriction enzymes BamHI and XbaI, and inserted into pBS4 described in WO2005/113744 at the BamHI-XbaI site to obtain a vector pBSΔCgl0278 for deleting the Cgl0278 gene. For the ligation reaction, DNA Ligation Kit Ver. 2.1 (produced by Takara Bio) was used, and the reaction conditions were according to the protocol recommended by the manufacturer.

(3) Construction of PBP1a-Deficient Strain

Then, the *C. glutamicum* YDK010 strain described in WO2004/029254 was transformed with the constructed pBS- ΔCgl0278. The *C. glutamicum* YDK010 strain is a cell surface layer protein PS2-deficient strain of *C. glutamicum* AJ12036 (FERM BP-734) (WO2004/029254). Strains were selected from the obtained transformants according to the methods described in WO2005/113744 and WO2006/057450 to obtain YDK010ΔPBP1a strain deficient in the Cgl0278 gene.

Example 1

Cloning of Metalloendopeptidase-Like Gene Cgl0858 Homologue Derived from *C. Glutamicum* ATCC 13869

The genomic sequence of *C. glutamicum* ATCC 13032 and the nucleotide sequence of the Cgl0858 gene coding for the metalloendopeptidase-like protein thereof have already been determined (Genbank Accession No. BA000036, NCBI gene entry NCgl0824). With reference to this sequence, the primers shown in SEQ ID NOS: 01 and 02 were synthesized. By PCR using the chromosomal DNA of the *C. glutamicum* ATCC 13869 strain prepared in a conventional manner (method of Saito and Miura [Biochim. Biophys. Acta, 72, 619 (1963)]) as the template, and the primers of SEQ ID NOS: 01 and 02, a region of about 1.1 kbp which includes a Cgl0858 homologue coding for a metalloendopeptidase-like protein was amplified. For PCR, Pyrobest DNA Polymerase (produced by Takara Bio) was used, and the reaction conditions were according to the protocol recommended by the manufacturer.

Then, the amplified DNA fragment of about 1.1 kbp was collected by agarose gel electrophoresis using Wizard (registered trademark) SV Gel and PCR Clean-Up System (Promega). The collected fragment was introduced into pVC7 (shuttle vector replicable in both *Escherichia coli* and coryneform bacteria described in Japanese Patent Laid-open (Kokai) No. 9-070291) at the SmaI site, and then the result was introduced into competent cells of *Escherichia coli* JM109 (Takara Bio) to obtain a strain harboring a plasmid in which the Cgl0858 homologue was cloned. The plasmid was collected from this strain, and designated as pVMEP1. The nucleotide sequencing of the fragment cloned in pVMEP1 was performed by using BigDye (registered trademark) Terminator v3.1 Cycle Sequencing Kit (Applied Biosystems) and 3130 Genetic Analyzer (Applied Biosystems). As a result of the nucleotide sequencing, it was revealed that the nucleotide sequence of the cloned Cgl0858 homologue of *C. glutamicum* ATCC 13869 partially differed from the nucleotide sequence of Cgl0858 of *C. glutamicum* ATCC 13032. The nucleotide sequence of the Cgl0858 homologue derived from *C. glutamicum* ATCC 13869 is shown in SEQ ID NO: 3, and the total encoded amino acid sequence is shown in SEQ ID NO: 4. FIG. 1 shows an alignment of the amino acid sequences of the protein encoded by Cgl0858 of *C. glutamicum* ATCC 13032 and the protein encoded by the Cgl0858 homologue of *C. glutamicum* ATCC 13869. The homology for the full length of the amino acid sequences between the protein encoded by Cgl0858 of *C. glutamicum* ATCC 13032 and the protein encoded by the Cgl0858 homologue of *C. glutamicum* ATCC 13869 was 97.9%. The preparation of the alignment and calculation of the homology were performed by using Genetyx_Version9 (Genetyx).

Example 2

Secretory Expression of Fab(H&L) Fragments of Antibody Trastuzumab Using *C. Glutamicum* with Enhanced Expression of Cgl0858 Homologue (1) Construction of Plasmids for Secretory Expression of H Chain Region of Fab Fragments of Antibody Trastuzumab The gene sequence for the variable region of the H chain of the breast carcinoma cell-specific antibody trastuzumab has already been determined (Genbank Accession No. AY513484). With reference to this sequence and the sequence for the non-variable region of the H chain of a general antibody and in consideration of the codon frequencies in *C. glutamicum*, DNAs shown in SEQ ID NOS: 30 to 63 were synthesized. By PCR using these DNAs as the template and the separately synthesized primer DNAs shown in SEQ ID NOS: 64 and 65, the region for the full length H chain of trastuzumab was amplified to obtain a DNA fragment of about 1.4 kbp shown in the ID NO: 66. The amino acid sequence of the H chain of the antibody trastuzumab encoded by DNA shown in SEQ ID NO: 66 is shown in SEQ ID NO: 104.

Then, by PCR using pPKSPTG1 described in WO01/23591 (pPKSPTG1 is a vector for secretory expression of protransglutaminase (transglutaminase having a pro-structure moiety), and includes the promoter derived from the PS2 gene of the *C. glutamicum* ATCC 13869 strain, a DNA coding for the signal peptide derived from SlpA of the *C. ammoniagenes* ATCC 6872 strain and expressibly ligated downstream from the promoter, and a protransglutaminase gene derived from *S. mobaraense* ligated so that the protransglutaminase is expressed as a fusion protein with the signal peptide) as the template and the primers shown in SEQ ID NOS: 67 and 68, a region that includes the aforementioned promoter region and the aforementioned signal peptide region was amplified to obtain a DNA fragment of about 0.7 kbp.

Then, by PCR using both the amplified DNA fragments (i.e. the fragment that includes the region for the full length H chain of trastuzumab and the fragment that includes the promoter region and the signal peptide region) as the template and DNAs shown in SEQ ID NO: 65 and 67 as the primers, a DNA fragment of about 2.0 kbp consisting of both the DNA fragments fused together was obtained.

Then, by PCR using this fusion DNA fragment as the template, and DNAs shown in SEQ ID NOS: 67 and 69, SEQ ID NOS: 67 and 70, SEQ ID NOS: 67 and 71, SEQ ID NOS: 67 and 72, SEQ ID NOS: 67 and 73, SEQ ID NOS: 67 and 74, and SEQ ID NOS: 67 and 75 as the primers, DNA fragments of about 1.4 kbp each were obtained. In the primer of SEQ ID NO: 67, the recognition sequence for the restriction enzyme KpnI was designed. In the primers of SEQ ID NOS: 69, 70, 71, 72, 73, 74, and 75, a stop codon and the recognition sequence for the restriction enzyme KpnI were designed. For PCR, Pyrobest DNA Polymerase (produced by Takara Bio) was used, and the reaction conditions were according to the protocol recommended by the manufacturer. These DNA fragments were treated with the restriction enzyme KpnI, and inserted into pPK4 described in Japanese Patent Laid-open (Kokai) No. 9-322774 at the KpnI site to obtain plasmids for secretory expression of the H chain region of the Fab moiety of trastuzumab, pPKStrast-FabH(1-223C), pPKStrast-FabH(1-228T), pPKStrast-FabH(1-229C), pPKStrast-FabH(1-230P), pPKStrast-FabH(1-231P), pPKStrast-FabH(1-232C), and pPKStrast-FabH(1-233P). Specifically, with these plasmids, the amino acid sequence of the H chain of trastuzumab from the first amino acid residue to 223rd, 228th, 229th, 230th, 231st, 232nd or 233rd amino acid residue can be expressed according to the numbers included in the plasmid names, respectively. As a result of the nucleotide sequencing of the inserted fragments, it was confirmed that the expected genes were constructed. The nucleotide sequencing was performed by using BigDye (registered trademark) Terminator v3.1 Cycle Sequencing Kit (Applied Biosystems) and 3130 Genetic Analyzer (Applied Biosystems).

(2) Construction of Plasmid for Secretory Expression of L Chain Region of Fab Fragment of Antibody Trastuzumab The gene sequence for the variable region of the L chain of the breast carcinoma cell-specific antibody trastuzumab has already determined (Genbank Accession No. AY513485). With reference to this sequence and the sequence of the non-variable region of the L chain of a general antibody and in consideration of the codon frequencies in *C. glutamicum*, DNAs shown in SEQ ID NOS: 76 to 91 were synthesized. By PCR using these DNAs as the template, and the separately synthesized DNAs shown in SEQ ID NOS: 92 and 93 as the primers, the region for the full length L chain of trastuzumab was amplified to obtain a DNA fragment of about 0.6 kbp shown in the SEQ ID NO: 94. The amino acid sequence of the L chain of the antibody trastuzumab encoded by DNA shown in SEQ ID NO: 94 is shown in SEQ ID NO: 105. Then, by PCR using pPKSPTG1 described in WO01/23591 (including the promoter region derived from the *C. glutamicum* ATCC 13869 strain and the region for the signal peptide derived from the *C. ammoniagenes* ATCC 6872 strain) as the template, and the primers shown in SEQ ID NO: 95 and 96, a region that includes the aforementioned promoter region and the aforementioned region for signal peptide was amplified to obtain a DNA fragment of about 0.7 kbp. Then, by PCR using both the amplified DNA fragments (i.e. the fragment that includes the region for the L chain of trastuzumab and the fragment including the promoter region and the region for signal peptide) as the template and DNAs shown in SEQ ID NOS: 95 and 97 as the primers, a DNA fragment of about 1.3 kbp consisting of both the DNA fragments fused together was obtained. In the primers of SEQ ID NOS: 95 and 97, the recognition sequence for the restriction enzyme BamHI was designed. For PCR, Pyrobest DNA Polymerase (produced by Takara Bio) was used, and the reaction conditions were according to the protocol recommended by the manufacturer. This fusion DNA fragment was treated with the restriction enzyme BamHI, and then inserted into pPK4 described in Japanese Patent Laid-open (Kokai) No. 9-322774 at the BamHI site to obtain a plasmid for secretory expression of the L chain region of the Fab moiety of trastuzumab, pPKStrast-FabL. As a result of the nucleotide sequencing of the inserted fragment, it was confirmed that the expected gene was constructed. The nucleotide sequencing was performed by using BigDye Terminator v3.1 Cycle Sequencing Kit (Applied Biosystems) and 3130 Genetic Analyzer (Applied Biosystems).

(3) Construction of Plasmids for Secretory Expression of Fab(H&L) Fragment of Antibody Trastuzumab DNA fragments of about 1.4 kb obtained by digesting the expression plasmids for the H chain region of the Fab fragment of antibody trastuzumab constructed in Example 2(1) with the restriction enzyme KpnI each were inserted into the expression plasmid for the L chain region of the Fab fragment of antibody trastuzumab constructed in Example 2(2), pPKStrast-FabL, at the KpnI site to obtain plasmids for coexpression of the H chain region and the L chain region of the Fab fragment of trastuzumab, pPKstrast-FabH(1-223C)+L, pPKStrast-FabH(1-228T)+L, pPKStrast-FabH(1-229C)+L, pPKStrast-FabH(1-230P)+L, pPKStrast-FabH(1-231P)+L, pPKStrast-FabH(1-232C)+L, and pPKStrast-FabH(1-233P)+L.

(4) Secretory Expression of Fab(H&L) Fragment of Antibody Trastuzumab Using *C. Glutamicum* with Enhanced Expression of Cgl0858 Homologue By using the expression plasmid pVMEP1 for Cgl0858 homologue constructed in Example 1, as well as the plasmids for secretory expression of Fab(H&L) fragment of the antibody trastuzumab constructed in Example 2(3), pPKStrast-FabH(1-223C)+L, pPKStrast-FabH(1-228T)+L, pPKStrast-FabH(1-229C)+L, pPKStrast-FabH(1-230P)+L, pPKStrast-FabH(1-231P)+L, pPKStrast-FabH(1-232C)+L, and pPKStrast-FabH(1-233P)+L, the *C. glutamicum* YDK010 strain described in WO2004/029254 was transformed. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate pentahydrate, 450 μg of thiamine hydrochloride, 450 μg of biotin, 0.15 g of DL-methionine, and 50 g of calcium carbonate made into a volume of 1 L with water, and adjusted to pH 7.0) containing 5 mg/l of chloramphenicol and 25 mg/l of kanamycin at 30° C. for 96 hours. After completion of the culture, the culture supernatant obtained by centrifuging each culture broth was subjected to non-reduced SDS-PAGE, and then staining was performed with SYPRO Orange (Invitrogen) to perform comparison of the secretion amounts of the Fab(H&L) fragments of the antibody trastuzumab. As a result, it was found that the secretion amount of the heterodimer Fab(H&L) fragment of the antibody trastuzumab was significantly increased for all the strains introduced with pVMEP1, compared with that observed for the control strains introduced with pVC7, when using any of the plasmids for secretory expression of the Fab(H&L) fragments of the antibody trastuzumab (FIG. 2).

Figure 3:
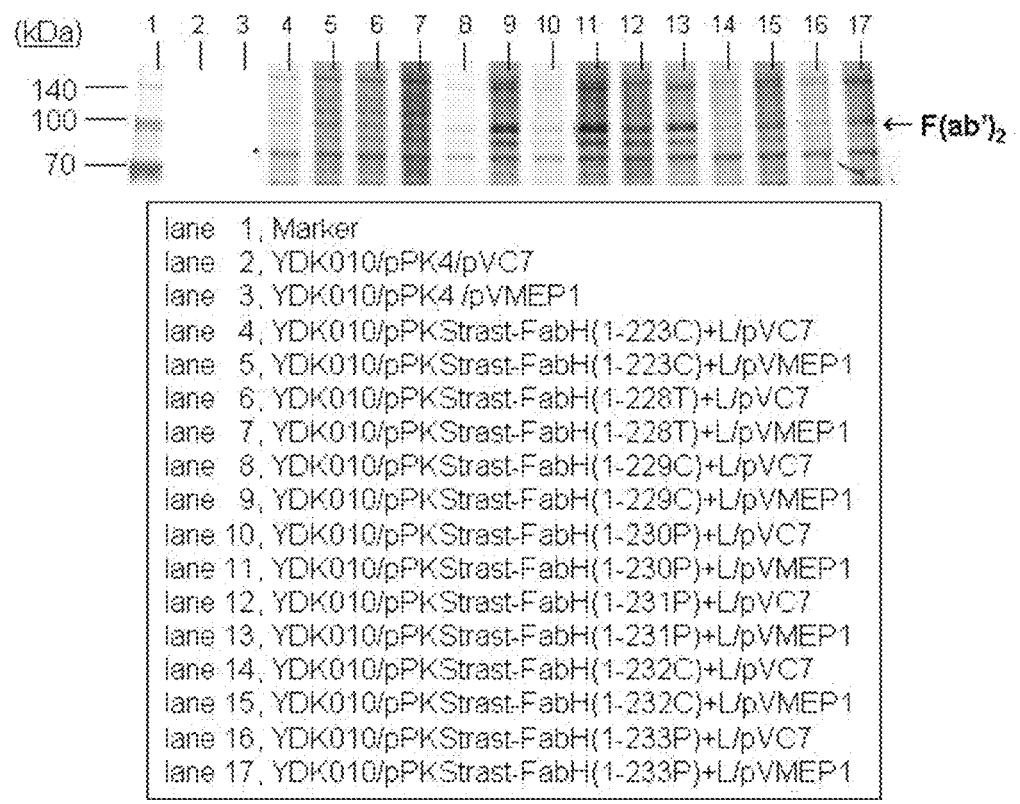
FIG. 3 is a photograph showing the results of Western blotting of the F(ab')$_2$ fragment of trastuzumab expressed in the *C. glutamicum* YDK010 strain and a metallopeptidase expression-enhanced strain thereof.

(5) Secretory Expression of Antibody Trastuzumab F(Ab')$_2$ Using *C. Glutamicum* with Enhanced Expression of Cgl0858 Homologue Each of the culture supernatants obtained in Example 2(4) was subjected to non-reduced SDS-PAGE, and then the proteins were transferred onto a PVDF membrane by using iBlot (registered trademark) Gel Transfer Stacks PVDF, Mini (Invitrogen) and iBlot (registered trademark) Gel Transfer System (Invitrogen). Western blotting was performed for this PVDF membrane by using alkaline phosphatase-labeled anti-human IgG[H&L] antibody (ROCKLAND) and Alkaline Phosphatase Conjugate Substrate Kit (Bio-Rad) to detect F(ab')$_2$ of the antibody trastuzumab. As a result, a protein band of the molecular weight of F(ab')$_2$ fragment of the antibody trastuzumab was detected for the culture supernatant of the transformant harboring each of pPKStrast-FabH(1-229C)+L, pPKStrast-FabH(1-230P)+L, pPKStrast-FabH(1-231P)+L, pPKStrast-FabH(1-232C)+L, and pPKStrast-FabH(1-233P)+L, which are plasmids for coexpression of the gene for the H chain region including a Cys residue which forms a disulfide bond linking the H chains, and the gene for the L chain. Further, the protein band of the molecular weight of the hetero-tetramer F(ab')$_2$ was significantly enhanced for all the strains introduced with pVMEP1, compared with that observed for the control strains introduced with pVC7, when using any of these plasmids for secretory expression (FIG. 3).

(6) Secretory Expression of Fab(H&L) Fragment of Antibody Trastuzumab Using *C. Glutamicum* with Enhanced Expression of Cgl0858 Homologue and Deficient in PBP1a By using the expression plasmid pVMEP1 for Cgl0858 homologue constructed in Example 1, as well as the plasmids for secretory expression of the Fab(H&L) fragment of antibody trastuzumab constructed in Example 2(3), pPKStrast-FabH(1-223C)+L, pPKStrast-FabH(1-228T)+L, pPKStrast-FabH(1-229C)+L, pPKStrast-FabH(1-230P)+L, pPKStrast-FabH(1-231P)+L, pPKStrast-FabH(1-232C)+L, and pPKStrast-FabH(1-233P)+L, the *C. glutamicum* YDK010ΔPBP1a strain constructed in Reference Example 1 was transformed. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate pentahydrate, 450 µg of thiamine hydrochloride, 450 µg of biotin, 0.15 g of DL-methionine, and 50 g of calcium carbonate made into a volume of 1 L with water, and adjusted to pH 7.0) containing 5 mg/l of chloramphenicol and 25 mg/l of kanamycin at 30° C. for 96 hours. After completion of the culture, each culture broth was centrifuged to obtain a culture supernatant.

Figure 4:
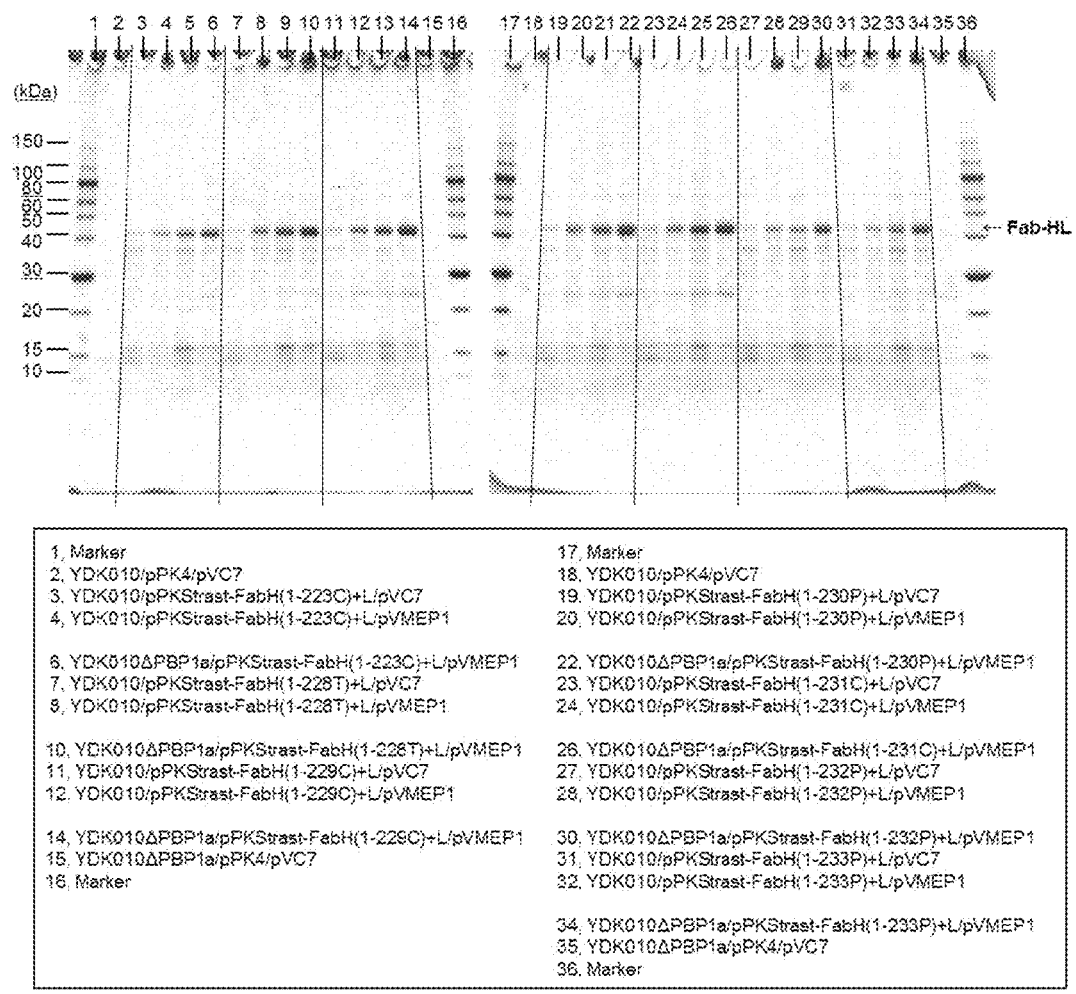
FIG. 4 is a photograph showing the results of non-reduced SDS-PAGE of the H chain region and the L chain region of the Fab fragment of trastuzumab coexpressed in the *C. glutamicum* YDK010 strain and a metallopeptidase expression-enhanced strain thereof, and a metallopeptidase expression-enhanced strain of the *C. glutamicum* YDK010ΔPBP1a strain.

Then, the culture supernatant samples obtained in Example 2(4) and Example 2(6) were subjected to non-reduced SDS-PAGE using the same gel, and then staining was performed with CBB-R250 (Bio-Rad) to perform comparison of the secretory production amounts of the Fab(H&L) fragment of the antibody trastuzumab. As a result, it was confirmed that the secretory production amount of the hetero-dimer Fab (H&L) fragment of the antibody trastuzumab further increased synergistically in the strains in which the enhanced expression of the Cgl0858 homologue was performed in combination with the deletion of PBP1a, compared with the strains in which the enhancement of the expression of the Cgl0858 homologue was performed solely (FIG. 4). Specifically, for the strains in which the only enhancement was the expression of the Cgl0858 homologue, SYPRO Orange showing high detection sensitivity was preferred for the detection of the bands, but for the strains in which the expression of the Cgl0858 homologue was enhanced in combination with the deletion of PBP1a, the expression amounts were at such a level that the bands could be easily detected by staining with CBB-R250, of which detection sensitivity is low.

Example 3

Secretory Expression of VEGF-A Using *Corynebacterium glutamicum* with Enhanced Expression of Cgl0858 Homologue (1) Construction of Plasmid for Secretory Expression of VEGF-A The sequence of the gene for the vascular endothelial growth factor A (VEGF-A) has already been determined (Genbank Accession No. NP_001165097). With reference to this sequence and in consideration of the codon frequencies in *C. glutamicum*, DNAs shown in SEQ ID NOS: 05 to 18 were synthesized. By PCR using these DNAs as the template and the separately synthesized DNAs shown in SEQ ID NOS: 19 and 20 as the primers, the full length of the VEGF-A gene sequence was amplified to obtain a DNA fragment of about 0.6 kbp shown in the ID NO: 21. Then, by PCR using this DNA fragment as the template and DNAs shown in SEQ ID NOS: 22 and 23 as the primers, the gene sequence for mature VEGF-A was amplified to obtain a DNA fragment of about 0.5 kbp. The amino acid sequence of the full length VEGF-A encoded by DNA shown in SEQ ID NO: 21 is shown in SEQ ID NO: 106, and the amino acid sequence of the mature VEGF-A is shown in SEQ ID NO: 107. Then, by PCR using pPKSPTG1 described in WO01/23591 (including the promoter region of CspB (PS2) derived from the *C. glutamicum* ATCC 13869 strain, and DNA coding for the signal peptide of CspA (SlpA) derived from the *C. ammoniagenes* ATCC 6872 strain) as the template and the primers shown in SEQ ID NOS: 24 and 25, the promoter region and the region for signal peptide were amplified to obtain a DNA fragment of about 0.7 kbp. Then, by PCR using both the amplified DNA fragments (i.e. the fragment of the mature VEGF gene sequence and the fragment of the promoter region and the region for signal peptide) as the template and DNAs shown in SEQ ID NO: 24 and 23 as the primers, a DNA fragment of about 1.2 kbp consisting of both the DNA fragments fused together was obtained. In the primers of SEQ ID NOS: 24 and 23, the recognition sequences for the restriction enzymes KpnI and XbaI were designed, respectively. For PCR, PrimeSTAR (registered trademark) HS DNA Polymerase (Takara Bio) was used, and the reaction conditions were according to the protocol recommended by the manufacturer. This fused DNA fragment was treated with the restriction enzymes KpnI and XbaI, and then inserted into pPK4 described in Japanese Patent Laid-open (Kokai) No. 9-322774 at the KpnI-XbaI site to obtain a plasmid pPKSVEGF for expression of VEGF-A. As a result of the nucleotide sequencing of the inserted fragment, it was confirmed that the expected gene was constructed. The nucleotide sequencing was performed by using BigDye Terminator v3.1 Cycle Sequencing Kit (Applied Biosystems) and 3130 Genetic Analyzer (Applied Biosystems).

Figure 5:
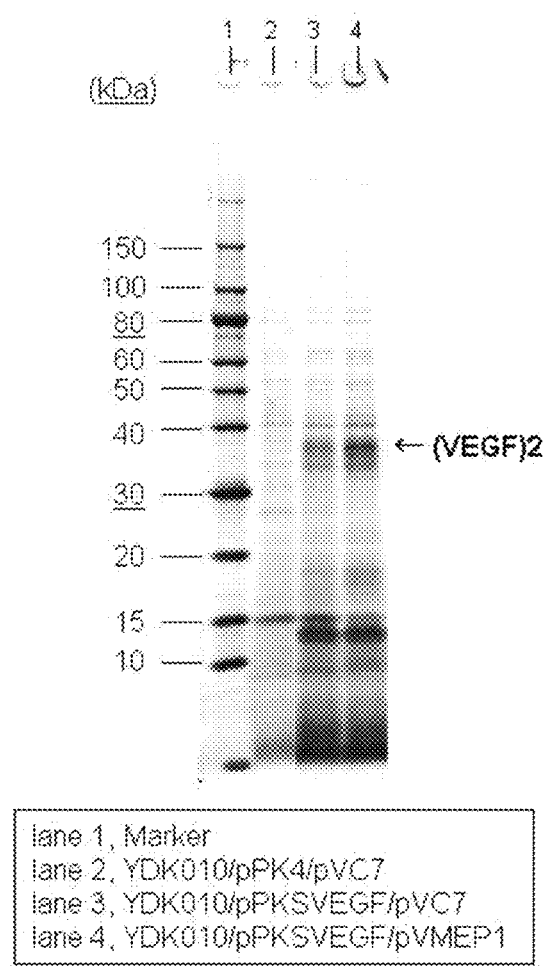
FIG. 5 is a photograph showing the results of non-reduced SDS-PAGE of the vascular endothelial cell growth factor A (VEGF-A) expressed in the *C. glutamicum* YDK010 strain and a metallopeptidase expression-enhanced strain thereof.

(2) Secretory Expression of VEGF-A Using *C. Glutamicum* with Enhanced Expression of Cgl0858 Homologue By using the expression plasmid pVMEP1 for Cgl0858 homologue constructed in Example 1(1) and the plasmid for secretory expression of VEGF-A, pPKSVEGF, constructed in Example 3(1), the *C. glutamicum* YDK010 strain described in WO2004/029254 was transformed. The obtained transformant was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate pentahydrate, 450 µg of thiamine hydrochloride, 450 µg of biotin, 0.15 g of DL-methionine, and 50 g of calcium carbonate made into a volume of 1 L with water, and adjusted to pH 7.0) containing 5 mg/l of chloramphenicol and 25 mg/l of kanamycin at 30° C. for 96 hours. After completion of the culture, the culture supernatant obtained by centrifuging each culture broth was subjected to non-reduced SDS-PAGE, and then staining was performed with SYPRO Orange (Invitrogen) to perform comparison of the secretion amounts of VEGF-A. As a result, the intensity of the protein band of the same molecular weight as that of the objective homodimer VEGF-A was observed for the strain introduced with pVMEP1, compared with that observed for the control strain introduced with pVC7 (FIG. 5). When the N-terminal sequence of this protein band was determined by using a protein sequencer PPSQ-21A (Shimadzu), it agreed with the N-terminal sequence of VEGF-A, and therefore secretory expression of the homodimer VEGF-A in the culture supernatant could be confirmed. As described above, the secretory production amount of the VEGF-A homodimer could be increased by increasing the expression of the Cgl0858 homologue.

Example 4

Secretory Expression of Fab(H&L) Fragment of Antibody Adalimumab Using *C. Glutamicum* with Enhanced Expression of Cgl0858 Homologue Construction of Plasmids for Secretory Expression of Fab (H&L) Fragments of Antibody Adalimumab The amino acid sequence of the tumor necrosis factor α (TNF-α)-specific antibody adalimumab has already been determined (The independent administrative agency, Pharmaceuticals and Medical Devices Agency, Examination report (Feb. 14, 2008)). With reference to this sequence, the total DNA fragment shown in SEQ ID NO: 108 was synthesized, including the promoter derived from the PS2 gene of the *C. glutamicum* ATCC 13869 strain, a DNA coding for the signal peptide derived from SlpA of the *C. stationis* ATCC 6872 strain expressibly ligated downstream from the promoter, and a DNA coding for the amino acid sequence of the 1st to 230th cysteine residue of the H chain of adalimumab ligated so that the amino acid sequence is expressed as a fusion protein with the signal peptide, and further including in the downstream thereof the promoter derived from the PS2 gene of the *C. glutamicum* ATCC 13869 strain, a DNA coding for the signal peptide derived from SlpA of the *C. stationis* ATCC 6872 strain expressibly ligated downstream from the promoter, and a DNA coding for the L chain of adalimumab ligated so that the L chain is expressed as a fusion protein with the signal peptide. Similarly, the total DNA fragment shown in SEQ ID NO: 109 was synthesized, including the promoter derived from the PS2 gene of the *C. glutamicum* ATCC 13869 strain, a DNA coding for the signal peptide derived from SlpA of the *C. stationis* ATCC 6872 strain expressibly ligated downstream from the promoter, and a DNA coding for the L chain of adalimumab ligated so that the L chain is expressed as a fusion protein with the signal peptide, and further including in the downstream thereof the promoter derived from the PS2 gene of the *C. glutamicum* ATCC 13869 strain, a DNA coding for the signal peptide derived from SlpA of the *C. stationis* ATCC 6872 strain expressibly ligated downstream from the promoter, and a DNA coding for the amino acid sequence of the 1st to 230th cysteine residue of the H chain of adalimumab ligated so that the amino acid sequence is expressed as a fusion protein with the signal peptide. The synthetic DNAs of SEQ ID NOS: 108 and 109 comprise the recognition sequence for the restriction enzyme BamHI at the 5' end and the recognition sequence for the restriction enzyme XbaI at the 3' end. In addition, the DNAs coding for the H chain and L chain of adalimumab comprised in the synthetic DNAs were designed in consideration of the codon frequencies in *C. glutamicum*. The DNA sequence coding for the amino acid sequence of the 1st to 230th cysteine residue of the H chain of adalimumab the 1st to the 230th amino acid residues of the H chain of adalimumab in the synthetic DNA is shown in SEQ ID NO: 110, and the amino acid sequence is shown in SEQ ID NO: 111. Further, the DNA sequence coding for the L chain of adalimumab in the synthetic DNA is shown in SEQ ID NO: 112, and the amino acid sequence of the L chain of adalimumab is shown in SEQ ID NO: 113. The synthesized total DNA fragments of about 2.7 kbp each were digested with the restriction enzymes BamHI and XbaI, and inserted into pPK4 described in Japanese Patent Laid-open (Kokai) No. 9-322774 at the BamHI-XbaI site to obtain plasmids for coexpression of the H chain (1-230C) and the L chain of the Fab fragment of the antibody adalimumab, pPK-Sada-FabHL and pPKSada-FabLH. "FabHL" and "FabLH" in the plasmid names indicate the carrying orders of the genes for the H chain and the L chain of adalimumab in the expression plasmids.

Figure 6:
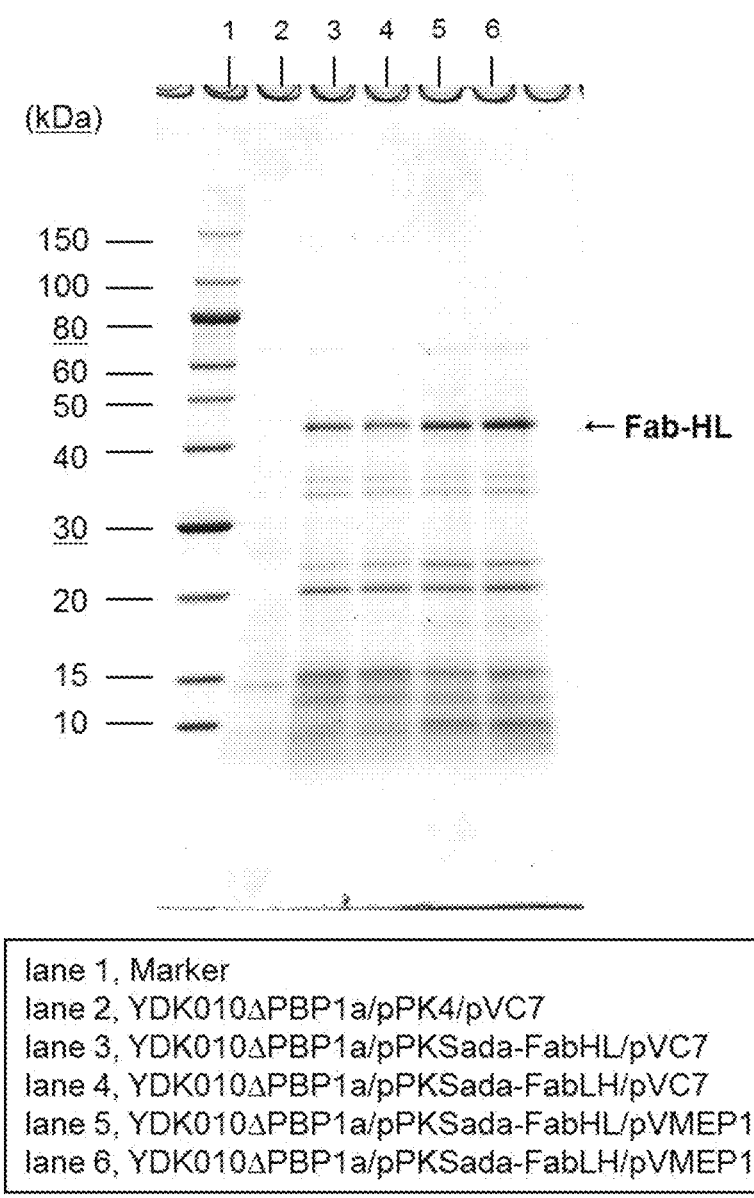
FIG. 6 is a photograph showing the results of non-reduced SDS-PAGE of the Fab(H&L) fragment of adalimumab expressed in the *C. glutamicum* YDK010ΔPBP1a strain and a metallopeptidase expression-enhanced strain thereof.

(2) Secretory Expression of Fab(H&L) Fragment of Antibody Adalimumab Using *C. Glutamicum* with Enhanced Expression of Cgl0858 Homologue By using the expression plasmid pVMEP1 for Cgl0858 homologue constructed in Example 1, as well as the plasmids for secretory expression of Fab(H&L) fragment of the antibody adalimumab constructed in Example 4(1), pPKSada-FabHL and pPKSada-FabLH, the YDK010ΔPBP1a strain constructed in Reference Example 1 was transformed. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate pentahydrate, 450 µg of thiamine hydrochloride, 450 µg of biotin, 0.15 g of DL-methionine, and 50 g of calcium carbonate made into a volume of 1 L with water, and adjusted to pH 7.0) containing 5 mg/l of chloramphenicol and 25 mg/l of kanamycin at 30° C. for 96 hours. After completion of the culture, the culture supernatant obtained by centrifuging each culture broth was subjected to non-reduced SDS-PAGE, and then staining was performed with CBB-R250 (Bio-Rad) to perform comparison of the secretory production amounts of the Fab(H&L) fragment of the antibody adalimumab. As a result, it was found that the secretion amount of the heterodimer Fab(H&L) fragment of the antibody adalimumab was significantly increased for both the strains introduced with pVMEP1, compared with that observed for the control strains introduced with pVC7, when using any of these plasmids for secretory expression (FIG. 6). On the basis of these results, it was revealed that the secretion amount of the antibody Fab(H&L) fragment is increased by enhancing expression of the Cgl0858 homologue not only in the case of expressing the Fab(H&L) fragment of trastuzumab, but also in the case of expressing the Fab(H&L) fragment of adalimumab.

Example 5

Figure 7:
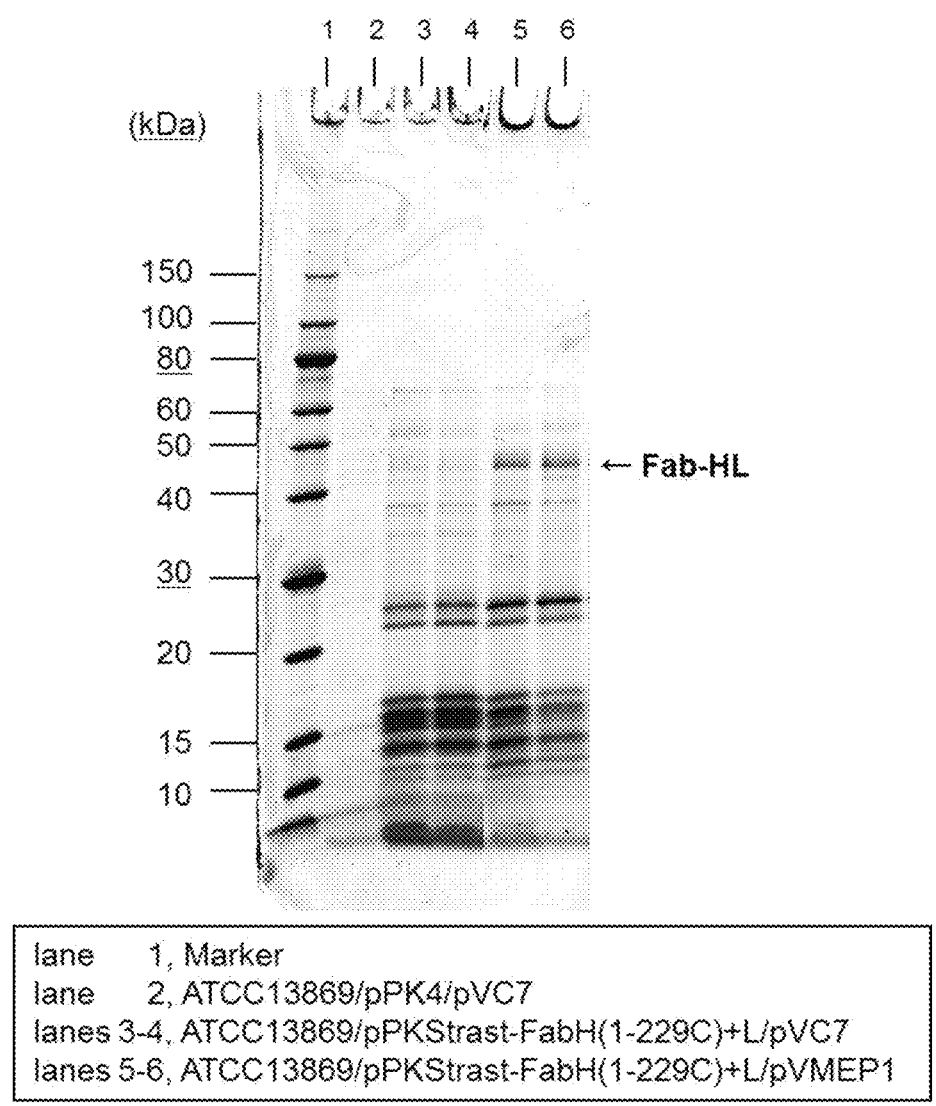
FIG. 7 is a photograph showing the results of non-reduced SDS-PAGE of the Fab(H&L) fragment of trastuzumab expressed in the *C. glutamicum* ATCC 13869 strain (wild-type strain) and a metallopeptidase expression-enhanced strain thereof.

Secretory Expression of Fab(H&L) Fragment of Antibody Trastuzumab in *C. Glutamicum* ATCC 13869 Strain with Enhanced Expression of Cgl0858 Homologue By using the expression plasmid pVMEP1 for Cgl0858 homologue constructed in Example 1, and the plasmid for secretory expression of the Fab(H&L) fragment of the antibody trastuzumab constructed in Example 2(3), pPKStrast-FabH(1-229C)+L, the *C. glutamicum* ATCC 13869 strain, which is the wild-type strain of the YDK010 strain (the cell surface layer protein PS2 (CspB)-deficient strain of *C. glutamicum* AJ12036 (FERM BP-734) (WO2004/029254)), was transformed. The obtained transformant was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate pentahydrate, 450 µg of thiamine hydrochloride, 450 µg of biotin, 0.15 g of DL-methionine, and 50 g of calcium carbonate made into a volume of 1 L with water, and adjusted to pH 7.0) containing 25 mg/l of kanamycin at 30° C. for 96 hours. After completion of the culture, the culture supernatant obtained by centrifuging each culture broth was subjected to non-reduced SDS-PAGE, and then staining was performed with SYPRO Orange (Invitrogen) to perform comparison of the secretion amounts of the Fab(H&L) fragment of the antibody trastuzumab. As a result, it was found that the secretion amount of the heterodimer Fab(H&L) fragment of the antibody trastuzumab was significantly increased for the strain introduced with pVMEP1 compared with that observed for the control strain introduced with pVC7 (FIG. 7). On the basis of this result, it was found that, even when the ATCC 13869 strain, which is a wild-type strain, was used as an expression host, the secretion amount of the antibody Fab(H&L) fragment was improved by enhancing the expression of the Cgl0858 homologue.

INDUSTRIAL APPLICABILITY

According to the present invention, a coryneform bacterium that can efficiently produce a multimeric protein by secretory production can be provided. Further, by using the coryneform bacterium provided by the present invention as an expression host, a multimeric protein such as industrially useful multimeric proteins can be efficiently produced by secretory production.

While the invention has been described in detail with reference to preferred embodiments thereof, it will be apparent to one skilled in the art that various changes can be made, an equivalents employed, without departing from the scope of the invention. Each of the aforementioned documents is incorporated by reference herein in its entirety.

EXPLANATION OF SEQUENCE LISTING

SEQ ID NOS: 1 and 2: Primers
SEQ ID NO: 3: Nucleotide sequence of Cgl0858 homologue of *C. glutamicum* ATCC 13869
SEQ ID NO: 4: Amino acid sequence of protein encoded by Cgl0858 homologue of *C. glutamicum* ATCC 13869
SEQ ID NOS: 5 to 18: Nucleotide sequences of DNAs for total synthesis of VEGF-A
SEQ ID NOS: 19 and 20: Primers
SEQ ID NO: 21: Nucleotide sequence of VEGF-A gene
SEQ ID NOS: 22 to 25: Primers
SEQ ID NOS: 26 to 29: Primers
SEQ ID NOS: 30 to 63: Nucleotide sequences of DNAs for total synthesis of H chain of trastuzumab
SEQ ID NOS: 64 and 65: Primers
SEQ ID NO: 66: Nucleotide sequence of trastuzumab H chain gene
SEQ ID NOS: 67 to 75: Primers
SEQ ID NOS: 76 to 91: Nucleotide sequences of DNAs for total synthesis of trastuzumab L chain
SEQ ID NOS: 92 and 93: Primers
SEQ ID NO: 94: Nucleotide sequence of trastuzumab L chain gene
SEQ ID NOS: 95 to 97: Primers
SEQ ID NO: 98: Amino acid sequence of protein encoded by Cgl0858 of *C. glutamicum* ATCC 13032
SEQ ID NO: 99: Nucleotide sequence of Cgl0278 of *C. glutamicum* ATCC 13032
SEQ ID NO: 100: Amino acid sequence of protein encoded by Cgl0278 of *C. glutamicum* ATCC 13032
SEQ ID NO: 101: Amino acid sequence of signal peptide of PS1 derived from *C. glutamicum*
SEQ ID NO: 102: Amino acid sequence of signal peptide of PS2 (CspB) derived from *C. glutamicum*
SEQ ID NO: 103: Amino acid sequence of signal peptide of SlpA (CspA) derived from *C. ammoniagenes*
SEQ ID NO: 104: Amino acid sequence of trastuzumab H chain
SEQ ID NO: 105: Amino acid sequence of trastuzumab L chain
SEQ ID NO: 106: Amino acid sequence of VEGF-A
SEQ ID NO: 107: Amino acid sequence of mature VEGF-A
SEQ ID NOS: 108 and 109: Nucleotide sequences of totally synthesized DNAs for expression of Fab(H&L) fragment of adalimumab
SEQ ID NO: 110: Nucleotide sequence of adalimumab H chain gene (1-230C coding region)
SEQ ID NO: 111: Amino acid sequence of adalimumab H chain (1-230C)
SEQ ID NO: 112: Nucleotide sequence of adalimumab L chain gene
SEQ ID NO: 113: Amino acid sequence of adalimumab L chain
SEQ ID NO: 114: Nucleotide sequence of cspB gene of *C. glutamicum* ATCC 13869
SEQ ID NO: 115: Amino acid sequence of protein encoded by cspB gene of *C. glutamicum* ATCC 13869

The invention claimed is:

1. A coryneform bacterium having an ability to produce a multimeric protein by secretory production, which is modified so that expression of a gene coding for a metallopeptidase is increased as compared with that in a non-modified strain, wherein the metallopeptidase is a protein selected from the group consisting of:
   (A) a protein comprising the amino acid sequence shown in SEQ ID NO: 4,
   (B) a protein comprising the amino acid sequence shown in SEQ ID NO: 4, but which includes substitution, deletion, insertion, or addition of 1 to 10 amino acid residues, and wherein said protein has a property that if activity thereof is increased in the coryneform bacterium, the secretory production amount of the multimeric protein is increased compared with that observed for a non-modified strain; and
   wherein the multimeric protein is an antibody-related molecule.

2. The coryneform bacterium according to claim 1, wherein the expression of the gene is increased by increasing copy number of the gene or by modifying an expression control sequence of the gene.

3. The coryneform bacterium according to claim 1, which is further modified so that the activity of a penicillin-binding protein is reduced as compared with that in a non-modified strain.

4. The coryneform bacterium according to claim 1, wherein the activity of a cell surface layer protein is reduced as compared with that in a non-modified strain.

5. The coryneform bacterium according to claim 1, which belongs to the genus *Corynebacterium* or *Brevibacterium*.

6. The coryneform bacterium according to claim 1, which is *Corynebacterium glutamicum*.

7. The coryneform bacterium according to claim 1, wherein the coryneform bacterium has a genetic construct for secretory expression of the multimeric protein, and wherein the genetic construct comprises a promoter sequence that functions in the coryneform bacterium, a nucleic acid sequence coding for a signal peptide that functions in the coryneform bacterium, which is ligated downstream from the promoter sequence, and a nucleic acid sequence coding for the multimeric protein, which is ligated downstream from the nucleic acid sequence coding for the signal peptide.

8. The coryneform bacterium according to claim 1, wherein the antibody-related molecule is selected from the group consisting of Fab, F(ab')$_2$, Fc fusion protein, and combinations thereof.

9. A method for producing a multimeric protein comprising:
   A) culturing the coryneform bacterium according to claim 1; and
   B) collecting the protein produced by secretory production.

* * * * *

```
                        SEQUENCE LISTING

<160> NUMBER OF SEQ ID NOS: 115

<210> SEQ ID NO 1
<211> LENGTH: 25
<212> TYPE: DNA
<213> ORGANISM: Artificial Sequence
<220> FEATURE:
<223> OTHER INFORMATION: primer

<400> SEQUENCE: 1
ctttgattgc cgagcttcct tctgt                                          25

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
ccgcaacggg tcgcccaaaa gttaa                                          25

<210> SEQ ID NO 3
<211> LENGTH: 714
<212> TYPE: DNA
<213> ORGANISM: Corynebacterium glutamicum ATCC13869

<400> SEQUENCE: 3
```

```
ttgcagaagc acactcgagg tggcaagcac cgcaagcaga ctacctcccc agtaactaag    60
ggtggtgtcg cttttgttgc agtagctacc ggtgccgtgt caactgcagg cgcaggcgga   120
gcagttgctc cacaggcttc caatcagccg gttgaggtca acttcgagct tactgcaaac   180
gacacaactg acctagtggc tggaagctcc gcccctcaga tcctgtctat cgctgagttc   240
aagccagttg tgaacttggg cgatcagatc gcaaagacca ttcagtacaa cgctgaccgc   300
attcaggctg acctggacgc tcgtggccct tcagtggttc gccctgctga aggttcttac   360
acttccggct tcggtgctcg ttgggcacc aaccacaatg gtgtggatat cgctaacgca   420
atcggcactc caatcctcgc tgccatggac ggcactgtta cgatgcagg tcctgcttcc   480 ggtttcggta actgggttcg cctccagcac gaagatggca ccatcaccgt gtacggccac   540
atggagactt tgaggttac tgttggtcag gttgtccgcg ctggagaccg catcgcaggc   600
atgggtaacc gaggattctc caccggctcc cacctccact cgaggtttta ccctgcgggc   660
ggcggcgctg tggatccagc tccttggctt gcagagcgtg gcattactct ttaa         714
```

<210> SEQ ID NO 4
<211> LENGTH: 237
<212> TYPE: PRT
<213> ORGANISM: Corynebacterium glutamicum ATCC13869

<400> SEQUENCE: 4

```
Met Gln Lys His Thr Arg Gly Gly Lys His Arg Lys Gln Thr Thr Ser
1               5                   10                  15

Pro Val Thr Lys Gly Gly Val Ala Phe Val Ala Val Ala Thr Gly Ala
            20                  25                  30

Val Ser Thr Ala Gly Ala Gly Gly Ala Val Ala Ala Gln Ala Ser Asn
        35                  40                  45

Gln Pro Val Glu Val Asn Phe Glu Leu Thr Ala Asn Asp Thr Thr Asp
    50                  55                  60

Leu Val Ala Gly Ser Ser Ala Pro Gln Ile Leu Ser Ile Ala Glu Phe
65                  70                  75                  80

Lys Pro Val Val Asn Leu Gly Asp Gln Ile Ala Lys Thr Ile Gln Tyr
                85                  90                  95

Asn Ala Asp Arg Ile Gln Ala Asp Leu Asp Ala Arg Gly Pro Ser Val
            100                 105                 110

Val Arg Pro Ala Glu Gly Ser Tyr Thr Ser Gly Phe Gly Ala Arg Trp
        115                 120                 125

Gly Thr Asn His Asn Gly Val Asp Ile Ala Asn Ala Ile Gly Thr Pro
    130                 135                 140

Ile Leu Ala Ala Met Asp Gly Thr Val Ile Asp Ala Gly Pro Ala Ser
145                 150                 155                 160

Gly Phe Gly Asn Trp Val Arg Leu Gln His Glu Asp Gly Thr Ile Thr
                165                 170                 175

Val Tyr Gly His Met Glu Thr Val Glu Val Thr Val Gly Gln Val Val
            180                 185                 190

Arg Ala Gly Asp Arg Ile Ala Gly Met Gly Asn Arg Gly Phe Ser Thr
        195                 200                 205

Gly Ser His Leu His Phe Glu Val Tyr Pro Ala Gly Gly Ala Val
    210                 215                 220

Asp Pro Ala Pro Trp Leu Ala Glu Arg Gly Ile Thr Leu
225                 230                 235
```

<210> SEQ ID NO 5

```
<211> LENGTH: 60
<212> TYPE: DNA
<213> ORGANISM: Artificial Sequence
<220> FEATURE:
<223> OTHER INFORMATION: VEGF-A

<400> SEQUENCE: 5
atgaacttcc tcctgtcctg ggtgcactgg tctttggctc tgctcctgta ccttcatcac    60

<210> SEQ ID NO 6
<211> LENGTH: 60
<212> TYPE: DNA
<213> ORGANISM: Artificial Sequence
<220> FEATURE:
<223> OTHER INFORMATION: VEGF-A

<400> SEQUENCE: 6
cgcctccttc ggccataggg gccgcttggg accacttcgc gtgatgaagg tacaggagca    60

<210> SEQ ID NO 7
<211> LENGTH: 60
<212> TYPE: DNA
<213> ORGANISM: Artificial Sequence
<220> FEATURE:
<223> OTHER INFORMATION: VEGF-A

<400> SEQUENCE: 7
ccctatggcc gaaggaggcg gccagaatca ccacgaagtg gtgaagttca tggatgttta    60

<210> SEQ ID NO 8
<211> LENGTH: 60
<212> TYPE: DNA
<213> ORGANISM: Artificial Sequence
<220> FEATURE:
<223> OTHER INFORMATION: VEGF-A

<400> SEQUENCE: 8
atcgacaagg gtttcgattg ggtggcagta ggagcgttgg taaacatcca tgaacttcac    60

<210> SEQ ID NO 9
<211> LENGTH: 60
<212> TYPE: DNA
<213> ORGANISM: Artificial Sequence
<220> FEATURE:
<223> OTHER INFORMATION: VEGF-A

<400> SEQUENCE: 9
caatcgaaac ccttgtcgat atctttcagg aatatcctga tgaaattgaa tacatcttta    60

<210> SEQ ID NO 10
<211> LENGTH: 60
<212> TYPE: DNA
<213> ORGANISM: Artificial Sequence
<220> FEATURE:
<223> OTHER INFORMATION: VEGF-A

<400> SEQUENCE: 10
caacaaccgc cacagcgcat gagcggcacg caggacggct aaagatgta ttcaatttca    60

<210> SEQ ID NO 11
<211> LENGTH: 60
<212> TYPE: DNA
<213> ORGANISM: Artificial Sequence
<220> FEATURE:
<223> OTHER INFORMATION: VEGF-A

<400> SEQUENCE: 11
```

```
atgcgctgtg gcggttgttg taacgatgaa ggtcttgagt gtgtgcctac cgaggaatct    60
```

<210> SEQ ID NO 12
<211> LENGTH: 60
<212> TYPE: DNA
<213> ORGANISM: Artificial Sequence
<220> FEATURE:
<223> OTHER INFORMATION: VEGF-A

<400> SEQUENCE: 12

```
cctgatgcgg cttaatgcgc ataatttgca tggtaatatt agattcctcg gtaggcacac    60
```

<210> SEQ ID NO 13
<211> LENGTH: 60
<212> TYPE: DNA
<213> ORGANISM: Artificial Sequence
<220> FEATURE:
<223> OTHER INFORMATION: VEGF-A

<400> SEQUENCE: 13

```
gcgcattaag ccgcatcagg gccagcacat cggcgaaatg tccttcttgc aacacaataa    60
```

<210> SEQ ID NO 14
<211> LENGTH: 60
<212> TYPE: DNA
<213> ORGANISM: Artificial Sequence
<220> FEATURE:
<223> OTHER INFORMATION: VEGF-A

<400> SEQUENCE: 14

```
ctcctggcgc gcgcgatcct tctttggccg gcactcgcat ttattgtgtt gcaagaagga    60
```

<210> SEQ ID NO 15
<211> LENGTH: 60
<212> TYPE: DNA
<213> ORGANISM: Artificial Sequence
<220> FEATURE:
<223> OTHER INFORMATION: VEGF-A

<400> SEQUENCE: 15

```
aggatcgcgc gcgccaggag aatccctgcg gtccctgctc cgagcgccgt aagcacctgt    60
```

<210> SEQ ID NO 16
<211> LENGTH: 60
<212> TYPE: DNA
<213> ORGANISM: Artificial Sequence
<220> FEATURE:
<223> OTHER INFORMATION: VEGF-A

<400> SEQUENCE: 16

```
tttttgcagc tgcacttaca ggtttgcggg tcctgcacaa acaggtgctt acggcgctcg    60
```

<210> SEQ ID NO 17
<211> LENGTH: 60
<212> TYPE: DNA
<213> ORGANISM: Artificial Sequence
<220> FEATURE:
<223> OTHER INFORMATION: VEGF-A

<400> SEQUENCE: 17

```
tgtaagtgca gctgcaaaaa cacggattcc cgctgcaaag cacgacaact ggaacttaac    60
```

<210> SEQ ID NO 18
<211> LENGTH: 56
<212> TYPE: DNA

<213> ORGANISM: Artificial Sequence
<220> FEATURE:
<223> OTHER INFORMATION: VEGF-A

<400> SEQUENCE: 18
tcaccggcgt ggtttatcgc aacggcacgt gcgctcgtta agttccagtt gtcgtg      56

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
atgaacttcc tcctgtcctg ggtg      24

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
tcaccggcgt ggtttatcgc aacg      24

<210> SEQ ID NO 21
<211> LENGTH: 576
<212> TYPE: DNA
<213> ORGANISM: Artificial Sequence
<220> FEATURE:
<223> OTHER INFORMATION: VEGF-A

<400> SEQUENCE: 21
atgaacttcc tcctgtcctg ggtgcactgg tctttggctc tgctcctgta ccttcatcac      60
gcgaagtggt cccaagcggc ccctatggcc gaaggaggcg ccagaatca ccacgaagtg      120 gtgaagttca tggatgttta ccaacgctcc tactgccacc caatcgaaac ccttgtcgat      180
atctttcagg aatatcctga tgaaattgaa tacatcttta gccgtcctg cgtgccgctc      240 atgcgctgtg gcggttgttg taacgatgaa ggtcttgagt gtgtgcctac cgaggaatct      300
aatattacca tgcaaattat gcgcattaag ccgcatcagg ccagcacat cggcgaaatg      360 tccttcttgc aacacaataa atgcgagtgc cggccaaaga aggatcgcgc gcgccaggag      420
aatccctgcg gtccctgctc cgagcgccgt aagcacctgt ttgtgcagga cccgcaaacc      480
tgtaagtgca gctgcaaaaa cacggattcc cgctgcaaag cacgacaact ggaacttaac      540
gagcgcacgt gccgttgcga taaaccacgc cggtga      576

<210> SEQ ID NO 22
<211> LENGTH: 36
<212> TYPE: DNA
<213> ORGANISM: Artificial Sequence
<220> FEATURE:
<223> OTHER INFORMATION: primer

<400> SEQUENCE: 22
gcacctgtgg caacggcagc ccctatggcc gaagga      36

<210> SEQ ID NO 23
<211> LENGTH: 40
<212> TYPE: DNA
<213> ORGANISM: Artificial Sequence

```
<220> FEATURE:
<223> OTHER INFORMATION: primer

<400> SEQUENCE: 23
gcaggtcgac tctagatcac cggcgtggtt tatcgcaacg                    40

<210> SEQ ID NO 24
<211> LENGTH: 44
<212> TYPE: DNA
<213> ORGANISM: Artificial Sequence
<220> FEATURE:
<223> OTHER INFORMATION: primer

<400> SEQUENCE: 24
acgaattcga gctcggtacc aaattcctgt gaattagctg attt               44

<210> SEQ ID NO 25
<211> LENGTH: 18
<212> TYPE: DNA
<213> ORGANISM: Artificial Sequence
<220> FEATURE:
<223> OTHER INFORMATION: primer

<400> SEQUENCE: 25
tgccgttgcc acaggtgc                                            18

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26
gtcggatccg cccccctgag ccaaatattc                               30

<210> SEQ ID NO 27
<211> LENGTH: 54
<212> TYPE: DNA
<213> ORGANISM: Artificial Sequence
<220> FEATURE:
<223> OTHER INFORMATION: primer

<400> SEQUENCE: 27
tttctagcgg aagaactggt tgatggcgtc gagctttgtc agagaattcg tggt    54

<210> SEQ ID NO 28
<211> LENGTH: 52
<212> TYPE: DNA
<213> ORGANISM: Artificial Sequence
<220> FEATURE:
<223> OTHER INFORMATION: primer

<400> SEQUENCE: 28
gtgtccacca cgaattctct gacaaagctc gacgccatca accagttctt cc      52

<210> SEQ ID NO 29
<211> LENGTH: 31
<212> TYPE: DNA
<213> ORGANISM: Artificial Sequence
<220> FEATURE:
<223> OTHER INFORMATION: primer

<400> SEQUENCE: 29
agtatctaga ttcgagtcgc ttttggttgg c                             31
```

<210> SEQ ID NO 30
<211> LENGTH: 60
<212> TYPE: DNA
<213> ORGANISM: Artificial Sequence
<220> FEATURE:
<223> OTHER INFORMATION: H chain

<400> SEQUENCE: 30
gaggttcaac tggtggagag cggcggcgga ctggttcaac caggcggcag cctccgcctg    60

<210> SEQ ID NO 31
<211> LENGTH: 60
<212> TYPE: DNA
<213> ORGANISM: Artificial Sequence
<220> FEATURE:
<223> OTHER INFORMATION: H chain

<400> SEQUENCE: 31
caacattaag gatacctaca tccattgggt tcgccaggca ccgggaaaag gattggaatg    60

<210> SEQ ID NO 32
<211> LENGTH: 60
<212> TYPE: DNA
<213> ORGANISM: Artificial Sequence
<220> FEATURE:
<223> OTHER INFORMATION: H chain

<400> SEQUENCE: 32
ctaatggcta cacccgctat gccgattccg ttaagggccg ctttaccatc tccgctgata    60

<210> SEQ ID NO 33
<211> LENGTH: 60
<212> TYPE: DNA
<213> ORGANISM: Artificial Sequence
<220> FEATURE:
<223> OTHER INFORMATION: H chain

<400> SEQUENCE: 33
ctgcaaatga actccttgcg cgcagaagac accgcagtgt actactgttc ccgctggggc    60

<210> SEQ ID NO 34
<211> LENGTH: 60
<212> TYPE: DNA
<213> ORGANISM: Artificial Sequence
<220> FEATURE:
<223> OTHER INFORMATION: H chain

<400> SEQUENCE: 34
ggattactgg ggccagggca ccctcgtcac ggtctccagc gctagcacca agggtccatc    60

<210> SEQ ID NO 35
<211> LENGTH: 60
<212> TYPE: DNA
<213> ORGANISM: Artificial Sequence
<220> FEATURE:
<223> OTHER INFORMATION: H chain

<400> SEQUENCE: 35
gcagcaagag cacctccggc ggcaccgcgg cactcggctg ccttgtgaaa gattacttcc    60

<210> SEQ ID NO 36
<211> LENGTH: 60
<212> TYPE: DNA
<213> ORGANISM: Artificial Sequence
<220> FEATURE:
<223> OTHER INFORMATION: H chain

```
<400> SEQUENCE: 36
tggaactccg gcgcccttac ctccggcgtt cataccttcc ccgcagtgct gcaatcctcc    60

<210> SEQ ID NO 37
<211> LENGTH: 60
<212> TYPE: DNA
<213> ORGANISM: Artificial Sequence
<220> FEATURE:
<223> OTHER INFORMATION: H chain

<400> SEQUENCE: 37
cgtcgtgacc gtcccgtcct cctccctggg cacccagacc tatatctgta acgtgaacca    60

<210> SEQ ID NO 38
<211> LENGTH: 60
<212> TYPE: DNA
<213> ORGANISM: Artificial Sequence
<220> FEATURE:
<223> OTHER INFORMATION: H chain

<400> SEQUENCE: 38
tcgataaaaa ggtggaacca aaatcctgtg ataaaactca cacctgccca ccgtgccccg    60

<210> SEQ ID NO 39
<211> LENGTH: 60
<212> TYPE: DNA
<213> ORGANISM: Artificial Sequence
<220> FEATURE:
<223> OTHER INFORMATION: H chain

<400> SEQUENCE: 39
ccgtccgtct tcttgttccc tccaaagccc aaagatacct tgatgatttc tcgcaccccg    60

<210> SEQ ID NO 40
<211> LENGTH: 60
<212> TYPE: DNA
<213> ORGANISM: Artificial Sequence
<220> FEATURE:
<223> OTHER INFORMATION: H chain

<400> SEQUENCE: 40
ggatgtgagc cacgaggacc ctgaagttaa gttcaactgg tacgttgatg gcgtggaagt    60

<210> SEQ ID NO 41
<211> LENGTH: 60
<212> TYPE: DNA
<213> ORGANISM: Artificial Sequence
<220> FEATURE:
<223> OTHER INFORMATION: H chain

<400> SEQUENCE: 41
cacgcgaaga acagtacaac tccacttatc gcgttgtctc tgtgctcacc gtcctgcacc    60

<210> SEQ ID NO 42
<211> LENGTH: 60
<212> TYPE: DNA
<213> ORGANISM: Artificial Sequence
<220> FEATURE:
<223> OTHER INFORMATION: H chain

<400> SEQUENCE: 42
gaatacaaat gcaaagtttc caacaaggct ctgccggcac cgattgagaa gaccatctcc    60

<210> SEQ ID NO 43
```

```
<211> LENGTH: 60
<212> TYPE: DNA
<213> ORGANISM: Artificial Sequence
<220> FEATURE:
<223> OTHER INFORMATION: H chain

<400> SEQUENCE: 43
cgaacctcaa gtgtacaccc ttcccccgtc tcgtgatgaa ttgacgaaga accaggtcag      60

<210> SEQ ID NO 44
<211> LENGTH: 60
<212> TYPE: DNA
<213> ORGANISM: Artificial Sequence
<220> FEATURE:
<223> OTHER INFORMATION: H chain

<400> SEQUENCE: 44
gtttttatcc ttccgatatt gcggtcgagt gggaatctaa cggccaaccc gaaacaatt      60

<210> SEQ ID NO 45
<211> LENGTH: 60
<212> TYPE: DNA
<213> ORGANISM: Artificial Sequence
<220> FEATURE:
<223> OTHER INFORMATION: H chain

<400> SEQUENCE: 45
ctggacagcg acggcagctt ctttctttac agcaaactga ccgtggataa atcccgctgg      60

<210> SEQ ID NO 46
<211> LENGTH: 60
<212> TYPE: DNA
<213> ORGANISM: Artificial Sequence
<220> FEATURE:
<223> OTHER INFORMATION: H chain

<400> SEQUENCE: 46
ctgcagcgtc atgcacgagg cactgcacaa ccactatacc cagaaatccc tctccctttc      60

<210> SEQ ID NO 47
<211> LENGTH: 33
<212> TYPE: DNA
<213> ORGANISM: Artificial Sequence
<220> FEATURE:
<223> OTHER INFORMATION: H chain

<400> SEQUENCE: 47
tcacttgcct ggggaaaggg agagggattt ctg                                  33

<210> SEQ ID NO 48
<211> LENGTH: 60
<212> TYPE: DNA
<213> ORGANISM: Artificial Sequence
<220> FEATURE:
<223> OTHER INFORMATION: H chain

<400> SEQUENCE: 48
cctcgtgcat gacgctgcag gaaaagacgt tgccctgctg ccagcgggat ttatccacgg      60

<210> SEQ ID NO 49
<211> LENGTH: 60
<212> TYPE: DNA
<213> ORGANISM: Artificial Sequence
<220> FEATURE:
<223> OTHER INFORMATION: H chain

<400> SEQUENCE: 49
```
aagctgccgt cgctgtccag cacaggcggg gtggtcttat aattgttttc gggttggccg    60

<210> SEQ ID NO 50
<211> LENGTH: 60
<212> TYPE: DNA
<213> ORGANISM: Artificial Sequence
<220> FEATURE:
<223> OTHER INFORMATION: H chain

<400> SEQUENCE: 50
aatatcggaa ggataaaaac ctttgaccag gcacgtgagg ctgacctggt tcttcgtcaa    60

<210> SEQ ID NO 51
<211> LENGTH: 60
<212> TYPE: DNA
<213> ORGANISM: Artificial Sequence
<220> FEATURE:
<223> OTHER INFORMATION: H chain

<400> SEQUENCE: 51
gggtgtacac ttgaggttcg cgaggctggc cttttgcctt ggagatggtc ttctcaatcg    60

<210> SEQ ID NO 52
<211> LENGTH: 60
<212> TYPE: DNA
<213> ORGANISM: Artificial Sequence
<220> FEATURE:
<223> OTHER INFORMATION: H chain

<400> SEQUENCE: 52
gaaactttgc atttgtattc tttaccgttc aaccaatctt ggtgcaggac ggtgagcaca    60

<210> SEQ ID NO 53
<211> LENGTH: 60
<212> TYPE: DNA
<213> ORGANISM: Artificial Sequence
<220> FEATURE:
<223> OTHER INFORMATION: H chain

<400> SEQUENCE: 53
gttgtactgt tcttcgcgtg gcttggtctt ggcattatga acttccacgc catcaacgta    60

<210> SEQ ID NO 54
<211> LENGTH: 60
<212> TYPE: DNA
<213> ORGANISM: Artificial Sequence
<220> FEATURE:
<223> OTHER INFORMATION: H chain

<400> SEQUENCE: 54
ggtcctcgtg gctcacatcc acgaccacgc aggtgacttc cggggtgcga gaaatcatca    60

<210> SEQ ID NO 55
<211> LENGTH: 60
<212> TYPE: DNA
<213> ORGANISM: Artificial Sequence
<220> FEATURE:
<223> OTHER INFORMATION: H chain

<400> SEQUENCE: 55
gggaacaaga agacggacgg acctccaaga agttcgggag cggggcacgg tgggcaggtg    60

<210> SEQ ID NO 56
<211> LENGTH: 60
<212> TYPE: DNA

<213> ORGANISM: Artificial Sequence
<220> FEATURE:
<223> OTHER INFORMATION: H chain

<400> SEQUENCE: 56
tggttccacc tttttatcga ccttggtgtt ggacggcttg tggttcacgt tacagatata    60

<210> SEQ ID NO 57
<211> LENGTH: 60
<212> TYPE: DNA
<213> ORGANISM: Artificial Sequence
<220> FEATURE:
<223> OTHER INFORMATION: H chain

<400> SEQUENCE: 57
aggacgggac ggtcacgacg gagctcaggg agtacagtcc ggaggattgc agcactgcgg    60

<210> SEQ ID NO 58
<211> LENGTH: 60
<212> TYPE: DNA
<213> ORGANISM: Artificial Sequence
<220> FEATURE:
<223> OTHER INFORMATION: H chain

<400> SEQUENCE: 58
gtaagggcgc cggagttcca gctcacagta actggttccg ggaagtaatc tttcacaagg    60

<210> SEQ ID NO 59
<211> LENGTH: 60
<212> TYPE: DNA
<213> ORGANISM: Artificial Sequence
<220> FEATURE:
<223> OTHER INFORMATION: H chain

<400> SEQUENCE: 59
gccggaggtg ctcttgctgc tcggcgccaa aggaaaaacg gatggaccct tggtgctagc    60

<210> SEQ ID NO 60
<211> LENGTH: 60
<212> TYPE: DNA
<213> ORGANISM: Artificial Sequence
<220> FEATURE:
<223> OTHER INFORMATION: H chain

<400> SEQUENCE: 60
tgccctggcc ccagtaatcc atagcgtaga agccgtcgcc gccccagcgg aacagtagt    60

<210> SEQ ID NO 61
<211> LENGTH: 60
<212> TYPE: DNA
<213> ORGANISM: Artificial Sequence
<220> FEATURE:
<223> OTHER INFORMATION: H chain

<400> SEQUENCE: 61
cgcaaggagt tcatttgcag gtatgcagtg tttttggagg tatcagcgga gatggtaaag    60

<210> SEQ ID NO 62
<211> LENGTH: 60
<212> TYPE: DNA
<213> ORGANISM: Artificial Sequence
<220> FEATURE:
<223> OTHER INFORMATION: H chain

<400> SEQUENCE: 62
atagcgggtg tagccattag tgggatagat acgcgccacc cattccaatc cttttcccgg    60

<210> SEQ ID NO 63
<211> LENGTH: 60
<212> TYPE: DNA
<213> ORGANISM: Artificial Sequence
<220> FEATURE:
<223> OTHER INFORMATION: H chain

<400> SEQUENCE: 63
tgtaggtatc cttaatgttg aatccggagg cggcacaaga caggcggagg ctgccgcctg    60

<210> SEQ ID NO 64
<211> LENGTH: 20
<212> TYPE: DNA
<213> ORGANISM: Artificial Sequence
<220> FEATURE:
<223> OTHER INFORMATION: primer

<400> SEQUENCE: 64
gaggttcaac tggtggagag                                                20

<210> SEQ ID NO 65
<211> LENGTH: 21
<212> TYPE: DNA
<213> ORGANISM: Artificial Sequence
<220> FEATURE:
<223> OTHER INFORMATION: primer

<400> SEQUENCE: 65
tcacttgcct ggggaaaggg g                                              21

<210> SEQ ID NO 66
<211> LENGTH: 1353
<212> TYPE: DNA
<213> ORGANISM: Artificial Sequence
<220> FEATURE:
<223> OTHER INFORMATION: H chain of Trastuzumab

<400> SEQUENCE: 66
gaggttcaac tggtggagag cggcggcgga ctggttcaac caggcggcag cctccgcctg    60
tcttgtgccg cctccggatt caacattaag gatacctaca tccattgggt tcgccaggca   120
ccgggaaaag gattgaatg gtggcgcgt atctatccca ctaatggcta cacccgctat    180
gccgattccg ttaagggccg ctttaccatc tccgctgata cctccaaaaa cactgcatac   240
ctgcaaatga actccttgcg cgcagaagac accgcagtgt actactgttc ccgctggggc   300
ggcgacggct tctacgctat ggattactgg ggccagggca cctcgtcac ggtctccagc    360 gctagcacca agggtccatc cgttttttcct ttggcgccga gcagcaagag cacctccggc   420
ggcaccgcgg cactcggctg ccttgtgaaa gattacttcc cggaaccagt tactgtgagc   480
tggaactccg gcgcccttac ctccggcgtt catacctcc ccgcagtgct gcaatcctcc    540
ggactgtact ccctgagctc cgtcgtgacc gtcccgtcct cctcccctggg cacccagacc   600 tatatctgta acgtgaacca caagccgtcc aacaccaagg tcgataaaaa ggtggaacca   660
aaatcctgtg ataaaactca cacctgccca ccgtgccccg ctcccgaact tcttggaggt    720
ccgtccgtct tcttgttccc tccaaagccc aaagatacct tgatgatttc tcgcaccccg   780
gaagtcacct gcgtggtcgt ggatgtgagc cacgaggacc ctgaagttaa gttcaactgg   840
tacgttgatg gcgtggaagt tcataatgcc aagaccaagc cacgcgaaga acagtacaac   900
tccacttatc gcgttgtctc tgtgctcacc gtcctgcacc aagattggtt gaacggtaaa   960

```
gaatacaaat gcaaagtttc caacaaggct ctgccggcac cgattgagaa gaccatctcc    1020
aaggcaaaag gccagcctcg cgaacctcaa gtgtacaccc ttcccccgtc tcgtgatgaa    1080
ttgacgaaga accaggtcag cctcacgtgc ctggtcaaag gtttttatcc ttccgatatt    1140
gcggtcgagt gggaatctaa cggccaaccc gaaaacaatt ataagaccac cccgcctgtg    1200
ctggacagcg acggcagctt ctttctttac agcaaactga ccgtggataa atcccgctgg    1260
cagcagggca acgtcttttc ctgcagcgtc atgcacgagg cactgcacaa ccactatacc    1320
cagaaatccc tctcccttc cccaggcaag tga                                  1353

<210> SEQ ID NO 67
<211> LENGTH: 30
<212> TYPE: DNA
<213> ORGANISM: Artificial Sequence
<220> FEATURE:
<223> OTHER INFORMATION: primer

<400> SEQUENCE: 67
gaattcgagc tcggtaccca aattcctgtg                                      30

<210> SEQ ID NO 68
<211> LENGTH: 40
<212> TYPE: DNA
<213> ORGANISM: Artificial Sequence
<220> FEATURE:
<223> OTHER INFORMATION: primer

<400> SEQUENCE: 68
ctctccacca gttgaacctc tgccgttgcc acaggtgcgg                            40

<210> SEQ ID NO 69
<211> LENGTH: 30
<212> TYPE: DNA
<213> ORGANISM: Artificial Sequence
<220> FEATURE:
<223> OTHER INFORMATION: primer

<400> SEQUENCE: 69
ggcaggtgtg ggtacctcaa caggattttg                                      30

<210> SEQ ID NO 70
<211> LENGTH: 30
<212> TYPE: DNA
<213> ORGANISM: Artificial Sequence
<220> FEATURE:
<223> OTHER INFORMATION: primer

<400> SEQUENCE: 70
gagcggggca ggtacctcag gtgtgagttt                                      30

<210> SEQ ID NO 71
<211> LENGTH: 30
<212> TYPE: DNA
<213> ORGANISM: Artificial Sequence
<220> FEATURE:
<223> OTHER INFORMATION: primer

<400> SEQUENCE: 71
cgggagcggg ggtacctcag caggtgtgag                                      30

<210> SEQ ID NO 72
<211> LENGTH: 30
<212> TYPE: DNA
<213> ORGANISM: Artificial Sequence
```

<220> FEATURE:
<223> OTHER INFORMATION: primer

<400> SEQUENCE: 72
gttcgggagc ggtacctcat gggcaggtgt                              30

<210> SEQ ID NO 73
<211> LENGTH: 30
<212> TYPE: DNA
<213> ORGANISM: Artificial Sequence
<220> FEATURE:
<223> OTHER INFORMATION: primer

<400> SEQUENCE: 73
gaagttcggg ggtacctcac ggtgggcagg                              30

<210> SEQ ID NO 74
<211> LENGTH: 30
<212> TYPE: DNA
<213> ORGANISM: Artificial Sequence
<220> FEATURE:
<223> OTHER INFORMATION: primer

<400> SEQUENCE: 74
caagaagttc ggtacctcag cacggtgggc                              30

<210> SEQ ID NO 75
<211> LENGTH: 30
<212> TYPE: DNA
<213> ORGANISM: Artificial Sequence
<220> FEATURE:
<223> OTHER INFORMATION: primer

<400> SEQUENCE: 75
ctccaagaag ggtacctcag gggcacggtg                              30

<210> SEQ ID NO 76
<211> LENGTH: 60
<212> TYPE: DNA
<213> ORGANISM: Artificial Sequence
<220> FEATURE:
<223> OTHER INFORMATION: L chain

<400> SEQUENCE: 76
gatattcaaa tgacccagag ccctccagc ctgtccgcaa gcgtcggcga ccgcgtcacc     60

<210> SEQ ID NO 77
<211> LENGTH: 60
<212> TYPE: DNA
<213> ORGANISM: Artificial Sequence
<220> FEATURE:
<223> OTHER INFORMATION: L chain

<400> SEQUENCE: 77
agacgttaat accgccgtgg catggtatca gcagaagcca ggcaaagcac caaagctgct     60

<210> SEQ ID NO 78
<211> LENGTH: 60
<212> TYPE: DNA
<213> ORGANISM: Artificial Sequence
<220> FEATURE:
<223> OTHER INFORMATION: L chain

<400> SEQUENCE: 78
tgtattccgg cgtcccctct cgcttttccg gttcccgctc cggcaccgac ttcactctta     60

<210> SEQ ID NO 79
<211> LENGTH: 60
<212> TYPE: DNA
<213> ORGANISM: Artificial Sequence
<220> FEATURE:
<223> OTHER INFORMATION: L chain

<400> SEQUENCE: 79
gaagacttcg ccacgtatta ctgccaacaa cactacacga ccccccgac cttcggacag        60

<210> SEQ ID NO 80
<211> LENGTH: 60
<212> TYPE: DNA
<213> ORGANISM: Artificial Sequence
<220> FEATURE:
<223> OTHER INFORMATION: L chain

<400> SEQUENCE: 80
gcgcaccgtc gccgcccct ccgtcttcat tttcccacca tctgacgaac agctgaaatc        60

<210> SEQ ID NO 81
<211> LENGTH: 60
<212> TYPE: DNA
<213> ORGANISM: Artificial Sequence
<220> FEATURE:
<223> OTHER INFORMATION: L chain

<400> SEQUENCE: 81
gcctgttgaa caacttttac ccccgcgagg caaaagtgca atggaaggtc gataacgcac        60

<210> SEQ ID NO 82
<211> LENGTH: 60
<212> TYPE: DNA
<213> ORGANISM: Artificial Sequence
<220> FEATURE:
<223> OTHER INFORMATION: L chain

<400> SEQUENCE: 82
gagtccgtga ccgaacagga ctccaaggat tctacctact ccctcagctc caccctcacc        60

<210> SEQ ID NO 83
<211> LENGTH: 60
<212> TYPE: DNA
<213> ORGANISM: Artificial Sequence
<220> FEATURE:
<223> OTHER INFORMATION: L chain

<400> SEQUENCE: 83
gaaacacaag gtctatgcct gcgaggtgac ccaccagggc ctttcctctc ccgtgaccaa        60

<210> SEQ ID NO 84
<211> LENGTH: 45
<212> TYPE: DNA
<213> ORGANISM: Artificial Sequence
<220> FEATURE:
<223> OTHER INFORMATION: L chain

<400> SEQUENCE: 84
tcagcattcg ccgcggttaa aggacttggt cacgggagag gaaag                       45

<210> SEQ ID NO 85
<211> LENGTH: 60
<212> TYPE: DNA
<213> ORGANISM: Artificial Sequence
<220> FEATURE:
<223> OTHER INFORMATION: L chain

<400> SEQUENCE: 85
aggcatagac cttgtgtttc tcgtagtccg ccttggagag ggtgagggtg gagctgaggg    60

<210> SEQ ID NO 86
<211> LENGTH: 60
<212> TYPE: DNA
<213> ORGANISM: Artificial Sequence
<220> FEATURE:
<223> OTHER INFORMATION: L chain

<400> SEQUENCE: 86
tcctgttcgg tcacggactc ttgggaatta ccggattgca gtgcgttatc gaccttccat    60

<210> SEQ ID NO 87
<211> LENGTH: 60
<212> TYPE: DNA
<213> ORGANISM: Artificial Sequence
<220> FEATURE:
<223> OTHER INFORMATION: L chain

<400> SEQUENCE: 87
gtaaaagttg ttcaacaggc acaccacaga agcagtaccg gatttcagct gttcgtcaga    60

<210> SEQ ID NO 88
<211> LENGTH: 60
<212> TYPE: DNA
<213> ORGANISM: Artificial Sequence
<220> FEATURE:
<223> OTHER INFORMATION: L chain

<400> SEQUENCE: 88 aggggcggc gacggtgcgc ttaatctcga ccttggtgcc ctgtccgaag gtcgggggg    60

<210> SEQ ID NO 89
<211> LENGTH: 60
<212> TYPE: DNA
<213> ORGANISM: Artificial Sequence
<220> FEATURE:
<223> OTHER INFORMATION: L chain

<400> SEQUENCE: 89
taatacgtgg cgaagtcttc tggttgcaag ctggagatgg taagagtgaa gtcggtgccg    60

<210> SEQ ID NO 90
<211> LENGTH: 60
<212> TYPE: DNA
<213> ORGANISM: Artificial Sequence
<220> FEATURE:
<223> OTHER INFORMATION: L chain

<400> SEQUENCE: 90 agagggacg ccggaataca agaaagaggc ggagtagatg agcagctttg gtgctttgcc    60

<210> SEQ ID NO 91
<211> LENGTH: 60
<212> TYPE: DNA
<213> ORGANISM: Artificial Sequence
<220> FEATURE:
<223> OTHER INFORMATION: L chain

<400> SEQUENCE: 91
ccacggcggt attaacgtct tggctggcgc ggcaagtaat ggtgacgcgg tcgccgacgc    60

<210> SEQ ID NO 92

<211> LENGTH: 20
<212> TYPE: DNA
<213> ORGANISM: Artificial Sequence
<220> FEATURE:
<223> OTHER INFORMATION: primer

<400> SEQUENCE: 92
gatattcaaa tgacccagag                                         20

<210> SEQ ID NO 93
<211> LENGTH: 20
<212> TYPE: DNA
<213> ORGANISM: Artificial Sequence
<220> FEATURE:
<223> OTHER INFORMATION: primer

<400> SEQUENCE: 93
tcagcattcg ccgcggttaa                                         20

<210> SEQ ID NO 94
<211> LENGTH: 645
<212> TYPE: DNA
<213> ORGANISM: Artificial Sequence
<220> FEATURE:
<223> OTHER INFORMATION: L chain of Trastuzumab

<400> SEQUENCE: 94
gatattcaaa tgacccagag cccctccagc ctgtccgcaa gcgtcggcga ccgcgtcacc    60
attacttgcc gcgccagcca agacgttaat accgccgtgg catggtatca gcagaagcca   120
ggcaaagcac caaagctgct catctactcc gcctctttct tgtattccgg cgtcccctct   180
cgcttttccg gttcccgctc cggcaccgac ttcactctta ccatctccag cttgcaacca   240
gaagacttcg ccacgtatta ctgccaacaa cactacacga ccccccccgac cttcggacag   300
ggcaccaagg tcgagattaa gcgcaccgtc gccgcccccct ccgtcttcat ttttcccacca   360
tctgacgaac agctgaaatc cggtactgct tctgtggtgt gcctgttgaa caactttttac   420
ccccgcgagg caaaagtgca atggaaggtc gataacgcac tgcaatccgg taattcccaa   480
gagtccgtga ccgaacagga ctccaaggat tctacctact ccctcagctc caccctcacc   540
ctctccaagg cggactacga gaaacacaag gtctatgcct gcgaggtgac ccaccagggc   600
ctttcctctc ccgtgaccaa gtcctttaac cgcggcgaat gctga              645

<210> SEQ ID NO 95
<211> LENGTH: 30
<212> TYPE: DNA
<213> ORGANISM: Artificial Sequence
<220> FEATURE:
<223> OTHER INFORMATION: primer

<400> SEQUENCE: 95
gaattcgagc tcggatccca aattcctgtg                               30

<210> SEQ ID NO 96
<211> LENGTH: 40
<212> TYPE: DNA
<213> ORGANISM: Artificial Sequence
<220> FEATURE:
<223> OTHER INFORMATION: primer

<400> SEQUENCE: 96
ctctgggtca tttgaatatc tgccgttgcc acaggtgcgg                    40

<210> SEQ ID NO 97
<211> LENGTH: 40
<212> TYPE: DNA
<213> ORGANISM: Artificial Sequence
<220> FEATURE:
<223> OTHER INFORMATION: primer

<400> SEQUENCE: 97
tcgtcgtcgt cgtcggatcc tcagcattcg ccgcggttaa          40

<210> SEQ ID NO 98
<211> LENGTH: 237
<212> TYPE: PRT
<213> ORGANISM: Corynebacterium glutamicum ATCC13032

<400> SEQUENCE: 98

Met Gln Lys His Thr Arg Gly Gly Lys His Arg Lys Gln Thr Thr Ser
1               5                   10                  15

Pro Val Thr Lys Gly Gly Val Ala Phe Val Ala Val Ala Thr Gly Ala
                20                  25                  30

Val Ser Thr Ala Gly Ala Gly Gly Ala Val Ala Ala Gln Ala Ser Asn
            35                  40                  45

Gln Pro Val Glu Val Asn Phe Glu Leu Thr Ala Asn Asp Thr Thr Asp
        50                  55                  60

Leu Val Ala Gly Ser Ser Ala Pro Gln Ile Leu Ser Ile Ala Glu Phe
65                  70                  75                  80

Lys Pro Val Val Asn Leu Gly Asp Gln Ile Val Lys Thr Ile Gln Tyr
                85                  90                  95

Asn Ala Asp Arg Ile Gln Ala Asp Leu Asp Ala Arg Gly Pro Ser Val
            100                 105                 110

Val Arg Pro Ala Glu Gly Ser Tyr Thr Ser Gly Phe Gly Ala Arg Trp
        115                 120                 125

Gly Thr Asn His Asn Gly Val Asp Ile Ala Asn Ala Ile Gly Thr Pro
    130                 135                 140

Ile Leu Ala Ala Met Asp Gly Thr Val Ile Asp Ala Gly Pro Ala Ser
145                 150                 155                 160

Gly Phe Gly Asn Trp Val Arg Leu Gln His Glu Asp Gly Thr Ile Thr
                165                 170                 175

Val Tyr Gly His Met Glu Thr Val Glu Val Thr Val Gly Gln Thr Val
            180                 185                 190

Lys Ala Gly Glu Arg Ile Ala Gly Met Gly Ser Arg Gly Phe Ser Thr
        195                 200                 205

Gly Ser His Leu His Phe Glu Val Tyr Pro Ala Gly Gly Gly Ala Val
    210                 215                 220

Asp Pro Ala Pro Trp Leu Ala Glu Arg Gly Ile Thr Leu
225                 230                 235

<210> SEQ ID NO 99
<211> LENGTH: 2388
<212> TYPE: DNA
<213> ORGANISM: Corynebacterium glutamicum ATCC13032

<400> SEQUENCE: 99
gtgtccacca cgaattctct gacaaagctc gttgcatcta cagtcgccgc tggcgtcctt          60
ggtgcgctcg cacttgtgcc tttcgctagt ctttctggcg ttgcggttgc gcgtaccaat         120
gacacgatgc agaccaacct ttcagatctg acgatggtc gcgggccggg cgtcacgacg          180
attactgatt ccactgacca gccgattgct tatatttatg cgcagcggcg gtttgaggtt         240

```
gggggtgatc agatttctac gtcgatgaag gatgcgatcg tttcgattga ggatcgcagg      300
ttctatgagc atgatggtgt ggatttgcag ggctttggtc gtgcaatcct gacgaacctg      360
gctgcgggtg gcgtggagca gggtgcttcg acgattaacc agcagtatgt gaagaacttc      420
ttgctgttgg tggaagctga tgatgaggcg agcaggctg ctgctgtgga aacctccatc       480
cctcgtaagc tccgtgagat gaagatggcg tctgatttgg aaaagacgtt gtcgaaggat      540
gagattctga ctcgttatct caacattgtt ccttttggta atggtgctta tggtgttgag      600
gctgcggcgc ggacgtattt cggtacgtcg gctgccgagt taaccattcc acagtctgcg      660
atgctcgcgg gcattgtgca gtcttcgtct tatctcaatc catacaccaa tcacgatgct      720
gtgtttgagc gtcgtaatac tgttttgggc gctatggctg atgctggcgc gatttcccca      780
gacgaggctt cggcttttcca gcaggaacct ttgggtgtcc tggaaacccc gcaaggctta    840
tccaatggtt gtatcggcgc tggcgatcgt ggtttcttct gcgattacgc tctgcaatat      900
ctttctgagc agggaatcac ccaagatatg ctggcgaagg actcctacac catcaaattg      960
actttggatc agatgttca ggatgcagcg cacaatgcgg tgtcctccca cgttgatcca      1020
accaccccag gtgtcgctga agttgtgaac gtcattgagc ctggcgagaa ctcccgcgat     1080
attttggcta ttacttcttc ccgcaactac ggccttgacc tggatgctgg tgaaacgatg     1140
ctgcctcagg caacgtcccg tgtgggtaat ggtgccggtt ccattttcaa gatctttacc     1200
gccgctgcag ccattcagca gggcgctggc ctagacacca tgttggatgt tccttctcga    1260
tatgaggtca agggcatggg ctccggcggt gccgcgaact gtcccgcaaa tacttactgc    1320
gtggaaaacg caggatccta cgcgcctcgc atgactctgc aggacgctct cgcgcagtcc    1380
cccaacactg cattcgttga aatgatcgag caggttggcg tggacaccgt tgtggatctt     1440
tcagtaaagc tgggcctgcg aagctacacc gatgaaggtt ccttcgacgg cgaaagctca     1500
atcgcggact acatgaagga caacaacctc ggttcttaca ctcttggacc taccgctgtt     1560
aaccctcttg aattgtccaa tgttgctgca accattgcat ccggtggcat gtggtgcgaa     1620
cccaatccca tcgccagcgt ccatgaccgt gaaggcaacg aagtctacat tgaccgccct     1680
gcatgtgagc gcgccatcga tgccgaaacg gcttcagctt tggccgtcgg catgagcaag     1740
gatacggtca gcggaactgc ggcctctgca gccagcatgt acggatggtc cttgccaacc     1800
gcagcgaaga ccggtaccac cgagtccaac cagtcctcag catttatggg cttcaacagc     1860
aactttgccg cagctccata catctacaat gacggcacct ccaccacccc actgtgcagc     1920
ggccccgtcc gccagtgcag cagcggtaac ctcttcggcg gtaacgaacc agctcaaaca     1980
tggtttaaca tggcaagcaa cgtccccgca gcttcgcaag gaacactgcc atccagcagc     2040
gattcattcc gcctcggcac ttccggcgaa ctcctcaacc aggttgtcgg ccaaagcgaa     2100
gcctccgctc gacgcaccct cgaagccaaa ggctacaagg tcaccacgcg ttcagtctcc     2160
ggcgccggca gcgcgcgcgg caccgtagtc agcgcaaccc ctcagggtgc agtgcttatc     2220
gacggtggaa ccgtcatttt ggacatctcc gacggcacaa gccctgcccc gctgccacc     2280
aacaatgatg acagcgacga tggagacacc cctgctccat caacaaacaa ccgcggaaca    2340
accattgaag acgccatcaa tgacgccatc aaccagttct ccgctag                   2388
```

<210> SEQ ID NO 100
<211> LENGTH: 795
<212> TYPE: PRT
<213> ORGANISM: Corynebacterium glutamicum ATCC13032

<400> SEQUENCE: 100

```
Met Ser Thr Thr Asn Ser Leu Thr Lys Leu Val Ala Ser Thr Val Ala
1               5                   10                  15

Ala Gly Val Leu Gly Ala Leu Ala Leu Val Pro Phe Ala Ser Leu Ser
            20                  25                  30

Gly Val Ala Val Ala Arg Thr Asn Asp Thr Met Gln Thr Asn Leu Ser
        35                  40                  45

Asp Leu Thr Asp Gly Arg Gly Pro Gly Val Thr Thr Ile Thr Asp Ser
    50                  55                  60

Thr Asp Gln Pro Ile Ala Tyr Ile Tyr Ala Gln Arg Arg Phe Glu Val
65                  70                  75                  80

Gly Gly Asp Gln Ile Ser Thr Ser Met Lys Asp Ala Ile Val Ser Ile
                85                  90                  95

Glu Asp Arg Arg Phe Tyr Glu His Asp Gly Val Asp Leu Gln Gly Phe
                100                 105                 110

Gly Arg Ala Ile Leu Thr Asn Leu Ala Ala Gly Gly Val Glu Gln Gly
            115                 120                 125

Ala Ser Thr Ile Asn Gln Gln Tyr Val Lys Asn Phe Leu Leu Leu Val
        130                 135                 140

Glu Ala Asp Asp Glu Ala Glu Gln Ala Ala Ala Val Glu Thr Ser Ile
145                 150                 155                 160

Pro Arg Lys Leu Arg Glu Met Lys Met Ala Ser Asp Leu Glu Lys Thr
                165                 170                 175

Leu Ser Lys Asp Glu Ile Leu Thr Arg Tyr Leu Asn Ile Val Pro Phe
            180                 185                 190

Gly Asn Gly Ala Tyr Gly Val Glu Ala Ala Arg Thr Tyr Phe Gly
        195                 200                 205

Thr Ser Ala Ala Glu Leu Thr Ile Pro Gln Ser Ala Met Leu Ala Gly
    210                 215                 220

Ile Val Gln Ser Ser Ser Tyr Leu Asn Pro Tyr Thr Asn His Asp Ala
225                 230                 235                 240

Val Phe Glu Arg Arg Asn Thr Val Leu Gly Ala Met Ala Asp Ala Gly
                245                 250                 255

Ala Ile Ser Pro Asp Glu Ala Ser Phe Gln Gln Glu Pro Leu Gly
            260                 265                 270

Val Leu Glu Thr Pro Gln Gly Leu Ser Asn Gly Cys Ile Gly Ala Gly
        275                 280                 285

Asp Arg Gly Phe Phe Cys Asp Tyr Ala Leu Gln Tyr Leu Ser Glu Gln
    290                 295                 300

Gly Ile Thr Gln Asp Met Leu Ala Lys Asp Ser Tyr Thr Ile Lys Leu
305                 310                 315                 320

Thr Leu Asp Pro Asp Val Gln Asp Ala Ala His Asn Ala Val Ser Ser
                325                 330                 335

His Val Asp Pro Thr Thr Pro Gly Val Ala Glu Val Asn Val Ile
            340                 345                 350

Glu Pro Gly Glu Asn Ser Arg Asp Ile Leu Ala Ile Thr Ser Ser Arg
        355                 360                 365

Asn Tyr Gly Leu Asp Leu Asp Ala Gly Glu Thr Met Leu Pro Gln Ala
    370                 375                 380

Thr Ser Arg Val Gly Asn Gly Ala Gly Ser Ile Phe Lys Ile Phe Thr
385                 390                 395                 400

Ala Ala Ala Ala Ile Gln Gln Gly Ala Gly Leu Asp Thr Met Leu Asp
                405                 410                 415
```

Val Pro Ser Arg Tyr Glu Val Lys Gly Met Gly Ser Gly Gly Ala Ala
420                     425                 430

Asn Cys Pro Ala Asn Thr Tyr Cys Val Glu Asn Ala Gly Ser Tyr Ala
            435                 440                 445

Pro Arg Met Thr Leu Gln Asp Ala Leu Ala Gln Ser Pro Asn Thr Ala
450                 455                 460

Phe Val Glu Met Ile Glu Gln Val Gly Val Asp Thr Val Asp Leu
465             470                 475                 480

Ser Val Lys Leu Gly Leu Arg Ser Tyr Thr Asp Gly Ser Phe Asp
                485                 490                 495

Gly Glu Ser Ser Ile Ala Asp Tyr Met Lys Asp Asn Leu Gly Ser
                500                 505                 510

Tyr Thr Leu Gly Pro Thr Ala Val Asn Pro Leu Glu Leu Ser Asn Val
            515                 520                 525

Ala Ala Thr Ile Ala Ser Gly Gly Met Trp Cys Glu Pro Asn Pro Ile
530                 535                 540

Ala Ser Val His Asp Arg Glu Gly Asn Glu Val Tyr Ile Asp Arg Pro
545                 550                 555                 560

Ala Cys Glu Arg Ala Ile Asp Ala Glu Thr Ala Ser Ala Leu Ala Val
            565                 570                 575

Gly Met Ser Lys Asp Thr Val Ser Gly Thr Ala Ser Ala Ala Ser
                580                 585                 590

Met Tyr Gly Trp Ser Leu Pro Thr Ala Ala Lys Thr Gly Thr Thr Glu
            595                 600                 605

Ser Asn Gln Ser Ser Ala Phe Met Gly Phe Asn Ser Asn Phe Ala Ala
610                 615                 620

Ala Pro Tyr Ile Tyr Asn Asp Gly Thr Ser Thr Thr Pro Leu Cys Ser
625                 630                 635                 640

Gly Pro Val Arg Gln Cys Ser Ser Gly Asn Leu Phe Gly Gly Asn Glu
                645                 650                 655

Pro Ala Gln Thr Trp Phe Asn Met Ala Ser Asn Val Pro Ala Ala Ser
            660                 665                 670

Gln Gly Thr Leu Pro Ser Ser Ser Asp Ser Phe Arg Leu Gly Thr Ser
            675                 680                 685

Gly Glu Leu Leu Asn Gln Val Val Gly Gln Ser Glu Ala Ser Ala Arg
690                 695                 700

Arg Thr Leu Glu Ala Lys Gly Tyr Lys Val Thr Thr Arg Ser Val Ser
705                 710                 715                 720

Gly Ala Gly Ser Ala Arg Gly Thr Val Val Ser Ala Thr Pro Gln Gly
                725                 730                 735

Ala Val Leu Ile Asp Gly Gly Thr Val Ile Leu Asp Ile Ser Asp Gly
            740                 745                 750

Thr Ser Pro Ala Pro Ala Ala Thr Asn Asn Asp Asp Ser Asp Asp Gly
            755                 760                 765

Asp Thr Pro Ala Pro Ser Thr Asn Asn Arg Gly Thr Thr Ile Glu Asp
            770                 775                 780

Ala Ile Asn Asp Ala Ile Asn Gln Phe Phe Arg
785                 790                 795

<210> SEQ ID NO 101
<211> LENGTH: 43
<212> TYPE: PRT
<213> ORGANISM: Corynebacterium glutamicum

<400> SEQUENCE: 101

Met Arg Asp Thr Ala Phe Arg Ser Ile Lys Ala Lys Ala Gln Ala Lys
1               5                   10                  15

Arg Arg Ser Leu Trp Ile Ala Ala Gly Ala Val Pro Thr Ala Ile Ala
            20                  25                  30

Leu Thr Met Ser Leu Ala Pro Met Ala Ser Ala
            35                  40

<210> SEQ ID NO 102
<211> LENGTH: 30
<212> TYPE: PRT
<213> ORGANISM: Corynebacterium glutamicum

<400> SEQUENCE: 102

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala
            20                  25                  30

<210> SEQ ID NO 103
<211> LENGTH: 25
<212> TYPE: PRT
<213> ORGANISM: Corynebacterium ammoniagenes

<400> SEQUENCE: 103

Met Lys Arg Met Lys Ser Leu Ala Ala Ala Leu Thr Val Ala Gly Ala
1               5                   10                  15

Met Leu Ala Ala Pro Val Ala Thr Ala
            20                  25

<210> SEQ ID NO 104
<211> LENGTH: 450
<212> TYPE: PRT
<213> ORGANISM: Artificial Sequence
<220> FEATURE:
<223> OTHER INFORMATION: H chain of Trastuzumab

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

```
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
        180                 185                 190
Ser Ser Ser Leu Gly Thr Gln Thr Tyr Ile Cys Asn Val Asn His Lys
    195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
        260                 265                 270
Asp Pro Glu Val Lys Phe Asn Trp Tyr Val Asp Gly Val Glu Val His
    275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
        340                 345                 350
Thr Leu Pro Pro Ser Arg Asp Glu Leu Thr Lys Asn Gln Val Ser Leu
    355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
        420                 425                 430
Glu Ala Leu His Asn His Tyr Thr Gln Lys Ser Leu Ser Leu Ser Pro
    435                 440                 445
Gly Lys
    450

<210> SEQ ID NO 105
<211> LENGTH: 214
<212> TYPE: PRT
<213> ORGANISM: Artificial Sequence
<220> FEATURE:
<223> OTHER INFORMATION: L chain of Trastuzumab

<400> SEQUENCE: 105

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
```

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 106
<211> LENGTH: 191
<212> TYPE: PRT
<213> ORGANISM: Homo sapiens

<400> SEQUENCE: 106

Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
                 20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
 50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

<210> SEQ ID NO 107
<211> LENGTH: 165
<212> TYPE: PRT
<213> ORGANISM: Homo sapiens
```

<400> SEQUENCE: 107

| Ala | Pro | Met | Ala | Glu | Gly | Gly | Gln | Asn | His | His | Glu | Val | Val | Lys |
|---|---|---|---|---|---|---|---|---|---|---|---|---|---|---|
| 1 | | | | 5 | | | | | 10 | | | | | 15 |

| Phe | Met | Asp | Val | Tyr | Gln | Arg | Ser | Tyr | Cys | His | Pro | Ile | Glu | Thr | Leu |
|---|---|---|---|---|---|---|---|---|---|---|---|---|---|---|---|
| | | | 20 | | | | | 25 | | | | | 30 | | |

| Val | Asp | Ile | Phe | Gln | Glu | Tyr | Pro | Asp | Glu | Ile | Glu | Tyr | Ile | Phe | Lys |
|---|---|---|---|---|---|---|---|---|---|---|---|---|---|---|---|
| | | 35 | | | | | 40 | | | | | 45 | | | |

| Pro | Ser | Cys | Val | Pro | Leu | Met | Arg | Cys | Gly | Gly | Cys | Cys | Asn | Asp | Glu |
|---|---|---|---|---|---|---|---|---|---|---|---|---|---|---|---|
| | 50 | | | | | 55 | | | | | 60 | | | | |

| Gly | Leu | Glu | Cys | Val | Pro | Thr | Glu | Glu | Ser | Asn | Ile | Thr | Met | Gln | Ile |
|---|---|---|---|---|---|---|---|---|---|---|---|---|---|---|---|
| 65 | | | | | 70 | | | | | 75 | | | | | 80 |

| Met | Arg | Ile | Lys | Pro | His | Gln | Gly | Gln | His | Ile | Gly | Glu | Met | Ser | Phe |
|---|---|---|---|---|---|---|---|---|---|---|---|---|---|---|---|
| | | | | 85 | | | | | 90 | | | | | 95 | |

| Leu | Gln | His | Asn | Lys | Cys | Glu | Cys | Arg | Pro | Lys | Lys | Asp | Arg | Ala | Arg |
|---|---|---|---|---|---|---|---|---|---|---|---|---|---|---|---|
| | | | 100 | | | | | 105 | | | | | 110 | | |

| Gln | Glu | Asn | Pro | Cys | Gly | Pro | Cys | Ser | Glu | Arg | Arg | Lys | His | Leu | Phe |
|---|---|---|---|---|---|---|---|---|---|---|---|---|---|---|---|
| | | 115 | | | | | 120 | | | | | 125 | | | |

| Val | Gln | Asp | Pro | Gln | Thr | Cys | Lys | Cys | Ser | Cys | Lys | Asn | Thr | Asp | Ser |
|---|---|---|---|---|---|---|---|---|---|---|---|---|---|---|---|
| | 130 | | | | | 135 | | | | | 140 | | | | |

| Arg | Cys | Lys | Ala | Arg | Gln | Leu | Glu | Leu | Asn | Glu | Arg | Thr | Cys | Arg | Cys |
|---|---|---|---|---|---|---|---|---|---|---|---|---|---|---|---|
| 145 | | | | | 150 | | | | | 155 | | | | | 160 |

| Asp | Lys | Pro | Arg | Arg |
|---|---|---|---|---|
| | | | | 165 |

<210> SEQ ID NO 108
<211> LENGTH: 2658
<212> TYPE: DNA
<213> ORGANISM: Artificial Sequence
<220> FEATURE:
<223> OTHER INFORMATION: synthesized DNA

<400> SEQUENCE: 108

```
ggatcccaaa ttcctgtgaa gtagctgatt tagtactttt cggaggtgtc tattcttacc      60
aaatcgtcaa gttgtgggta gagtcacctg aatattaatt gcaccgcacg ggtgatatat     120
gcttatttgc tcaagtagtt cgaggttaag tgtatttag gtgaacaaat ttcagcttcg      180
ggtagaagac tttcgatgcg cttcagagct tctattggga aatctgacac cacttgatta     240
aatagcctac ccccgaattg ggggattggt cattttttgc tgtgaaggta gttttgatgc     300
atatgacctg cgtttataaa gaaatgtaaa cgtgatcaga tcgatataaa agaaacagtt     360
tgtactcagg tttgaagcat tttctccgat tcgcctggca aaaatctcaa ttgtcgctta     420
cagttttttct caacgacagg ctgctaagct gctagttcgg tggcctagtg agtggcgttt    480
acttggataa aagtaatccc atgtcgtgat cagccatttt gggttgtttc catagcaatc     540
caaaggtttc gtctttcgat acctattcaa ggagccttcg cctctatgaa acgcatgaaa     600
tcgctggctg cggcgctcac cgtcgctggg gccatgctgg ccgcacctgt ggcaacggca     660
gaagttcagc tggttgagtc cggcggtggc ctggttcagc aggtcgctc cctgcgtctc      720
tcctgcgcag cttccggctt caccttcgat gactacgcaa tgcactgggt tcgtcaggct     780
cctggcaagg gcctggaatg ggtgtccgca atcacctgga actccggtca catcgattac     840
gctgactccg tcgagggccg cttcaccatc tcccgtgata cgctaagaa ctccctgtac      900
ctccagatga actccctccg tgcagaagac accgctgtct actactgcgc aaaggtttcc     960
tacctgtcca ccgcttcctc cctcgattac tggggtcagg gcaccctggt taccgtgtcc    1020
```

```
tccgcctcca ccaagggtcc atccgtgttc ccgctcgcac catcctccaa gtccacctcc    1080
ggtggcaccg ccgcgctggg ttgcctcgtc aaggactact ccccagaacc tgtcaccgtt    1140
tcctggaact ccggtgccct gacctccggt gtgcacacct cccagcggt cctccagtcc     1200 tccggtctgt actccctctc ctccgtggtc accgtcccta gctcctccct gggcacccag    1260
acctacatct gcaacgtgaa ccacaagcct tccaacacca aggttgataa aaggtggag    1320 ccgaagtcct gcgacaagac ccacacctgc taacaaattc ctgtgaagta gctgatttag   1380
tacttttcgg aggtgtctat tcttaccaaa tcgtcaagtt gtgggtagag tcacctgaat    1440
attaattgca ccgcacgggt gatatatgct tatttgctca agtagttcga ggttaagtgt    1500
attttaggtg aacaaatttc agcttcgggt agaagacttt cgatgcgctt cagagcttct    1560
attgggaaat ctgacaccac ttgattaaat agcctacccc cgaattgggg gattggtcat    1620
tttttgctgt gaaggtagtt ttgatgcata tgacctgcgt ttataaagaa atgtaaacgt    1680
gatcagatcg atataaaaga aacagtttgt actcaggttt gaagcatttt ctccgattcg    1740
cctggcaaaa atctcaattg tcgcttacag ttttttctcaa cgacaggctg ctaagctgct   1800
agttcggtgg cctagtgagt ggcgtttact tggataaaag taatcccatg tcgtgatcag    1860
ccattttggg ttgtttccat agcaatccaa aggtttcgtc tttcgatacc tattcaagga   1920
gccttcgcct ctatgaaacg catgaaatcg ctggctgcgg cgctcaccgt cgctggggcc    1980
atgctggccg cacctgtggc aacggcagat atccagatga cccagtcccc atcctccctg    2040
tccgcttccg ttggtgaccg cgtgaccatc acctgccgtg catcccaggg catccgcaac    2100
tacctggctt ggtatcagca gaagccgggc aaggccccaa agctgctcat ctacgcagct    2160 tccacctcc agtccggcgt gccttccgt ttctccggct ccggttccgg caccgatttc      2220
accctgacca tctcctccct ccagcctgaa gatgtgcgca cctactactg ccagcgttac    2280
aaccgtgcac cgtacacctt cggtcaggc accaaggttg aaatcaagcg taccgtggcc    2340
gcgccatccg tcttcatctt cccaccttcc gatgagcagc tgaagtccgg caccgcatcc    2400
gtggtctgcc tgctcaacaa cttctaccct cgcgaggcga aggtccagtg gaaggttgac    2460
aacgcactgc agtccggcaa ctcccaggaa tccgtgaccg agcaggattc caaggactcc    2520
acctactccc tctcctccac cctgaccctc tccaaggctg attacgaaaa gcacaaggtt    2580
tacgcctgcg aggtgaccca ccagggtctc tcctccccag tcaccaagtc cttcaaccgc    2640
ggcgaatgct aatctaga                                                  2658

<210> SEQ ID NO 109
<211> LENGTH: 2658
<212> TYPE: DNA
<213> ORGANISM: Artificial Sequence
<220> FEATURE:
<223> OTHER INFORMATION: synthesized DNA

<400> SEQUENCE: 109
ggatcccaaa ttcctgtgaa gtagctgatt tagtactttt cggaggtgtc tattcttacc    60
aaatcgtcaa gttgtgggta gagtcacctg aatattaatt gcaccgcacg ggtgatatat    120
gcttatttgc tcaagtagtt cgaggttaag tgtattttag gtgaacaaat ttcagcttcg    180
ggtagaagac tttcgatgcg cttcagagct tctattggga aatctgacac cacttgatta    240
aatagcctac ccccgaattg ggggattggt catttttttgc tgtgaaggta gttttgatgc    300
atatgacctg cgtttataaa gaaatgtaaa cgtgatcaga tcgatataaa agaaacagtt    360
```

```
tgtactcagg tttgaagcat tttctccgat tcgcctggca aaaatctcaa ttgtcgctta    420
cagttttttct caacgacagg ctgctaagct gctagttcgg tggcctagtg agtggcgttt    480
acttggataa aagtaatccc atgtcgtgat cagccatttt gggttgtttc catagcaatc    540
caaaggtttc gtctttcgat acctattcaa ggagccttcg cctctatgaa acgcatgaaa    600
tcgctggctg cggcgctcac cgtcgctggg gccatgctgg ccgcacctgt ggcaacggca    660
gatatccaga tgacccagtc cccatcctcc ctgtccgctt ccgttggtga ccgcgtgacc    720
atcacctgcc gtgcatccca gggcatccgc aactacctgg cttggtatca gcagaagccg    780
ggcaaggccc caaagctgct catctacgca gcttccaccc tccagtccgg cgtgccttcc    840
cgtttctccg gctccggttc cggcaccgat ttcaccctga ccatctcctc cctccagcct    900
gaagatgtgg cgacctacta ctgccagcgt acaaccgtg caccgtacac cttcggtcag    960
ggcaccaagg ttgaaatcaa gcgtaccgtg gccgcgccat ccgtcttcat cttcccacct   1020
tccgatgagc agctgaagtc cggcaccgca tccgtggtct gcctgctcaa caacttctac   1080
cctcgcgagg cgaaggtcca gtggaaggtt gacaacgcac tgcagtccgg caactcccag   1140
gaatccgtga ccgagcagga ttccaaggac tccacctact ccctctcctc caccctgacc   1200
ctctccaagg ctgattacga aaagcacaag gtttacgcct gcgaggtgac ccaccagggt   1260
ctctcctccc cagtcaccaa gtccttcaac cgcggcgaat gctaacaaat tcctgtgaag   1320
tagctgattt agtactttc ggaggtgtct attcttacca aatcgtcaag ttgtgggtag   1380
agtcacctga atattaattg caccgcacgg gtgatatatg cttatttgct caagtagttc   1440
gaggttaagt gtattttagg tgaacaaatt tcagcttcgg gtagaagact ttcgatgcgc   1500
ttcagagctt ctattgggaa atctgacacc acttgattaa atagcctacc cccgaattgg   1560
gggattggtc attttttgct gtgaaggtag ttttgatgca tatgacctgc gtttataaag   1620
aaatgtaaac gtgatcagat cgatataaaa gaaacagttt gtactcaggt ttgaagcatt   1680
ttctccgatt cgcctggcaa aaatctcaat tgtcgcttac agttttttctc aacgacaggc   1740
tgctaagctg ctagttcggt ggcctagtga gtggcgttta cttggataaa agtaatccca   1800
tgtcgtgatc agccattttg ggttgtttcc atagcaatcc aaaggtttcg tctttcgata   1860
cctattcaag gagccttcgc ctctatgaaa cgcatgaaat cgctggctgc ggcgctcacc   1920
gtcgctgggg ccatgctggc cgcacctgtg gcaacggcag aagttcagct ggttgagtcc   1980
ggcggtggcc tggttcagcc aggtcgctcc ctgcgtctct cctgcgcagc ttccggcttc   2040
accttcgatg actacgcaat gcactgggtt cgtcaggctc ctggcaaggg cctggaatgg   2100
gtgtccgcaa tcacctggaa ctccggtcac atcgattacg ctgactccgt cgagggccgc   2160
ttcaccatct cccgtgataa cgctaagaac tccctgtacc tccagatgaa ctccctccgt   2220
gcagaagaca ccgctgtcta ctactgcgca aaggtttcct acctgtccac cgcttcctcc   2280
ctcgattact ggggtcaggg caccctggtt accgtgtcct ccgcctccac caagggtcca   2340
tccgtgttcc cgctcgcacc atcctccaag tccacctccg gtggcaccgc cgcgctgggt   2400
tgcctcgtca aggactactt cccagaacct gtcaccgttt cctggaactc cggtgccctg   2460
acctccggtg tgcacacctt cccagcggtc ctccagtcct ccggtctgta ctccctctcc   2520
tccgtggtca ccgtccctag ctcctccctg ggcacccaga cctacatctg caacgtgaac   2580
cacaagcctt ccaacaccaa ggttgataag aaggtggagc cgaagtcctg cgacaagacc   2640
cacacctgct aatctaga                                                 2658
```

<210> SEQ ID NO 110
<211> LENGTH: 693
<212> TYPE: DNA
<213> ORGANISM: Artificial Sequence
<220> FEATURE:
<223> OTHER INFORMATION: H chain of Adalimumab

<400> SEQUENCE: 110

```
gaagttcagc tggttgagtc cggcggtggc ctggttcagc caggtcgctc cctgcgtctc    60
tcctgcgcag cttccggctt caccttcgat gactacgcaa tgcactgggt tcgtcaggct   120
cctggcaagg gcctggaatg ggtgtccgca atcacctgga actccggtca catcgattac   180
gctgactccg tcgagggccg cttcaccatc tccgtgata  acgctaagaa ctccctgtac   240
ctccagatga actccctccg tgcagaagac accgctgtct actactgcgc aaaggtttcc   300
tacctgtcca ccgcttcctc cctcgattac tggggtcagg gcaccctggt taccgtgtcc   360
tccgcctcca ccaagggtcc atccgtgttc ccgctcgcac catcctccaa gtccacctcc   420
ggtggcaccg ccgcgctggg ttgcctcgtc aaggactact tcccagaacc tgtcaccgtt   480
tcctggaact ccggtgccct gacctccggt gtgcacacct cccagcggt cctccagtcc    540
tccggtctgt actccctctc ctccgtggtc accgtcccta gctcctccct gggcacccag   600
acctacatct gcaacgtgaa ccacaagcct tccaacacca aggttgataa gaaggtggag   660
ccgaagtcct gcgacaagac ccacacctgc taa                                693
```

<210> SEQ ID NO 111
<211> LENGTH: 230
<212> TYPE: PRT
<213> ORGANISM: Artificial Sequence
<220> FEATURE:
<223> OTHER INFORMATION: H chain of Adalimumab

<400> SEQUENCE: 111

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys
225                 230
```

<210> SEQ ID NO 112
<211> LENGTH: 645
<212> TYPE: DNA
<213> ORGANISM: Artificial Sequence
<220> FEATURE:
<223> OTHER INFORMATION: L chain of Adalimumab

<400> SEQUENCE: 112

```
gatatccaga tgacccagtc ccatcctcc ctgtccgctt ccgttggtga ccgcgtgacc    60
atcacctgcc gtgcatccca gggcatccgc aactacctgg cttggtatca gcagaagccg   120
ggcaaggccc caaagctgct catctacgca gcttccaccc tccagtccgg cgtgccttcc   180
cgtttctccg gctccggttc cggcaccgat tcaccctga ccatctcctc cctccagcct   240
gaagatgtgg cgacctacta ctgccagcgt acaaccgtg caccgtacac cttcggtcag   300
ggcaccaagg ttgaaatcaa gcgtaccgtg gccgcgccat ccgtcttcat cttcccacct   360
tccgatgagc agctgaagtc cggcaccgca tccgtggtct gcctgctcaa caacttctac   420
cctcgcgagg cgaaggtcca gtggaaggtt gacaacgcac tgcagtccgg caactcccag   480
gaatccgtga ccgagcagga ttccaaggac tccaccctact ccctctcctc caccctgacc   540
ctctccaagg ctgattacga aaagcacaag gtttacgcct gcgaggtgac ccaccagggt   600
ctctcctccc cagtcaccaa gtccttcaac cgcggcgaat gctaa                    645
```

<210> SEQ ID NO 113
<211> LENGTH: 214
<212> TYPE: PRT
<213> ORGANISM: Artificial Sequence
<220> FEATURE:
<223> OTHER INFORMATION: L chain of Adalimumab

<400> SEQUENCE: 113

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 114
<211> LENGTH: 1500
<212> TYPE: DNA
<213> ORGANISM: Corynebacterium glutamicum ATCC13869

<400> SEQUENCE: 114
atgtttaaca accgtatccg cactgcagct ctcgctggtg caatcgcaat ctccaccgca      60
gcttccggcg tagctatccc agcattcgct caggagacca acccaacctt caacatcaac     120
aacggcttca cgatgctga tggatccacc atccagccag ttgagccagt taaccacacc      180
gaggaaaccc tccgcgacct gactgactcc accggcgctt acctggaaga gttccagtac     240
ggcaacgttg aggaaatcgt tgaagcatac ctgcaggttc aggcttccgc agacggattc     300
gatccttctg gcaggctgc ttacgaggct ttcgaggctc tcgcgttcg tgcatcccag       360 gagctcgcgg cttccgctga ccatcact aagacccgcg agtccgttgc ttacgcactc      420
aaggctgacc gcgaagctac cgcagctttc gaggcttacc tcagcgctct tcgtcaggtt     480
tcagtcatca cgatctgat cgctgatgct aacgccaaga caagactga ctttgcagag      540 atcgagctct acgatgttct ttacaccgac gccgacatct ctggcgatgc tccacttctt    600
gctcctgcat acaaggagct gaaggacctt caggctgagg ttgacgcaga cttcgagtgg    660
ttgggcgagt tcgcaattga taacaatgaa gacaactacg tcattcgtac tcacatccct    720
gctgtagagg cactcaaggc agcgatcgat tcactggtcg acaccgttga gccacttcgt    780
gcagacgcta tcgctaagaa catcgaggct cagaagtctg acgttctggt tccccagctc    840
ttcctcgagc gtgcaactgc acagcgcgac accctgcgtg ttgtagaggc aatcttctct    900
acctctgctc gttacgttga actctacgag aacgtcgaga cgttaacgt tgagaacaag    960 acccttcgcc agcactactc tttccctgatc cctaacctct tcatcgcagc ggttggcaac   1020
atcaacgagc tcaacaatgc agatcaggct gcacgtgagc tcttcctcga ttgggacacc    1080
gacctcacca ccaacgatga ggacgaagct tactaccagg ctaagctcga cttcgctatc    1140
gagacctacg caaagatcct gatcaacggt gaagtttggc aggagccact cgcttacgtc    1200
cagaacctgg atgcaggcgc acgtcaggaa gcagctgacc gcgaagcaga gcgcgcagct    1260
gacgcagcat accgcgctga gcagctccgc atcgctcagg aagcagctga cgctcagaag    1320
gctctcgctg aggctcttgc taatgcaggc aacaacgaca acggtggcga caactcctcc    1380
gacgacaagg gaaccggttc ttccgacatc ggaacctggg gacctttcgc agcaattgca    1440
gctatcatcg cagcaatcgc agctatcttc ccattcctct ccggtatcgt taagttctaa   1500

<210> SEQ ID NO 115
<211> LENGTH: 499
<212> TYPE: PRT
<213> ORGANISM: Corynebacterium glutamicum ATCC13869

<400> SEQUENCE: 115
```

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Gln Glu
            20                  25                  30

Thr Asn Pro Thr Phe Asn Ile Asn Asn Gly Phe Asn Asp Ala Asp Gly
        35                  40                  45

Ser Thr Ile Gln Pro Val Glu Pro Val Asn His Thr Glu Glu Thr Leu
50                  55                  60

Arg Asp Leu Thr Asp Ser Thr Gly Ala Tyr Leu Glu Glu Phe Gln Tyr
65                  70                  75                  80

Gly Asn Val Glu Glu Ile Val Glu Ala Tyr Leu Gln Val Gln Ala Ser
                85                  90                  95

Ala Asp Gly Phe Asp Pro Ser Glu Gln Ala Ala Tyr Glu Ala Phe Glu
            100                 105                 110

Ala Ala Arg Val Arg Ala Ser Gln Glu Leu Ala Ser Ala Glu Thr
        115                 120                 125

Ile Thr Lys Thr Arg Glu Ser Val Ala Tyr Ala Leu Lys Ala Asp Arg
130                 135                 140

Glu Ala Thr Ala Ala Phe Glu Ala Tyr Leu Ser Ala Leu Arg Gln Val
145                 150                 155                 160

Ser Val Ile Asn Asp Leu Ile Ala Asp Ala Asn Ala Lys Asn Lys Thr
            165                 170                 175

Asp Phe Ala Glu Ile Glu Leu Tyr Asp Val Leu Tyr Thr Asp Ala Asp
        180                 185                 190

Ile Ser Gly Asp Ala Pro Leu Leu Ala Pro Ala Tyr Lys Glu Leu Lys
    195                 200                 205

Asp Leu Gln Ala Glu Val Asp Ala Asp Phe Glu Trp Leu Gly Glu Phe
210                 215                 220

Ala Ile Asp Asn Asn Glu Asp Asn Tyr Val Ile Arg Thr His Ile Pro
225                 230                 235                 240

Ala Val Glu Ala Leu Lys Ala Ala Ile Asp Ser Leu Val Asp Thr Val
            245                 250                 255

Glu Pro Leu Arg Ala Asp Ala Ile Ala Lys Asn Ile Glu Ala Gln Lys
        260                 265                 270

Ser Asp Val Leu Val Pro Gln Leu Phe Leu Glu Arg Ala Thr Ala Gln
    275                 280                 285

Arg Asp Thr Leu Arg Val Val Glu Ala Ile Phe Ser Thr Ser Ala Arg
290                 295                 300

Tyr Val Glu Leu Tyr Glu Asn Val Glu Asn Val Glu Asn Lys
305                 310                 315                 320

Thr Leu Arg Gln His Tyr Ser Ser Leu Ile Pro Asn Leu Phe Ile Ala
            325                 330                 335

Ala Val Gly Asn Ile Asn Glu Leu Asn Asn Ala Asp Gln Ala Ala Arg
        340                 345                 350

Glu Leu Phe Leu Asp Trp Asp Asp Leu Thr Thr Asn Asp Glu Asp
    355                 360                 365

Glu Ala Tyr Tyr Gln Ala Lys Leu Asp Phe Ala Ile Glu Thr Tyr Ala
370                 375                 380

Lys Ile Leu Ile Asn Gly Glu Val Trp Gln Glu Pro Leu Ala Tyr Val
385                 390                 395                 400

Gln Asn Leu Asp Ala Gly Ala Arg Gln Glu Ala Asp Arg Glu Ala
            405                 410                 415
```

```
Glu Arg Ala Ala Asp Ala Ala Tyr Arg Ala Glu Gln Leu Arg Ile Ala
        420             425             430

Gln Glu Ala Ala Asp Ala Gln Lys Ala Leu Ala Glu Ala Leu Ala Asn
        435             440             445

Ala Gly Asn Asn Asp Asn Gly Gly Asp Asn Ser Ser Asp Asp Lys Gly
    450             455             460

Thr Gly Ser Ser Asp Ile Gly Thr Trp Gly Pro Phe Ala Ala Ile Ala
465             470             475             480

Ala Ile Ile Ala Ala Ile Ala Ala Ile Phe Pro Phe Leu Ser Gly Ile
            485             490             495

Val Lys Phe
```